(12) United States Patent
Irvine et al.

(10) Patent No.: US 11,261,226 B2
(45) Date of Patent: Mar. 1, 2022

(54) CELL SURFACE COUPLING OF NANOPARTICLES

(71) Applicant: MASSACHUSETTS INSTITUTE OF TECHNOLOGY, Cambridge, MA (US)

(72) Inventors: Darrell J. Irvine, Arlington, MA (US); Yiran Zheng, Cambridge, MA (US); Li Tang, Quincy, MA (US)

(73) Assignee: MASSACHUSETTS INSTITUTE OF TECHNOLOGY (MITN1), Cambridge, MA (US)

( * ) Notice: Subject to any disclaimer, the term of this patent is extended or adjusted under 35 U.S.C. 154(b) by 0 days.

(21) Appl. No.: 17/318,590

(22) Filed: May 12, 2021

(65) Prior Publication Data
US 2021/0269500 A1    Sep. 2, 2021

Related U.S. Application Data

(62) Division of application No. 15/236,186, filed on Aug. 12, 2016, now Pat. No. 11,034,752.

(60) Provisional application No. 62/204,337, filed on Aug. 12, 2015.

(51) Int. Cl.
| | | |
|---|---|---|
| *C07K 14/55* | (2006.01) | |
| *C07K 14/705* | (2006.01) | |
| *C07K 14/54* | (2006.01) | |
| *A61K 9/127* | (2006.01) | |
| *C07K 16/28* | (2006.01) | |
| *C07K 14/715* | (2006.01) | |
| *A61K 47/68* | (2017.01) | |
| *A61K 47/69* | (2017.01) | |
| *A61K 47/60* | (2017.01) | |
| *A61K 39/00* | (2006.01) | |
| *C07K 14/725* | (2006.01) | |
| *C07K 16/30* | (2006.01) | |
| *C07K 19/00* | (2006.01) | |
| *C12N 5/0783* | (2010.01) | |
| *C12N 5/00* | (2006.01) | |
| *A61P 35/00* | (2006.01) | |

(52) U.S. Cl.
CPC .............. *C07K 14/55* (2013.01); *A61K 9/127* (2013.01); *A61K 39/0011* (2013.01); *A61K 47/60* (2017.08); *A61K 47/6849* (2017.08); *A61K 47/6889* (2017.08); *A61K 47/6903* (2017.08); *A61K 47/6913* (2017.08); *C07K 14/5443* (2013.01); *C07K 14/7051* (2013.01); *C07K 14/70503* (2013.01); *C07K 14/70517* (2013.01); *C07K 14/70578* (2013.01); *C07K 14/70589* (2013.01); *C07K 14/7155* (2013.01); *C07K 16/2806* (2013.01); *C07K 16/289* (2013.01); *C07K 16/2845* (2013.01); *C07K 16/30* (2013.01); *C07K 19/00* (2013.01); *A61K 39/001104* (2018.08); *A61K 2039/505* (2013.01); *A61K 2039/5156* (2013.01); *A61K 2039/5158* (2013.01); *A61K 2039/55527* (2013.01); *A61K 2039/55533* (2013.01); *A61K 2039/57* (2013.01); *A61K 2039/585* (2013.01); *A61P 35/00* (2018.01); *C07K 2317/622* (2013.01); *C07K 2319/00* (2013.01); *C07K 2319/03* (2013.01); *C07K 2319/30* (2013.01); *C07K 2319/33* (2013.01); *C07K 2319/70* (2013.01); *C12N 5/0006* (2013.01); *C12N 5/0636* (2013.01); *C12N 5/0638* (2013.01); *C12N 2501/2315* (2013.01)

(58) Field of Classification Search
None
See application file for complete search history.

(56) References Cited

U.S. PATENT DOCUMENTS

| | | |
|---|---|---|
| 5,409,698 A | 4/1995 | Anderson et al. |
| 5,453,491 A | 9/1995 | Takatsu et al. |
| 5,464,629 A | 11/1995 | Monshipouri et al. |
| 5,753,261 A | 5/1998 | Fernandez et al. |
| 5,773,006 A | 6/1998 | Anderson et al. |
| 6,117,982 A | 9/2000 | Chang |
| 6,120,751 A | 9/2000 | Unger |
| 6,194,388 B1 | 2/2001 | Krieg et al. |
| 6,197,298 B1 | 3/2001 | Chang |
| 6,319,715 B1 | 11/2001 | Luo et al. |
| 6,544,549 B1 | 4/2003 | Boni et al. |
| 6,693,086 B1 | 2/2004 | Dow et al. |
| 6,787,132 B1 | 9/2004 | Gabizon et al. |
| 7,108,863 B2 | 9/2006 | Zalipsky et al. |
| 7,122,202 B2 | 10/2006 | Allen et al. |
| 7,223,544 B2 | 5/2007 | Luo et al. |
| 7,402,431 B2 | 7/2008 | Har-Noy |
| 8,192,485 B2 | 6/2012 | Ravi |

(Continued)

FOREIGN PATENT DOCUMENTS

| | | |
|---|---|---|
| JP | H3-244601 A | 10/1991 |
| JP | 2009-149526 A | 7/2009 |

(Continued)

OTHER PUBLICATIONS

Krishna, N. et al., "Genetic Determinants of Rous Sarcoma Virus Particle Size," Journal of Virology, vol. 72 (1):564-577 (1998).

(Continued)

*Primary Examiner* — Brad Duffy
(74) *Attorney, Agent, or Firm* — Nelson Mullins Riley & Scarborough LLP

(57) ABSTRACT

The present disclosure is directed, in some embodiments, to methods and compositions of comprising a cell having a non-internalizing receptor, and a nanoparticle surface-modified with a ligand that binds to the non-internalizing receptor.

20 Claims, 13 Drawing Sheets
Specification includes a Sequence Listing.

(56) References Cited

U.S. PATENT DOCUMENTS

| | | |
|---|---|---|
| 8,747,869 B2 | 6/2014 | Irvine et al. |
| 8,951,542 B2 | 2/2015 | Irvine et al. |
| 9,090,640 B2 | 7/2015 | Bierbach et al. |
| 9,149,432 B2 | 10/2015 | Irvine et al. |
| 9,149,535 B2 | 10/2015 | Xu et al. |
| 9,283,184 B2 | 3/2016 | Irvine et al. |
| 9,339,462 B2 | 5/2016 | Irvine et al. |
| 9,393,199 B2 | 7/2016 | Irvine et al. |
| 9,445,994 B2 | 9/2016 | Irvine et al. |
| 9,603,944 B2 | 3/2017 | Tang et al. |
| 9,616,020 B2 | 4/2017 | Irvine et al. |
| 9,750,803 B2 | 9/2017 | Irvine et al. |
| 9,907,753 B2 | 3/2018 | Irvine et al. |
| 10,226,510 B2 | 3/2019 | Tang et al. |
| 10,357,544 B2 | 7/2019 | Tang et al. |
| 10,588,942 B2 | 3/2020 | Tang et al. |
| 2001/0038859 A1 | 11/2001 | Maskiewicz et al. |
| 2001/0043929 A1 | 11/2001 | Zalipsky et al. |
| 2002/0151004 A1 | 10/2002 | Craig |
| 2003/0054027 A1 | 3/2003 | Unger |
| 2003/0235619 A1 | 12/2003 | Allen et al. |
| 2004/0247624 A1 | 12/2004 | Unger et al. |
| 2005/0042298 A1 | 2/2005 | Pardridge et al. |
| 2005/0130180 A1 | 6/2005 | Luo et al. |
| 2005/0214274 A1 | 9/2005 | Har-Noy |
| 2005/0266067 A1 | 12/2005 | Sengupta et al. |
| 2006/0046967 A1 | 3/2006 | Satyam |
| 2006/0263857 A1 | 11/2006 | Lefrancois et al. |
| 2006/0270030 A1 | 11/2006 | Voigt et al. |
| 2006/0275371 A1 | 12/2006 | Dai et al. |
| 2007/0059318 A1 | 3/2007 | Balu-Iyer et al. |
| 2007/0148246 A1 | 6/2007 | Luo et al. |
| 2007/0298093 A1 | 12/2007 | Konur et al. |
| 2008/0014144 A1 | 1/2008 | Saltzman et al. |
| 2008/0267986 A1 | 10/2008 | Pfeifer et al. |
| 2008/0279836 A1 | 11/2008 | Har-Noy |
| 2010/0226973 A1 | 9/2010 | Fujii et al. |
| 2010/0255499 A1 | 10/2010 | Wender et al. |
| 2010/0323018 A1 | 12/2010 | Irvine et al. |
| 2010/0324124 A1 | 12/2010 | Irvine et al. |
| 2011/0020388 A1 | 1/2011 | Zepp et al. |
| 2011/0177156 A1 | 7/2011 | Szoka, Jr. et al. |
| 2011/0206740 A1 | 8/2011 | Karp et al. |
| 2011/0229529 A1 | 9/2011 | Irvine et al. |
| 2011/0229556 A1 | 9/2011 | Irvine et al. |
| 2011/0293705 A1 | 12/2011 | Irvine et al. |
| 2012/0003295 A1 | 1/2012 | Jiang et al. |
| 2012/0121688 A1 | 5/2012 | Ishii et al. |
| 2012/0177724 A1 | 7/2012 | Irvine et al. |
| 2013/0203675 A1 | 8/2013 | DeSimone et al. |
| 2013/0302257 A1 | 11/2013 | Minko et al. |
| 2013/0337471 A1 | 12/2013 | Nie et al. |
| 2014/0017170 A1 | 1/2014 | Irvine et al. |
| 2014/0134128 A1 | 5/2014 | Wong et al. |
| 2014/0377334 A1 | 12/2014 | Irvine et al. |
| 2015/0110740 A1 | 4/2015 | Tang et al. |
| 2015/0272884 A1 | 10/2015 | Irvine et al. |
| 2016/0030304 A1 | 2/2016 | Nagamatsu et al. |
| 2016/0038415 A1 | 2/2016 | Irvine et al. |
| 2016/0256386 A1 | 9/2016 | Irvine et al. |
| 2016/0303046 A1 | 10/2016 | Irvine et al. |
| 2016/0375149 A1 | 12/2016 | Irvine et al. |
| 2017/0049882 A1 | 2/2017 | Irvine et al. |
| 2017/0080104 A1 | 3/2017 | Irvine et al. |
| 2017/0196938 A1 | 7/2017 | Tang et al. |
| 2017/0266114 A1 | 9/2017 | Irvine et al. |
| 2018/0110733 A1 | 4/2018 | Irvine et al. |
| 2018/0185473 A1 | 7/2018 | Irvine et al. |
| 2019/0083576 A1 | 3/2019 | Tang et al. |
| 2020/0360482 A1 | 11/2020 | Tang et al. |

FOREIGN PATENT DOCUMENTS

| | | |
|---|---|---|
| JP | 2013-511539 A | 4/2013 |
| JP | 2013-173689 A | 9/2013 |
| WO | 2004/032970 A2 | 4/2004 |
| WO | 2007/034479 A2 | 3/2007 |
| WO | 2010/059253 A2 | 5/2010 |
| WO | 2010/104865 A2 | 9/2010 |
| WO | 2010/147655 A2 | 12/2010 |
| WO | 2011/063156 A2 | 5/2011 |
| WO | 2012/040323 A2 | 3/2012 |
| WO | 2012/112689 A1 | 8/2012 |
| WO | 2012/142410 A2 | 10/2012 |
| WO | 2015/048498 A2 | 4/2015 |
| WO | 2017/218533 A1 | 12/2017 |

OTHER PUBLICATIONS

Kudchodkar, S. et al., "Improving CAR T Cell Efficacy for Solid Tumors By Nanogel-Based Delivery of Immunomodulatory Proteins," Molecular Therapy: The Journal of The American Society of Gene Therapy, vol. 23(SI):S207-S207 (2015).

Kwon et al., "In vivo targeting of dendritic cells for activation of cellular immunity using vaccine carriers based on pH-responsive microparticles," Proc Natl Acad Sci USA, vol. 102(51):18264-18268 (2005).

Kwong, B. et al., "Localized immunotherapy via liposome-anchored Anti-CD137 + IL-2 prevents lethal toxicity and elicits local and systemic antitumor immunity," Cancer Res., vol. 73(5):1547-1558 (2013).

Kwong, B. et al., "Induction of potent anti-tumor responses while eliminating systemic side effects via liposome-anchored combinatorial immunotherapy," Biomaterials, Elsevier Science Publishers BV, vol. 32(22):5134-5147 (2011).

Kwong, B., "Liposome-anchored local delivery of immunomodulatory agents for tumor therapy," Biological Engineering, Massachusetts Institute of Technology. 2005. Jun. 2012. (175 pages).

Lachman, L. et al., "Cytokine-containing liposomes as vaccine adjuvants," Eur Cytokine Netw., vol. 7(4):693-698 (1996).

Lateef et al., "An improved protocol for coupling synthetic peptides to carrier protiens for antibody production using DMF to solubilize peptides", J Biomolecular Techniques, vol. 18: 173-176 (2007).

Lavelle, E.C. et al., "The stability and immunogenicity of a protein antigen encapsulated in biodegradable microparticles based on blends of lactide polymers and polyethylene glycol.," Vaccine, vol. 17(6):512-529 (1999).

Lee, J. et al., "Multifunctional nanoarchitectures from DNA-based ABC monomers," Nat Nanotechnol. vol. 4(7):430-436 (2009).

Leland et al., "Cancer chemotherpay-ribonucleases to the rescue", Chem Biol., vol. 8 (5): 405-413 (2011).

Li, J. et al., "Purification of melanoma reactive T cell by using a monocyte-based solid phase T-cell selection system for adoptive therapy," J Immunother., vol. 31(1):81-88 (2008).

Li, Y. et al., "PEGylated PLGA nanoparticles as protein carriers: synthesis, preparation and biodistribution in rats," J Control Release, vol. 71(2):203-211. (2001).

Lodish, H. et al., "Chemical Foundations," In: Molecular Cell Biology, Fifth Eds. Chapter 2, pp. 29-57 (2004).

Lowenthal, J. et al., "Similarities between interleukin-2 receptor number and affinity on activated B and T lymphocytes," Nature, vol. 315(6021):669-672 (1985).

Lowenthal, J. et al., "High and low affinity IL 2 receptors: analysis by IL 2 dissociation rate and reactivity with monoclonal anti-receptor antibody PC61," J Immunol., vol. 135(6):3988-3994 (1985).

Lu, W. et al., "Cationic albumin-conjugated pegylated nanoparticles as novel drug carrier for brain delivery," J Control Release, vol. 107(3):428-448 (2005).

Lutsiak, M. et al., "Analysis of poly(D,L-lactic-co-glycolic acid) nanosphere uptake by human dendritic cells and macrophages in vitro," Pharm Res., vol. 19(10):1480-1487 (2002).

MacLaughlin, C.M., et al., "Polymer-coated surface enhanced Raman scattering (SERS) gold nanoparticles for multiplexed labeling of chronic lymphocytic leukemia cells," Frontiers in Biological Detection: From Nanosensors to Systems IV, SPIE, vol. 8212(1):1-11 (2012).

(56) References Cited

OTHER PUBLICATIONS

Maeda, H. et al., "Tumor vascular permeability and the EPR effect in macromolecular therapeutics: a review.," J Control Release, vol. 65(1-2):271-284 (2000).
Maloy, K. et al., "Induction of mucosal and systemic immune responses by immunization with ovalbumin entrapped in poly(lactide-co-glycolide) microparticles," Immunology, vol. 81(4):661-667 (1994).
Markley, J. et al., "IL-7 and IL-21 are superior to IL-2 and IL-15 in promoting human T cell-mediated rejection of systemic lymphoma in immunodeficient mice," Blood, vol. 115(17):3508-3519 (2010).
Martinez Gomez, J. et al., "A protective allergy vaccine based on CpG-and protamine-containing PLGA microparticles," Pharm Res., vol. 24(10):1927-1935 (2007).
Matsumoto, N. et al. "Synthesis of nanogel-protein conjugates," Poly Chem., vol. (8):2464-2469 (2013).
Matsumura, Y. et al., "A new concept for macromolecular therapeutics in cancer chemotherapy: mechanism of tumoritropic accumulation of proteins and the antitumor agent smancs," Cancer Res., vol. 46(12 Pt 1):6387-6392 (1986).
McKee, A. et al., "How do adjuvants work? Important considerations for new generation adjuvants," Immunity, vol. 27(5):687-690 (2007).
Mellman, I. et al., "Cancer immunotherapy comes of age," Nature, vol. 480(7378):480-489 (2011).
Meng, F. et al., "Reduction-sensitive polymers and bioconjugates for biomedical applica-tions," Biomaterials, vol. 30:2180-2198 (2009).
Minami, Y. et al., "The IL-2 receptor complex: its structure, function, and target genes," Annu Rev. Immunol., vol. 11:245-268 (1993).
Moghimi, S. et al., "Long-circulating and target-specific nanoparticles: theory to practice," Pharmacol Rev. vol. 53(2):283-318 (2001).
Mohammed, A. et al., "Lyophilisation and sterilisation of liposomal vaccines to produce stable and sterile products," Methods, vol. 40(1):30-38 (2006).
Moon, J. et al., "Engineering nano-and microparticles to tune immunity," Adv Mater., vol. 24(28):3724-3746 (2012).
Moon, J. et al., "Enhancing humoral responses to a malaria antigen with nanoparticle vaccines that expand Tfh cells and promote germinal center induction," Proc Natl Acad Sci USA., vol. 109(4):1080-1085 (2012).
Moon, J. et al., "Interbilayer-crosslinked multilamellar vesicles as synthetic vaccines for potent humoral and cellular immune responses," Nat Mater., vol. 10(3) 243-251 (2011).
Moore, A. et al., "Tracking the recruitment of diabetogenic CD8+ T-cells to the pancreas in real time," Diabetes, vol. 53(6):1459-1466 (2004).
Morgan, R. et al., "Cancer regression in patients after transfer of genetically engineered lymphocytes," Science, vol. 314(5796):126-129 (2006).
Mortensen et al., Next generation adoptive immunotherapy—human T cells as carriers of; therapeutic nanoparticles. J Nanosci Nanotechnol. Dec. 2007;7(12):4575-80.
Mundargi, R. et al., "Nano/micro technologies for delivering macromolecular therapeutics using poly(D,L-lactide-co-glycolide) and its derivatives," J Control Release., vol. 125(3):193-209 (2008).
Murcia et al., "Design of quantum dot-conjugated lipids for long-term, high-speed tracking experiments on cell surfaces," J Am Chem Soc., vol. 130(45): 15054-15062 (2008).
Murphy, R. et al., "Endosome pH measured in single cells by dual fluorescence flow cytometry: rapid acidification of insulin to pH 6," J Cell Biol., vol. 98(5): 1757-1762 (1984).
Nguyen et al., "Disulfide-crosslinked heparine-luorinc nanogels as redox-sensistive nanocarrier for intracellular protein deliver", J. Bioactive and Compatible Polymers, vol. 26 (3): 287-300 (2011).
O'Hagan, D. et al., "Induction of potent immune responses by cationic microparticles with adsorbed human immunodeficiency virus DNA vaccines," J Virol., vol. 75(19):9037-9043 (2001).
O'Hagan, D. et al., "Microparticles as potentially orally active immunological adjuvants," Vaccine, vol. 7(5):421-424 (1989).

O'Hagan, D. et al., "Poly(lactide-co-glycolide) microparticles for the development of single-dose controlled-release vaccines," Adv Drug Deliv Rev. vol. 32(3):225-246 (1987).
Overwijk, W. et al., "Tumor regression and autoimmunity after reversal of a functionally tolerant state of self-reactive CD8+ T cells," J Exp Med., vol. 198(4):569-580 (2003).
Owens, D. et al., "Opsonization, biodistribution, and pharmacokinetics of polymeric nanoparticles.," Int J Pharm., vol. 307(1):93-102 (2006).
Park, J. et al., "Anti-HER2 immunoliposomes:enhanced efficacy attributable to targeted delivery," Clin Cancer Res., vol. 8(4):1172-1181 (2002).
Park, J. et al., "Modulation of CD4+ T lymphocyte lineage outcomes with targeted, nanoparticle-mediated cytokine delivery," Mol Pharm., vol. 8(1):143-152 (2011).
Partial European Search Report, European Application No. 16836005. 5, dated Mar. 18, 2019, 16 pages.
Paulos, C. et al., "Toll-like receptors in tumor immunotherapy," Clin Cancer Res., vol. 13(18 Pt 1):5280-5289 (2007).
Topalian et al., "Expansion of human tumor infiltrating lymphocytes for use in immunotherapy trials", J Immunol Methods, 102(1):127-41 (1987).
Torchilin, "Recent advances with liposomes as pharmaceutical carriers," Nat Rev Drug Disc., vol. 4(2): 145-160 (2005).
Tosatto, S.C., et al., "Large-scale prediction of protein structure and function from sequence," Current Pharmaceutical Design, vol. 12:2067-2086 (2006).
Trevaskis, NL et al., "Targeted drug delivery to lymphocytes: a route to site-specific immunomodulation," Mol Pharm. vol. 7(6):2297-2309 (2010).
Tsai, S. et al., "Reversal of autoimmunity by boosting memory-like autoregulatory T cells," Immunity, vol. 32(4):568-580 (2010).
Um et al., "Enzyme-catalysed assembly of DNA hydrogel," Nat Mater. vol. 5(10):797-801 (2006).
Van Broekhoven et al., "The novel chelator lipid 3(nitrilotriacetic acid)-ditetradecylamine (NT A(3)-DTDA) promotes stable binding of His-tagged proteins to liposomal membranes: potent anti-tumor responses induced by simultaneously targeting antigen, cytokine and costimulatory signals to T cells," Biochim Biophys Acta., vol. 1716(2):104-116 (2006).
Vancha, A. et al., "Use of polyethyleneimine polymer in cell culture as attachment factor and lipofection enhancer," BMC Biotechnology, vol. 4 (23) 12 pages.
Vancha, A. et al., "Use of Polyethyleneimine polymer in cell culture as attachment factor and lipofection enhancer," BMC Biotechnology, vol. 4 (23): 12 pages (2004).
Vangala et al., "Comparison of vesicle based antigen delivery systems for delivery of hepatitis B surface antigen," J Controlled Release, vol. 119(1):102-110 (2007).
Vasir et al., "Biodegradable nanoparticles for cytosolic delivery of therapeutics," Adv Drug Deliv Rev. vol. 59(8):718-728 (2007).
Verma et al., "Surface-structure-regulated cell-membrane penetration by monolayer-protected nanoparticles," Nat Mater., vol. 7(7):588-595 (2008).
Von Maltzahn et al., "In vivo tumor cell targeting with click nanoparticles," Bioconjug Chem., vol. 19(8):1570-1578 (2008).
Vonarbourg et al., "Parameters influencing the stealthiness of colloidal drug delivery systems," Biomaterials, vol. 27(24):4356-4373 (2006).
Vugmeyster Yulia et al: "Pharmacokinetic,; biodistribution, and biophysical profiles; of TNF nanobodies conjugated to linear or; branched poly(ethylene glycol).",; Bioconjugate Chemistry Jul. 18, 2012,; vol. 23, No. 7, Jul. 18, 2012 (Jul. 18, 2012),; pp. 1452-1462, XP002735223.
Wakita, D. et al., "An indispensable role of type-I IFN s for inducing CTL-mediated complete eradication of established tumor tissue by CpG-liposome co-encapsulated with model tumor antigen," Int Immunol., vol. 18(3):425-434 (2006).
Walter, R. et al., "Simultaneously targeting CD45 significantly increases cytotoxicity of the anti-CD33 immunoconjugate, gemtuzumab ozogamicin, against acute myeloid leukemia (AML) cells and improves survival of mice bearing human AML xenografts," Blood, vol. 111(9):4813-4816 (2008).

(56) References Cited

OTHER PUBLICATIONS

Wang, X. et al., "A transgene-encoded cell surface polypeptide for selection, in vivo tracking, and ablation of engineered cells," Blood, vol. 118(5):1255-1263 (2011).
Weinstein et al., "Antibody-mediated targeting of liposomes: Binding to lymphocytes does not ensure incorporation of vesicle contents into the cells," Biochem Biophys Acta., vol. 509(2):272-288 (1978).
Westwood, J.et al., "Three agonist antibodies in combination with high-dose IL-2 eradicate orthotopic kidney cancer in mice," Journal of Translational Medicine, vol. 8(42):1-8 (2010).
Westwood, J.et al., "Toll-Like Receptor Triggering and T-Cell Costimulation Induce Potent Antitumor Immunity in Mice," CCR, vol. 15(24):7624-7633 (2009).
Wilson-Welder et al., "Vaccine adjuvants: current challenges and future approaches," J Pharm Sci., vol. 98(4):1278-1316 (2008).
Xing et al., "Disulfide core cross-linked PEGylated polypeptide nanogel prepared by a one-step ring opening copolymerization of n-carboxyandhyrides for drug delivery", Macromolecular Journals, vol. 11:962-969 (2011).
Xu, J. et al., "Rendering protein-based particles transiently insoluble for therapeutic applications," Journal of American Chemistry Society, vol. 134(21): 8774-8777 (2012).
Yan, M. et al., "A novel intracellular protein delivery platform based on single-protein nanocapsules," Nat Nanotechnol., vol. 5(1):48-53 (2009).
Yee et al., "Adoptive T cell therapy using antigen-specific CD8+ T cell clones for the treatment of patients with metastatic melanoma: in vivo persistence, migration, and antitumor effect of transferred T cells," Proc Natl Acad Sci USA., vol. 99(25): 16168-16173 (2002).
Zauner et al., "In vitro uptake of polystyrene microspheres: effect of particle size, cell line and cell density," J Control Release, vol. 71(1):39-51 (2001).
Zhang et al., "Folate-decorated poly(lactide-co-glycolide)-vitamin E TPGS nanoparticles for targeted drug delivery," Biomaterials, vol. 28(10):1889-1899 (2007).
Zhao et al., "Directed cell migration via chemoattractants released from degradable crospheres," Biomaterials, vol. 26(24):5048-5063 (2005).
Zheng et al., "In vivo targeting of adoptively transferred T-cells with antibody and cytokine conjugated liposomes," J Control Release, vol. 172(2):426-445 (2003).
Zheng, "In vivo Arming of Adoptively Transferred T-cells with Drug-loaded Nanoparticles for Cancer Immunotherapy," BMES. Presentation MIT, Oct. 27, 2012, 18 pages.
Zhu et al., "Stabilization of proteins encapsulated in injectable poly (lactide-co-glycolide)," Nat Biotechnol. vol. 18(1):52-57 (1999).
Alving, Lipopolysaccharide, lipid A, and liposomes containing lipid A as immunologic adjuvants. Immunobiology. Apr. 1993; 187(3-5):430-46.
Edwards, B. et al., "The Remarkable Flexibility of the Human Antibody Repertoire Isolation of Over One Thousand Different Antibodies to a Single Protein, BLyS," J Mol Biol., vol. 334(1):103-118 (2003).
European Search Report, European Application No. 16836005.5, dated Jun. 19, 2019, 14 pages.
Fahmy et al., A nanoscopic multivalent antigen-presenting carrier for sensitive detection and drug delivery to T cells. Nanomedicine. Mar. 2007;3(1):75-85.
Han, K-P., et al., "IL-15:IL-15 receptor alpha superagonist complex: High-level co-expression in recombinant mammalian cells, purification and characterization," Cytokine, vol. 56(3):804-810 (2011).
Lloyd, C. et al., "Modelling the human immune response: performance of a 10" human antibody repertoire against a broad panel of therapeutically relevant antigens," Protein Engineering, Design & Selection, vol. 22(3):159-168 (2009).
O'Hagan et al., Microparticles as vaccine adjuvants and delivery systems. Expert Rev Vaccines. Apr. 2003;2(2):269-83.
Shimizu, T. et al., "Nanogel DDS enables sustained release of IL-12 for tumor immunotherapy," BBRC, vol. 367(2):330-335 (2008.

Singh et al., Cationic microparticles: A potent delivery system for DNA vaccines. Proc Natl Acad Sci USA. Jan. 18, 2000;97(2):811-6.
Akagi et al., "Development of vaccine adjuvants using polymeric nanoparticles and their potential applications for anti-HIV vaccine," Yakugaku Zasshi, 127(2):307-317 (2007).
Akin et al., "Bacteria-mediated delivery of nanoparticles and cargo into cells," Nat Nanotechnol., vol. 7:441-449 (2007).
Allen, T. et al., "Anti-CD19-Targeted Liposomal Doxorubicin Improves the Therapeutic Efficacy in Murine B-Cell Lymphoma and Ameliorates the Toxicity of Liposomes with Varying Drug Release Rates," Clin Cancer Res., vol. 11(9):3567-3573 (2005).
Allen, T. et al., "Drug Delivery Systems: Entering the Mainstream," Science, vol. 303(5665): 1818-1822 (2004).
Alving, C., "Liposomes as carriers of antigens and adjuvants," J Immunol Methods. vol. 40(1):1-13 (1991).
Babensee, J. et al., "Differential levels of dendritic cell maturation on different biomaterials used in combination products," J Biomed Mater Res., vol. 74(4):503-510. (2005).
Bal et al., "Efficient induction of immune responses through intradermal vaccination with N-trimethyl chitosan containing antigen formulations," J Control Release, vol. 142(3):374-383 (2010).
Barral, P. et al., "B cell receptor-mediated uptake of CD1d-restricted antigen augments antibody responses by recruiting invariant NKT cell help in vivo," Proc Natl Acad Sci USA, vol. 105(24):8345-8350 (2008).
Baudino et al., "Crucial role of aspartic acid at position 265 in the CH2 domain for murine IgG2a and IgG2b Fc-associated effector functions," J Immunol., vol. 181(9):6664-6669 (2008).
Beisiegel, U. et al., "The LDL-receptor-related protein, LRP, is an apolipoprotein E-binding protein," Nature, vol. 341:162-164 (1989).
Bennewitz, N. et al., "The effect of the physical form of poly(lactic-co-glycolic acid) carriers on the humoral immune response to co-delivered antigen," Biomaterials, vol. (16):2991-2999 (2005).
Bershteyn et al., "Versatile lipid-based vaccine carriers elicit CTL and antibody responses to surface-conjugated or encapsulated antigen," Keystone Symposium, Abstract, 1 page (2010).
Bershteyn et al., Versatile lipid-based vaccine carriers elicit CTL and antibody responses to surface-conjugated or encapsulated antigen. Keystone Symposium. Poster Presentation. 2010. 1 page.
Bershteyn, A. et al., "Polymer-supported lipid shells, onions, and flowers," Soft Matter, vol. 4(9):1787-1791 (2008).
Bershteyn, A.et al. "Lipid-Coated Nano-and Microparticles for Vaccine Design," Materials Research Society fall meeting, 7 pages (2009).
Bershteyn, A.et al., "Robust IgG responses to nanograms of antigen using a biomimetic lipid-coated particle vaccine," J Control Release, vol. 157(3):354-65 (2012).
Besser, M. et al., "Clinical Responses in a Phase II Study Using Adoptive Transfer of Short-term Cultured Tumor in Filtration Lymphocytes in Metastatic Melanoma Patients," Clin Cancer Res., vol. 16(9):2646-2655 (2010).
Bhowmick, S. et al., "Comparison of liposome based antigen delivery systems for protection against Leishmania donovani," J Controlled Release, vol. 141(2):199-207 (2010).
Bottini, "Luminescent Silica Nanobeads: Characterization and Evaluation as Efficient Cytoplasmatic Transporters for T-Lymphocytes," JACS, vol. 129(25) pp. 7814-7823 (2007).
Brocchini, et al. "Disulfide bridge based PEGylation of proteins", Advanced Drug Delivery Reviews, vol. 60:3-12 (2008).
Cai, Z. et al., "Encapsulated enhanced green fluorescence protein in silica nanoparticle for cellular imaging," Nanoscale. vol. 3(5):1974-1976 (2011).
Cashion, M. et al., "Biomimetic Design and Performance of Polymerizable Lipids," Accounts Chem. Res., vol. 42(8):1016-1025 (2009).
Chacon, M. et al., "Optimized preparation of poly d,I (lactic-glycolic) microspheres and nanoparticles for oral administration," Int J Pharm., vol. 141(1-2):81-91 (1996).
Chambers, E. et al., "Long Circulating Nanoparticles via Adhesion on Red Blood Cells: Mechanism and Extended Circulation," Exp Biol Med (Maywood), vol. 232(7):958-966 (2007).
Chambers, E. et al., "Prolonged circulation of large polymeric nanoparticles by non-covalent adsorption on erythrocytes," J Control Release, vol. 100(1): 111-119 (2004).

(56) References Cited

OTHER PUBLICATIONS

Chen, L. et al., "Characterization of PLGA microspheres for the controlled delivery of IL-1a for tumor immunotherapy," J Controlled Rel., vol. 43:261-272 (1997).
Chirifu et al., "Crystal structure of the IL-15-IL-15Ralpha complex, a cytokine-receptor unit presented in trans", Nature Immunology, Published online Jul. 22, 2007, pp. 1001-1007 (2007).
Cho et al., "Understanding the Role of Surface Charges in Cellular Adsorption versus In-ternalization by Selectively Removing Gold Nanoparticles on the Cell Surface with a 1-2/KI Etchant," Nano Lett., 9(3):1080-1084 (2009).
Clemente-Casares et al., Peptide-MHC-based nanovaccines for the treatment of; autoimmunity: a "one size fits all" approach? J Mol Med (Bed). Aug. 2011;89(8):733-42. doi:; 1O.1007/s00I09-011-0757-z. Epub Apr. 16, 2011.
Cole, C. et al., "Tumor-targeted, systemic delivery of therapeutic viral vectors using hitchhiking on antigen-specific T cells," Nat Med., vol. 11(10):1073-1081 (2005).
Collins, D. et al., "Processing of exogenous liposome-encapsulated antigens in vivo generates class I MHC-restricted T cell responses," J Immunol., vol. 148(11):3336-3341 (1992).
Coronoa-Ortega, T. et al., "Characterization of cationic liposomes having IL-2 expressed on their external surface, and their affinity to cervical cancer cells expressing the IL-2 receptor," Journal of Drug Targeting, vol. 17(7):496-501 (2009).
Davis, M. et al., "Nanoparticle therapeutics: an emerging treatment modality for cancer," Nat Rev Drug Discov., vol. 7(9):771-782 (2008).
De La Pena, H. et al., "Artificial exosomes as tools for basic and clinical immunology," J Immunol. Methods, vol. 344(2):121-132. (2009).
Demento, S. et al., "Inflammasome-activating nanoparticles as modular systems for optimizing vaccine efficacy," Vaccine, vol. 27(23):3013-3021 (2009).
Dinauer, N. et al., "Selective targeting of antibody-conjugated nanoparticles to leukemic cells and primary T-lymphocytes," Biomaterials, vol. 26(29):5898-5906 (2005).
Ding, H. et al., "Bioconjugated PLGA-4-arm-PEG branched polymeric nanoparticles as novel tumor targeting; carriers," Nanotechnology, vol. 22(16): 12 pages (2011).
Diwan et al., "Dose sparing of CpG oligodeoxynucleotide vaccine adjuvants by nanoparticle delivery," Curr Drug Deliv., vol. 1(4):405-412 (2004).
Dou, H. et al., "Development of a macrophage-based nanoparticle platform for antiretroviral drug delivery," Blood., vol. 108(8):2827-2835 (2006).
Drummond, D. et al., "Optimizing Liposomes for Delivery of Chemotherapeutic Agents to solid tumors," Pharmacol Rev., vol. 51(4):691-743 (1991).
Dubikovskaya, E. et al., Overcoming multidrug resistance of small-molecule therapeutics through conjugation with releasable octaarginine transporters, PNAS, vol. 105(34):12128-12133 (2008).
Dudley, M. et al., "A phase I Study of Nonmyeloablative Chemotherapy and Adoptive Transfer of Autologous Tumor Antigen-specific T lymphocytes in patients with Metastatic Melanoma," J Immunother., vol. 25(3):243-251 (2002).
Dudley, M. et al., "Cancer Regression and Autoimmunity in Patients after Clonal Repopulation with Antitumor Lymphocytes," Science, vol. 298(5594):850-854 (2002).
Eck, W. et al., "Anti-CD4-targeted gold nanoparticles induce specific contrast enhancement of peripheral lymph nodes in X-ray computed tomography of live mice," Nano Lett. vol. 10(7):2318-2322 (2010).
Elamanchili, P. et al., "Characterization of poly(D,L-lactic-co-glycolic acid) based nanoparticulate system for enhanced delivery of antigens to dendritic cells," Vaccine, vol. 22(19):2406-2412 (2004).
Endsley, A. et al., "Enhanced anti-HIV Efficacy of Indinavir after inclusion in CD4-targeted lipid nanoparticles," J Acquir Immune Defic Syndr., vol. 61(4):417-424 (2012).

European Search Report, EP 09827900, dated Aug. 17, 2015, pp. 1-3.
Extended European Search Report, EP Application No. 14813855, dated Jan. 27, 2017, 7 pages.
Fahmy, T. et al., "A nanoscopic multivalent antigen-presenting carrier for sensitive detection and drug delivery to T cells," Nanomedicine, vol. 3(1):75-85 (2007).
Fahmy, T. et al., "Nanosystems for simultaneous imaging and drug delivery to T cells," AAPS J., vol. 9(2):E171-E180 (2007).
U.S. Appl. No. 17/069,305, filed Oct. 13, 2020, Darrell J. Irvine.
U.S. Appl. No. 15/625,479, filed Jun. 16, 2017, Darrell J. Irvine.
U.S. Appl. No. 15/015,464, filed Feb. 4, 2016, Darrell J. Irvine.
U.S. Appl. No. 13/130,845, filed Aug. 16, 2011, Darrell J. Irvine.
U.S. Appl. No. 13/910,937, filed Jun. 5, 2013, Darrell J. Irvine.
U.S. Appl. No. 12/456,592, filed Jun. 17, 2009, Darrell J. Irvine.
U.S. Appl. No. 12/456,587, filed Jun. 17, 2009, Darrell J. Irvine.
U.S. Appl. No. 13/053,101, filed Mar. 21, 2011, Darrell J. Irvine.
U.S. Appl. No. 13/052,067, filed Mar. 19, 2011, Darrell J. Irvine.
U.S. Appl. No. 13/400,076, filed Feb. 19, 2012, Darrell J. Irvine.
U.S. Appl. No. 14/581,004, filed Dec. 23, 2014, Darrell J. Irvine.
U.S. Appl. No. 14/265,924, filed Apr. 30, 2014, Darrell J. Irvine.
U.S. Appl. No. 14/741,694, filed Jun. 17, 2015, Darrell J. Irvine.
U.S. Appl. No. 15/230,736, filed Aug. 8, 2016, Darrell J. Irvine.
U.S. Appl. No. 15/097,607, filed Apr. 13, 2016, Darrell J. Irvine.
U.S. Appl. No. 15/452,992, filed Mar. 8, 2017, Darrell J. Irvine.
U.S. Appl. No. 15/884,143, filed Jan. 30, 2018, Darrell J. Irvine.
U.S. Appl. No. 15/673,126, filed Aug. 9, 2017, Darrell J. Irvine.
U.S. Appl. No. 14/309,513, filed Jun. 19, 2014, Darrell J. Irvine.
U.S. Appl. No. 15/195,571, filed Jun. 28, 2016, Darrell J. Irvine.
U.S. Appl. No. 14/498,386, filed Sep. 26, 2014, Li Tang.
U.S. Appl. No. 15/470,169, filed Mar. 27, 2017, Li Tang.
U.S. Appl. No. 16/195,128, filed Nov. 19, 2018, Li Tang.
U.S. Appl. No. 16/795,286, filed Feb. 19, 2020, Li Tang.
U.S. Appl. No. 16/451,996, filed Jun. 25, 2019, Li Tang.
U.S. Appl. No. 15/236,186, filed Aug. 12, 2016, Darrell J. Irvine.
U.S. Appl. No. 15/625,479, Jul. 13, 2020.
U.S. Appl. No. 15/625,479, Dec. 2, 2019.
U.S. Appl. No. 15/625,479, May 14, 2019.
U.S. Appl. No. 15/625,479, Feb. 13, 2019.
U.S. Appl. No. 15/625,479, Jan. 7, 2019.
U.S. Appl. No. 15/625,479, Jun. 18, 2018.
U.S. Appl. No. 15/625,479, Jan. 26, 2018.
U.S. Appl. No. 15/015,464, Jan. 19, 2017.
U.S. Appl. No. 13/130,845, Feb. 11, 2016.
U.S. Appl. No. 13/130,845, Jan. 26, 2016.
U.S. Appl. No. 13/130,845, Nov. 6, 2015.
U.S. Appl. No. 13/130,845, Jun. 25, 2015.
U.S. Appl. No. 13/130,845, Jan. 13, 2015.
U.S. Appl. No. 13/130,845, Sep. 11, 2013.
U.S. Appl. No. 13/130,845, Feb. 26, 2013.
U.S. Appl. No. 13/130,845, Oct. 22, 2012.
U.S. Appl. No. 13/910,937, Jun. 22, 2016.
U.S. Appl. No. 13/910,937, Mar. 1, 2016.
U.S. Appl. No. 13/910,937, Jul. 15, 2015.
U.S. Appl. No. 13/910,937, Apr. 27, 2015.
U.S. Appl. No. 12/456,592, Jun. 20, 2014.
U.S. Appl. No. 12/456,592, Apr. 11, 2012.
U.S. Appl. No. 12/456,592, Aug. 2, 2011.
U.S. Appl. No. 12/456,592, Jan. 12, 2011.
U.S. Appl. No. 12/456,587, Mar. 26, 2013.
U.S. Appl. No. 12/456,587, Oct. 10, 2012.
U.S. Appl. No. 12/456,587, Jul. 28, 2011.
U.S. Appl. No. 12/456,587, Nov. 12, 2010.
U.S. Appl. No. 12/456,587, Jul. 28, 2010.
U.S. Appl. No. 13/053,101, Jul. 2, 2013.
U.S. Appl. No. 13/053,101, Jun. 20, 2013.
U.S. Appl. No. 13/053,101, May 9, 2013.
U.S. Appl. No. 13/052,067, Apr. 25, 2014.
U.S. Appl. No. 13/052,067, Jan. 27, 2014.
U.S. Appl. No. 13/052,067, Jun. 6, 2013.
U.S. Appl. No. 13/052,067, Oct. 26, 2012.
U.S. Appl. No. 13/052,067, May 16, 2012.
U.S. Appl. No. 13/052,067, Mar. 13, 2012.

(56) References Cited

OTHER PUBLICATIONS

U.S. Appl. No. 13/400,076, Apr. 15, 2015.
U.S. Appl. No. 13/400,076, Oct. 23, 2014.
U.S. Appl. No. 13/400,076, Apr. 10, 2014.
U.S. Appl. No. 13/400,076, Aug. 20, 2013.
U.S. Appl. No. 13/400,076, Apr. 24, 2013.
U.S. Appl. No. 13/400,076, Aug. 23, 2012.
U.S. Appl. No. 13/400,076, Jun. 21, 2012.
U.S. Appl. No. 14/581,004, Jan. 14, 2016.
U.S. Appl. No. 14/581,004, Jul. 27, 2015.
U.S. Appl. No. 14/741,694, May 9, 2016.
U.S. Appl. No. 14/741,694, Dec. 16, 2015.
U.S. Appl. No. 14/265,924, Oct. 2, 2014.
U.S. Appl. No. 14/309,513, Sep. 11, 2015.
U.S. Appl. No. 14/498,386, Feb. 14, 2017.
U.S. Appl. No. 14/498,386, Dec. 16, 2016.
U.S. Appl. No. 14/498,386, Nov. 8, 2016.
U.S. Appl. No. 14/498,386, Jun. 27, 2016.
U.S. Appl. No. 14/498,386, Nov. 5, 2015.
U.S. Appl. No. 14/498,386, Jun. 24, 2015.
U.S. Appl. No. 15/230,736, May 4, 2017.
U.S. Appl. No. 15/230,736, Dec. 9, 2016.
U.S. Appl. No. 15/452,992, Oct. 25, 2017.
U.S. Appl. No. 15/452,992, Jul. 6, 2017.
U.S. Appl. No. 15/097,607, Dec. 21, 2016.
U.S. Appl. No. 15/097,607, Nov. 25, 2016.
U.S. Appl. No. 15/097,607, Aug. 5, 2016.
U.S. Appl. No. 15/673,126, Jun. 22, 2018.
U.S. Appl. No. 15/470,169, Oct. 17, 2018.
U.S. Appl. No. 15/470,169, Jun. 6, 2018.
U.S. Appl. No. 15/236,186, Nov. 22, 2019.
U.S. Appl. No. 15/236,186, Apr. 17, 2019.
U.S. Appl. No. 15/236,186, Jun. 18, 2018.
U.S. Appl. No. 15/195,571, May 10, 2021.
U.S. Appl. No. 15/195,571, Aug. 19, 2020.
U.S. Appl. No. 15/195,571, Dec. 27, 2019.
U.S. Appl. No. 15/195,571, Aug. 30, 2019.
U.S. Appl. No. 15/195,571, Nov. 28, 2018.
U.S. Appl. No. 15/195,571, May 29, 2018.
U.S. Appl. No. 16/195,128, Apr. 9, 2019.
U.S. Appl. No. 16/195,128, Jan. 18, 2019.
U.S. Appl. No. 16/451,996, Jan. 15, 2020.
U.S. Appl. No. 16/451,996, Oct. 28, 2019.
Fifis, T. et al., "Size-Dependent Immunogenicity: Therapeutic and protective properties of nano-vaccines against tumors," J Immunol., vol. 173(5):3148-3154 (2004).
Fischer, H. et al., "Nanotoxicity: the growing need for in vivo study," Current Opin Biotechnol., vol. 18(6):565-571 (2007).
Friede, M. et al., "Induction of immune response against a short synthetic peptide antigen coupled to small neutral liposomes containing monophosphoryl lipid A," Mol Immunol., vol. 30(6):539-547 (1993).
Gabizon, A. et al., "Prolonged circulation time and enhanced accumulation in malignant exudates of doxorubicin encapsulated in polyethylene-glycol coated liposomes," Cancer Res., vol. 54(4):987-992 (1994).
Gao, W. et al., "Treg versus Th17 lymphocyte lineages are cross-regulated by LIF versus IL-6," Cell Cycle, vol. 8(9):1444-1450 (2009).
Gao, X. et al., "Lectin-conjugated PEG-PLA nanoparticles: preparation and brain delivery after intranasal administration," Biomaterials, vol. 27(18):3482-3490 (2006).
Garinot, M. et al., "PEGylated PLGA-based nanoparticles targeting M cells for oral vaccination," J Control Release, vol. 120(3):195-204 (2007).
Green, J. et al., "Combinatorial Modification of Degradable Polymers Enables Transfection of Human Cells Comparable to Adenovirus," Advanced Materials, vol. 19(19):2836-2842 (2007).
Gregoriadis, G. et al., "Liposomes as immunological adjuvants and vaccine carriers," J Control Release, vol. 41(1-2):49-56 (1996).
Gunn, J. et al., "A Multimodal Targeting Nanoparticle for Selectively Labeling T Cells," SMALL, vol. 4(6):712-715 (2008).
Hamdy, S. et al., "Enhanced antigen-specific primary CD4+ and CD8+ responses by codelivery of ovalbumin and toll-like receptor ligand monophosphoryl lipid A in poly(D,L-lactic-co-glycolic acid) nanoparticles," J Biomed Mater Res A., vol. 81(3):652-662 (2006).
Hedge, M. et al., "Tandem CAR T cells targeting HER2 and IL13Ra2 mitigate tumor antigen escape," J Clin Invest., vol. 126(8):3036-3052 (2016).
Heffernan, M. et al., "The stimulation of CD8+ T cells by dendritic cells pulsed with polyketal microparticles containing ion-paired protein antigen and poly(inosinic acid)-poly(cytidylic acid)," Biomaterials, vol. 30(5):910-918 (2009).
Heit et al., "Antigen co-encapsulated with adjuvants efficiently drive protective T cell immunity," Eur J Immunol., vol. 37(8):2063-74 (2007).
Hodi, F. et al., "Improved survival with ipilimumab in Patients with Metastatic Melanoma," N Engl. J. Med., vol. 363(8):711-723 (2010).
Hori, Y. et al., "Injectable dendritic cell-carrying alginate gels for immunization and immunotherapy," Biomaterials, vol. 29(27):3671-3682 (2008).
Hori, Y. et al., "Engulfing Tumors with Synthetic Extracellular Matrices for Cancer Immunotherapy," Biomaterials, vol. 30(35):6757-6767 (2009).
Hotz, J. et al., "Vesicle-templated polymer hollow spheres," Langmuir, vol. 14(5): 1031-1036 (1998).
Hsu, C. et al., "Cytokine-independent growth and clonal expansion of a primary human CD8+ T-cell clone following retroviral transduction with the IL-15 gene," Blood, vol. 109(12):5168-5177 (2007).
Hu et al., "Cytosolic delivery of membrane-impermeable molecules in dendritic cells using pH-responsive core-shell nanoparticles," Nano Lett. vol. 7(10): 3056-3064 (2007).
Immordino, M. et al., "Stealth liposomes: review of the basic science, rationale, and clinical applications, existing and potential," Int J Nanomedicine, vol. 1(3):297-315 (2006).
International Preliminary Report on Patentability, PCT/US2009/006290, dated May 24, 2011, 7 pages.
International Preliminary Report on Patentability, PCT/US2014/042004, dated Dec. 22, 2015, 8 pages.
International Preliminary Report on Patentability, PCT/US2014/057789, dated Mar. 29, 2016, 12 pages.
International Preliminary Report on Patentability, PCT/US2016/046891, dated Feb. 13, 2018, 6 pages.
International Search Report and Written Opinion for Application No. PCT/US2016/046891, 8 pages, dated Oct. 31, 2016.
International Search Report and Written Opinion, PCT/US2009/006290, dated Aug. 17, 2010, 10 pages.
International Search Report and Written Opinion, PCT/US2014/042004, dated Nov. 3, 2014, 10 pages.
International Search Report and Written Opinion, PCT/US2014/057789, dated Jan. 6, 2015, 17 pages.
Irvine, D.J. "Engineering nanomaterials as vaccine adjuvants and agents for cancer immunotherapy," Seminar at Scripps Res Institute, Apr. 28, 2011, 57 slides.
Irvine, D.J. "Engineering nanoparticle delivery for vaccines and immunotherapy," Nanotechnology in Infectious Disease Meeting, Atlanta, GA., 33 pages (2010).
Irvine, D.J. et al., "Combining cell therapy with nanotechnology for enhanced cancer immunotherapy," 16th International Symposium on Recent Advances in Drug Delivery Systems, Salt Lake City, UT., Feb. 3-6, Abstract, 2 pages (2013).
Jain, N. et al., "Targeted drug delivery to macrophages," Expert Opin Drug Deliv., vol. 10(3):353-367 (2013).
Jeong, J. et al., "Enhanced adjuvantic property of polymerized liposome as compared to a phospholipid liposome," J Biotechnol., vol. 94(3):255-263 (2002).
Jiang, W. et al., "Biodegradable poly(lactic-co-glycolic acid) microparticles for injectable delivery of vaccine antigens," Adv Drug Deliv Rev., vol. 57(3):391-410 (2005).
Johnson, RM., "The kinetics of Resealing of Washed Erythricyte Ghosts," J. Membr. Biol., vol. 22 (3-4):231-251 (1975).

(56) References Cited

OTHER PUBLICATIONS

Jones, DT "Critically assessing the state-of-the-art in protein structure prediction," The Pharmacogenomics Journal, vol. 1(2):126-134 (2001).
Jones, L. et al., "Releasable Luciferin-Transporter Conjugates: Tools for the Real-time Analysis of Cellular Uptake and Release," J Am Chem Soc., vol. 128(20):6526-6527 (2006).
June, C. "Principles of adoptive T cell cancer therapy," J Clin Invest., vol. 117(5):1204-1212 (2007).
Kaiser-Schulz, G. et al., "Polylactide-coglycolide microspheres co-encapsulating recombinant tandem prion protein with CpG-oligonucleotide break self-tolerance to prion protein in wild-type mice and induce CD4 and CD8 T cell responses," J Immunol., vol. 179(5):2797-2807 (2007).
Kalos, M. "Biomarkers in T cell therapy clinical trials," J Trans Med., vol. 9(138) 9 pages (2011).
Kalos, M. et al., "T cells with chimeric antigen receptors have potent antitumor effects and can establish memory in patients with advanced leukemia," Sci Trans Med., vol. 3(95), 12 pages (2007).
Kerkar, S. et al., "Tumor-specific CD8+ T cells expressing interleukin-12 eradicate established cancers in lymphodepleted hosts," Cancer Res., vol. 70(17):6725-6734 (2010).
Kirby, C. et al., "Dehydration-rehydration vesicles: a simple method for high yield drug entrapment in liposomes," Nat Biotechnol., vol. 2(11):979-984 (1984).
Kirpotin, D. et al., "Antibody targeting of long-circulating lipidic nanoparticles does not increase tumor localization but does increase internalization in animal models," Cancer Res., vol. 66(13):6732-6740 (2006).
Klebanoff, C. et al., "Sinks, suppressors and antigen presenters: how lymphodepletion enhances T cell-mediated tumor immunotherapy," Trends Immunol., vol. 26(2): 111-117 (2005).
Kobayashi, H. et al., "Phase I/II study of adoptive transfer of γδ T cells in combination with zoledronic acid and IL-2 to patients with advanced renal cell carcinoma," Cancer Immunol. Immunother, vol. 60(8):1075-1084 (2011).
Kochenderfer, J. et al., "Adoptive transfer of syngeneic T cells transduced with a chimeric antigen receptor that recognizes murine CD19 can eradicate lymphoma and normal B cells," Blood, vol. 116 (19): 3875-3886 (2010).
Konigsberg, P.J. "The development of IL-2 conjugated liposomes for therapeutic purposes," Biochimica Biophysica Acta, vol. 1370(2):243-251 (1998).
Konrad, M. et al., "Pharmacokinetics of recombinant interleukin 2 in humans," Cancer Res., vol. 50(7):2009-2017 (1990).
Perche, F. et al., "Recent trends in multifunctional liposomal nanocarriers for enhanced tumor targeting," J Drug Deliv. Article ID. 705265, 32 pages (2013).
Perica, K. et al., "Magnetic field-induced T cell receptor clustering by nanoparticles enhances T cell activation and stimulates antitumor activity," ACS Nano., vol. 8(3):2252-2260 (2013).
Petros, R. et al., "Strategies in the design of nanoparticles for therapeutic applications," Na-ture Reviews, vol. 9:615-627 (2010).
Phillips, N.et al., "Immunoliposome targeting to murine CD4+ leucocytes is dependent on immune status," J Immunol., vol. 152(6):3168-3174 (1993).
Plunkett, K. et al., "Chymotrypsin Responsive Hydrogel: Application of a Disulfide Exchange Protocol for the Preparation of Methacrylamide Containing Peptides," Biomacromolecules, vol. 6(2): 632-637 (2005).
Popescu, M. et al., "A novel proteoliposomal vaccine elicits potent antitumor immunity in mice," Blood, vol. 109(12):5407-5410 (2007).
Press et al., "Retention of B-Cell-Specific Monoclonal Antibodies by Human Lymphoma Cells," Blood, 83(5):1390-1397 (1994).
Prieto, P. et al., "Enrichment of CD8+ cells from melanoma tumor-infiltrating lymphocyte cultures reveals tumor reactivity for use in adoptive cell therapy," J Immunother., vol. 33(5):547-556 (2010).

Prokop, A. et al., "Hydrogel-based colloidal polymeric system for protein and drug delivery: physical and chemical characterization, permeability control and applications," Advances in Polymer Science, vol. 160:119-173 (2002).
Puri, A. et al., "HER2-specific affibody-conjugated thermosensitive liposomes (Affisomes) for improved delivery of anticancer agents," J Liposome Res., vol. 18(4):293-307 (2008).
Qiao, J. et al., "Purging metastases in lymphoid organs using a combination of antigen-nonspecific adoptive T cell therapy, oncolytic virotherapy and immunotherapy," Nat Med, vol. 14(1):37-44 (2008).
Rangel-Corona, R. et al., "Cationic liposomes bearing IL-2 on their external surface induced mice leukocytes to kill human cervical cancer cells in vitro, and significantly reduced tumor burden in immunodepressed mice," J Drug Target. vol. 19(2):79-85 (2011).
Reddy, R. et al., "In vivo cytotoxic T lymphocyte induction with soluble proteins administered in liposomes," J Immunol. vol. 148(5):1585-1589 (1992).
Reddy, S. et al., "Exploiting lymphatic transport and complement activation in nanoparticle vaccines," Nature Biotechnology, vol. 25(10):1159-1164 (2007).
Reed, S. et al., "New horizons in adjuvants for vaccine development," Trends Immunol., vol. 30(1):23-32 (2009).
Restifo, N. et al., "Adoptive immunotherapy for cancer: harnessing the T cell response," Nat Rev. Immunol., vol. 12(4):269-281 (2012).
Ring, A. et al., "Mechanistic and structural insight into the functional dichotomy between IL-2 and IL-15," Nature, mmunology, vol. 12(13):1187-1197 (2012).
Rosenberg, S. et al., "Adoptive cell transfer: a clinical path to effective cancer immunotherapy," Nat Rev Cancer, vol. 8(4):299-308 (2008).
Rubin, B. et al., "Fractionation of T cell subsets on Ig anti-Ig columns: Isolation of helper T cells from nonresponder mice, demonstration of antigen-specific T suppressor cells, and selection of CD-3 negative variants of Jurkat T cells," Cellular Immunology, vol. 119(2):327-340. (1989).
Rubinstein, M. et al., "Converting IL-15 to a superagonist by binding to soluble IL-15R{alpha}," Proc Natl Acad Sci USA., vol. 103(24):9166-9171 (2006).
Rubinstein, M. et al., "Ex vivo interleukin-12-priming during CD8( +) T cell activation dramatically improves adoptive T cell transfer antitumor efficacy in a lymphodepleted host," J Am Coll Surg., vol. 24(4):700-707 (2012).
Sahaf, B. et al., "Lymphocyte surface thiol levels," Proc Natl Acad Sci USA., vol. 100(7):4001-4005 (2003).
Schlosser et al., "TLR ligands and antigen need to be coencapsulated into the same biodegradable microsphere for the generation of potent cytotoxic T lymphocyte responses," Vaccine, vol. 26(13):1626-1637 (2008).
Scott, E. et al., "Protein adsorption and cell adhesion on nanoscale bioactive coatings formed from poly(ethylene glycol) and albumin microgels," Biomaterials, vol. 29(34):4481-4493 (2008).
Seeman, P. et al., "Transient Holes in the Erythrocyte Membrane During Hypotonic Hemolysis and Stable Holes in the Membrane After Lysis By Saponin and Lysolecithin," The Rockefeller University, J Cell Biol. vol. 32(1): 55-70 (1967).
Shi et al., "Dendrimer-functionalized shell-crosslinked iron oxide nanoparticles for in-vivo magnetic resonance imaging of tumors.," Advanced Materials, vol. 20(9): 1671-1678 (2008).
Shilyansky, J. et al., "T-cell receptor usage by melanoma-specific clonal and highly oligoclonal tumor-infiltrating lymphocyte lines," PNAS, vol. 91: 2829-2833 (1994).
Singh et al., "Anionic microparticles are a potent delivery system for recombinant antigens from Neisseria meningitidis serotype B," J Pharm Sci., vol. 93(2):273-282 (2003).
Singh et al., "Cationic microparticles are an effective delivery system for immune stimulatory cpG DNA," Pharm Res., vol. 18(10):1476-1479 (2001).
Singh et al., "Charged polylactide co-glycolide microparticles as antigen delivery systems," Expert Opin Biol Ther., vol. 4(4):483-491 (2004).
Singh et al., "Immunogenicity and protection in small-animal models with controlled-release tetanus toxoid microparticles as a single-dose vaccine," Infect Immun., vol. 65(5):1716-17121 (2001).

(56) References Cited

OTHER PUBLICATIONS

Singh et al., "Nanoparticles and microparticles as vaccine-delivery systems," Expert Rev Vaccines. vol. 6(5):797-808 (2007).

Singh et al., "Polylactide-co-glycolide microparticles with surface adsorbed antigens as vaccine delivery systems," Curr Drug Deliv., vol. 3(1):115-120 (2006).

Singh et al., "Recent advances in vaccine adjuvants," Pharm Res., vol. 19(6):715-728 (2002).

Singh, S. et al., "Embedding of Active Proteins and Living Cells in Redox-Sensitive Hydro-gels and Nanogels through Enzymatic Cross-Linking," Angew. Chem. tnt. Ed., vol. 52: 3000-3003 (2013).

Society for Experimental Biology and Medicine, Nanoparticles hitchhike on red blood cells for drug delivery. RxPG News. Jun. 27, 2007. Last retrieved from http://www.rxpgnews.com/drugdelivery/Nanoparticles-hitchhike-on-red-blood-cells-a-potential-new-method-for-drug-delivery_40324.shtml on Nov. 8, 2012.

Steers, N. et al., "Liposome-encapsulated HIV-1 Gag p24 containing lipid A induces effector CD4+ T-cells, memory CD8+ T-cells, and pro-inflammatory cytokines," Vaccine, vol. 27(49):6939-6949 (2009).

Steinfeld, U., et al., "T lymphocytes as potential therapeutic drug carrier for cancer treatment," Int. J. Pharm., vol. 311:229-236 (2006).

Stephan et al., "Enhancing Cell therapies from the Outside In: Cell Surface Engineering Using Synthetic Nanomaterials," Nano Today., vol. 6(3):309-325 (2011).

Stephan et al., "Synapse-directed delivery of immunomodulators using T-cell-conjugated nanoparticles," Biomaterials, vol. 33(23):5776-5787 (2012).

Stephan et al., "T cell-encoded CD80 and 4-1BBL induce auto-and transcostimulation, resulting in potent tumor rejection," Nat Med., vol. 13(12): 1440-1449 (2007).

Stephan, M. et al., "Therapeutic cell engineering with surface-conjugated synthetic nanoparticles," Nat Med., vol. 16(9):1035-1041 (2010).

Supplementary European Search Report, EP Application No. 09827900.3, dated Sep. 10, 2015, 7 pages.

Swiston et al., "Surface functionalization of living cells with multilayer patches," Nano Lett., vol. 8(12):4446-4453 (2008).

Takasaki et al., "Micelles as intermediates in the preparation of protein-liposome conjugates," Bioconjug Chem., vol. 17(2):438-450 (2006).

Tan et al., "PEG-urokinase nanogels with enhanced stability and controllable bioactivity," Soft Matter, vol. 8:2644-2650 (2012).

Tang, L et al., "Abstract 2792: Engineering T lymphocytes with protein nanogels for cancer immunotherapy," Cancer Research, AACR Annual Meeting 2014, Apr. 5-9, 2014, 2 pages.

Tang, L. et al., "Enhancing T cell therapy through TCR-signaling-responsive nanoparticle drug delivery," Nature Biotechnology, Jul. 9, 2018 (Jul. 9, 2018), XP055564253, New York ISSN: 1087-0156, DOI: 10.1038/nbt.4181.

Tangney, M. et al., "The use of Listeria monocytogenes as a DNA delivery vector for cancer gene therapy," Bioeng Bugs., vol. 1 (4):284-287 (2010).

Topalian et al., Safety, activity, and immune correlates of anti-PD-I antibody in cancer. N Engl; J Med. Jun. 28, 2012;366(26):2443-54. doi: 10.1056INEJMoa1200690. Epub Jun. 2, 2012.

English Translation of JP Office Action, JP Appln. No. 2020-109309, dated Sep. 7, 2021, 3 pages.

Igaku-no-Ayumi, 2013, 244(9), 831-836, No English Translation available, cited in corresponding JP Office Action, JP Appln. No. 2020-109309, dated Sep. 7, 2021, 3 pages cited herein.

Kagaku-to-Seibutsu, 1990, 28(1), 62-66, No English Translation available, cited in corresponding JP Office Action, JP Appln. No. 2020-109309, dated Sep. 7, 2021, 3 pages cited herein.

SEQUENCE LISTING

```
<160> NUMBER OF SEQ ID NOS: 9

<210> SEQ ID NO 1
<211> LENGTH: 114
<212> TYPE: PRT
<213> ORGANISM: Homo sapiens
<220> FEATURE:
<221> NAME/KEY: misc_feature
<222> LOCATION: (1)..(114)
<223> OTHER INFORMATION: Human IL-15 (N72D mutant)

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
```

```
                    20                  25                  30
Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
             50                  55                  60

Asn Leu Ile Ile Leu Ala Asn Asp Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 2
<211> LENGTH: 297
<212> TYPE: PRT
<213> ORGANISM: Homo sapiens
<220> FEATURE:
<221> NAME/KEY: misc_feature
<222> LOCATION: (1)..(297)
<223> OTHER INFORMATION: Human IL-15R-alpha-Su/Fc  (IgG1 CH2-CH3 (Fc
      domain))

<400> SEQUENCE: 2

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
         50                  55                  60

Arg Glu Pro Lys Ser Cys Asp Lys Thr His Thr Cys Pro Pro Cys Pro
 65                  70                  75                  80

Ala Pro Glu Leu Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
                100                 105                 110

Val Val Asp Val Ser His Glu Asp Pro Glu Val Lys Phe Asn Trp Tyr
             115                 120                 125

Val Asp Gly Val Glu Val His Asn Ala Lys Thr Lys Pro Arg Glu Glu
         130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Asp Glu Leu
            195                 200                 205

Thr Lys Asn Gln Val Ser Leu Thr Cys Leu Val Lys Gly Phe Tyr Pro
        210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255
```

```
Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 3
<211> LENGTH: 65
<212> TYPE: PRT
<213> ORGANISM: Homo sapiens
<220> FEATURE:
<221> NAME/KEY: misc_feature
<222> LOCATION: (1)..(65)
<223> OTHER INFORMATION: Human IL-15R-alpha-Su (65aa  truncated
      extracellular domain)

<400> SEQUENCE: 3

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 4
<211> LENGTH: 135
<212> TYPE: PRT
<213> ORGANISM: Homo sapiens
<220> FEATURE:
<221> NAME/KEY: misc_feature
<222> LOCATION: (1)..(135)
<223> OTHER INFORMATION: Human IL-15 isoform 2

<400> SEQUENCE: 4

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 5
```

```
<211> LENGTH: 162
<212> TYPE: PRT
<213> ORGANISM: Homo sapiens
<220> FEATURE:
<221> NAME/KEY: misc_feature
<222> LOCATION: (1)..(162)
<223> OTHER INFORMATION: Human IL-15 isoform 1

<400> SEQUENCE: 5

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 6
<211> LENGTH: 114
<212> TYPE: PRT
<213> ORGANISM: Homo sapiens
<220> FEATURE:
<221> NAME/KEY: misc_feature
<222> LOCATION: (1)..(114)
<223> OTHER INFORMATION: Human IL-15 (without signal peptide)

<400> SEQUENCE: 6

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 7
```

```
<211> LENGTH: 85
<212> TYPE: PRT
<213> ORGANISM: Homo sapiens
<220> FEATURE:
<221> NAME/KEY: misc_feature
<222> LOCATION: (1)..(85)
<223> OTHER INFORMATION: Human IL-15R-alpha  (85aa  truncated
      extracellular domain)

<400> SEQUENCE: 7

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val
                85

<210> SEQ ID NO 8
<211> LENGTH: 182
<212> TYPE: PRT
<213> ORGANISM: Homo sapiens
<220> FEATURE:
<221> NAME/KEY: misc_feature
<222> LOCATION: (1)..(182)
<223> OTHER INFORMATION: Human IL-15R-alpha (182aa  truncated
      extracellular domain)

<400> SEQUENCE: 8

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr
            180
```

```
<210> SEQ ID NO 9
<211> LENGTH: 267
<212> TYPE: PRT
<213> ORGANISM: Homo sapiens
<220> FEATURE:
<221> NAME/KEY: misc_feature
<222> LOCATION: (1)..(267)
<223> OTHER INFORMATION: Human IL-15R-alpha  Full length

<400> SEQUENCE: 9

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

CELL SURFACE COUPLING OF NANOPARTICLES

CROSS-REFERENCE TO RELATED APPLICATIONS

This application is a division of U.S. patent application Ser. No. 15/236,186, filed on Aug. 12, 2016, pending, which claims priority to and the benefit of U.S. Provisional Patent Application No. 62/204,337, filed Aug. 12, 2015, the entire contents of which is herein incorporated by reference.

FEDERALLY SPONSORED RESEARCH

This invention was made with Government support under Grant No. R01 CA172164 awarded by the National Institutes of Health. The Government has certain rights in the invention.

SEQUENCE LISTING

The instant application contains a Sequence Listing which has been submitted electronically in ASCII format via EFS-Web and is hereby incorporated by reference in its entirety. Said ASCII copy, created May 12, 2021, is named "MITN1-004DV_Sequence-Listing.txt" and is 14005 bytes in size.

BACKGROUND OF THE INVENTION

Combining nanostructure (e.g.: nanoparticle- and liposome) based drug delivery strategies with cell-based therapies has created a lot of opportunities in developing novel therapeutic modalities with improved efficacy and reduced toxicity for the treatment of various diseases. For example, nanoparticles containing supporting drugs (e.g., cytokines) can be coupled with therapeutic cells (e.g., tumor reactive T cells) to boost the cell-based therapy (*Cancer Res.* 2007, 67, 300-308; *Nat. Med.* 2010, 16, 1035-1041). Alternatively, certain types of cells (e.g., antigen-specific T cells, mesenchymal stem cells) can be used as carriers to specifically target drug-contained nanoparticles to disease site to improve therapeutic efficacy (*Nat. Med.* 2005, 11, 1073-1081; *ACS Nano* 2011, 5, 7462-7470).

SUMMARY OF THE INVENTION

This present disclosure provides, in some aspects, a method for efficiently and stably coupling nanostructures to a carrier cell surface (e.g., T cell surface) with minimum cellular internalization, permitting extracellular drug (e.g., cytokine and small molecule) delivery in vivo for various biological applications, such as targeted immunotherapy. Typically, coupling of a particle (or nanostructure) to the surface of a T cells triggers internalization of the particle (or nanostructure) through, for example, T cell receptor-mediated endocytosis or membrane permeation. Such internalization mechanisms prevent T cells, which naturally home in vivo to particular tissues, from being utilized as carrier cells for the delivery of, for example, therapeutic or diagnostic agents. Surprisingly, experimental results provided herein show that nanostructures surface-modified with (e.g., conjugated to), for example, a ligand that binds to CD45 (e.g., an anti-CD45 antibody) are maintained at the surface of T cells expressing CD45. Thus, the present disclosure unexpectedly shows that not all T cell receptors promote receptor-mediated endocytosis. Some molecules, such as CD45, are capable of maintaining particles at the surface of the carrier cell. Also surprising are results showing that CD45, in particular, even when expressed in combination with internalizing T cell receptors, minimizes particles (e.g.: nanostructures) coupled to the cell surface from being internalized.

Further, experimental results show, unexpectedly, that a coupling efficiency of, for example, 89.6% can be achieved when adding a polycation (e.g., poly-L-lysine) to the surface of a nanostructure prior to performing a coupling reaction with a carrier cell (e.g., T cell). As an example, human IL-15Sa protein nanogels were coupled to activated T cells using a method of the present disclosure for adoptive cell therapy, and highly efficient expansion of the transferred T cells was achieved with substantially reduced toxicity in mice compared with soluble human IL-15Sa at an equivalent dose. Such results were unexpected given the cellular toxicity known to result from delivery of DNA coated and condensed using a polycationic coatings.

The compositions provided herein are useful to improve the efficiency and stability of coupling of nanostructures to a carrier cell surface (e.g., T cell surface) for a variety of biomedical and pharmaceutical applications such as, for example, therapeutic and prophylactic (e.g., drug delivery) as well as diagnostic (e.g., imaging and tracking) applications.

Thus, some aspects of the present disclosure provide compositions comprising a carrier cell having a cell surface coupling receptor, and a nanostructure surface-modified with a ligand that binds to the cell surface coupling receptor. In certain embodiments, the carrier cell is a nucleated carrier cell. In certain embodiments the nucleated carrier cell homes to a tumor. In certain embodiments, the composition comprises a nucleated carrier cell having a cell surface coupling receptor coupled to a nanostructure surface-modified with a ligand that binds to the cell surface coupling receptor. In some embodiments, the ligand is selected from the group consisting of antibodies, soluble protein receptors, cytokines, peptides, small molecules, co-factors, hormones and neurotransmitters.

In some embodiments, the cell surface coupling receptor is CD45.

In some embodiments, the ligand is an anti-CD45 antibody. In some embodiments, the anti-CD45 antibody is a human anti-CD45 antibody or a humanized anti-CD45 antibody. In some embodiments, the anti-CD45 antibody is an anti-CD45 monoclonal antibody. In some embodiments, the anti-CD45 monoclonal antibody is selected from the group consisting of BC8, 4B2, 9.4 and GAP8.3.

In some embodiments, the ligand is bound to the cell surface coupling receptor, thereby linking, or coupling, the nanostructure to the nucleated caner cell.

In some embodiments, the ligand binds to the cell surface coupling receptor.

In some embodiments, the ligand binds to the cell surface coupling receptor and at least 50% (e.g., at least 60%, at least 70%, at least 80%, at least 90%, or at least 95%) of the ligand (e.g., anti-CD45 antibody) remains on the surface of the cell for at least 24 hours (e.g., at least 36 hours, or at least 48 hours).

In some embodiments, the carrier cell is a T cell, a B cell, a Natural Killer (NK) cell or hematopoietic progenitor cell. In some embodiments, the carrier cell is a T cell. For example, the T cell may be a CD8$^+$ T cell or a CD4$^+$ T cell. In some embodiments, the T cell is an adoptively transferred T cell. In some embodiments, the T cell is a chimeric antigen receptor (CAR) T cell.

In some embodiments, the nanostructure is a nanoparticle or a liposome.

In some embodiments, the nanoparticle is selected from the group consisting of: protein nanogels, nucleic acid nanogels and solidified polymers.

In some embodiments, the nanostructure is a liposome. In some embodiments, the liposome is an interbilayer-crosslinked multilamellar vesicle (ICMV) or a unilamellar vesicle.

In some embodiments, the nanoparticle is a protein nanogel. In some embodiments, the protein nanogel is a carrier-free protein nanogel.

In some embodiments, the nanostructure has a diameter of 1 to 1000 nanometers (nm). For example, the nanostructure may have a diameter of 50 to 500 nm.

In some embodiments, the ligand is covalently conjugated to the nanostructure. In some embodiments, the ligand is covalently conjugated to the nanostructure via a maleimide-thiol reaction.

In some embodiments, the nanostructure comprises an agent. In some embodiments the nanostructure is a protein nanogel or a liposome comprising an agent. In some embodiments, the agent is selected from the group consisting of therapeutic agents, prophylactic agents, diagnostic agents and imaging agents. In some embodiments, the agent is selected from the group consisting of proteins, nucleic acids and small molecule drugs. In some embodiments, the agent is a biologically active protein. For example, the biologically active protein is a cytokine, such as IL-2, IL-15 or IL-15-superagonist (IL-15-superagonist is also referred to as IL-15Sa or IL-15SA).

In some embodiments, the nanostructure (e.g.: protein nanogel) comprises on its surface a polycation. In some embodiments, the polycation is polylysine. In some embodiments, the polycation is polyethylene glycol-b-polylysine or polyethylene glycol-g-polylysine.

In some embodiments, the compositions comprise a nucleated carrier cell covalently conjugated to a nanostructure comprising a surface polycation.

Some aspects of the present disclosure provide compositions comprising a T cell having a CD45 receptor, coupled to a protein nanogel that comprises a polycation and a ligand (e.g., anti-CD45 antibody) that binds the CD45 receptor.

Some aspects of the present disclosure provide compositions comprising a T cell having a CD45 receptor, coupled to a protein nanogel that comprises an agent, a polycation and a ligand (e.g., anti-CD45 antibody) that binds the CD45 receptor.

Some aspects of the present disclosure provide compositions comprising a T cell having a CD45 receptor, coupled to a liposome comprising a ligand (e.g., anti-CD45 antibody) that binds the CD45 receptor.

Some aspects of the present disclosure provide compositions comprising a T cell having a CD45 receptor, coupled to a liposome comprising an agent and a ligand (e.g., anti-CD45 antibody) that binds the CD45 receptor.

Some embodiments of the present disclosure provide compositions comprising a nucleated carrier cell that homes to a tumor and is coupled to a nanostructure comprising a biologically active protein, wherein the carrier cell comprises a CD45 receptor and is coupled to the nanostructure with a ligand that binds the CD45 receptor or the carrier cell comprises a negatively charged cell membrane and the nanostructure comprises a polycation surface which interacts electrostatically with the cell membrane, and wherein the nanostructure is a protein nanogel or a liposome.

In in certain aspects the carrier cell comprises a CD45 receptor and is coupled to the nanostructure with a ligand that binds the CD45 receptor.

In certain aspects the ligand is an anti-CD45 monoclonal antibody.

In certain aspects the carrier cell comprises a negatively charged cell membrane and the nanostructure comprises a polycation surface which interacts electrostatically with the cell membrane. In certain aspects, the polycation is polylysine. In certain aspects, the polycation is polyethylene glycol-b-polylysine (PEG-PLL).

In some embodiments, the composition comprises a nanostructure wherein the nanostructure is a protein nanogel and the protein nanogel comprises a plurality of biologically active proteins reversibly and covalently crosslinked to each other through a degradable linker. In some embodiments, the degradable linker is a redox responsive linker that comprises a disulfide bond.

In some embodiments, the composition comprises a nanostructure wherein the nanostructure is a liposome and the liposome comprises a plurality of biologically active proteins. In certain aspects the liposome is unilamellar or an interbilayer-crosslinked multilamellar vesicle.

In some embodiments, the composition comprises a carrier cell wherein the carrier cell is a T cell, a B cell a Natural Killer (NK) cell or a hematopoietic progenitor cells. In some aspects, the carrier cell is a T cell. In some aspects, the T cell is a $CD8^+$ T cell or a $CD4^+$ T cell. In some aspects, the T cell is an adoptively transferred T cell. In some aspects, the T cell is a chimeric antigen receptor (CAR) T cell.

In some embodiments, the composition comprises a nanostructure comprising biologically active protein wherein the biologically active protein is selected from the group consisting of antibodies, antibody fragments, soluble protein receptors and cytokines. In some aspects, the cytokine is IL-2, IL-7, IL-15 (or superagonist/mutant forms of these cytokines e.g.: IL-15Sa), IL-12, IFN-gamma, IFN-alpha, GM-CSF, FLT3-ligand. In some aspects, the cytokine is IL-15-Sa. In some aspects, the IL-15Sa comprises a complex comprising a dimeric IL-15RαSu/Fc and two IL-15N72D molecules. In some aspects, the dimeric IL-15RαSu/Fc comprises an amino acid sequence set forth in SEQ ID NO: 2 and the IL-15N72D molecule comprises an amino acid sequence set forth in SEQ ID NO: 1.

In some embodiments the composition comprises a pharmaceutically acceptable carrier. In some aspects the composition is useful as a medicament for delivering a biologically active protein to a subject having a tumor.

Certain aspects of the disclosure provide methods of treating cancer in a subject comprising administering to a subject in need thereof a composition as described herein.

Certain aspects of the disclosure provide a composition comprising a nucleated carrier cell (e.g.: a T cell) that homes to a tumor coupled to a nanostructure comprising a biologically active protein, wherein (a) the carrier cell comprises a CD45 receptor and is coupled to the nanostructure with a ligand that binds the CD45 receptor; or (b) the carrier cell comprises a negatively charged cell membrane and the nanostructure comprises a polycation surface which interacts electrostatically with the cell membrane; or (c) the carrier cell comprises a CD45 receptor and is coupled to the nanostructure with a ligand that binds the CD45 receptor, and the carrier cell comprises a negatively charged cell membrane and the nanostructure comprises a polycation surface which interacts electrostatically with the cell membrane.

Certain aspects of the disclosure provide a composition comprising a nucleated carrier cell (e.g.: T cell) comprising a CD45 receptor and a nanostructure comprising a biologically active protein, wherein the carrier cell is coupled to the nanostructure with a ligand that binds the CD45 receptor.

Certain aspects of the disclosure provide a composition comprising a nucleated carrier cell (T cell) that homes to a tumor coupled to a nanostructure comprising a biologically active protein, wherein the carrier cell comprises a negatively charged cell membrane and the nanostructure comprises a polycation surface which interacts electrostatically with the cell membrane.

Certain aspects of the disclosure provide a composition comprising a nucleated carrier cell comprising a CD45 receptor and a protein nanogel, wherein the carrier cell is coupled to the protein nanogel with a ligand that binds the CD45 receptor, and wherein the protein nanogel comprises a plurality of biologically active proteins reversibly and covalently crosslinked to each other through a degradable linker.

Certain aspects of the disclosure provide a composition comprising a nucleated carrier cell (e.g.: a T cell) that homes to a tumor coupled to a protein nanogel, wherein the carrier cell comprises a negatively charged cell membrane and the protein nanogel comprises a polycation surface which interacts electrostatically with the cell membrane, and wherein the protein nanogel comprises a plurality of biologically active proteins reversibly and covalently crosslinked to each other through a degradable linker.

Certain aspects of the disclosure provide a composition comprising a nucleated carrier cell (e.g.: a T cell) comprising a CD45 receptor and a liposome comprising a plurality of biologically active proteins, wherein the carrier cell is coupled to the liposome with a ligand that binds the CD45 receptor.

Also provided herein are methods of producing a composition comprising a carrier cell coupled to a nanostructure, the method comprising modifying the surface of a nanostructure to contain a ligand (e.g., anti-CD45 antibody) that binds to a cell surface coupling receptor (e.g., CD45) located on the surface of a carrier cell; and combining the nanostructure and the carrier cell comprising the cell surface coupling receptor under conditions that result in binding of the ligand to the cell surface coupling receptor on the surface of the carrier cell, thereby producing a cell coupled to a nanostructure.

Further provided herein are methods of producing a composition comprising a carrier cell coupled to a nanostructure, the method comprising combining (a) a nanostructure surface modified to contain a ligand (e.g., anti-CD45 antibody) that binds to a cell surface coupling receptor (e.g., CD45) located on the surface of a carrier cell and (b) the carrier cell comprising the cell surface coupling receptor, wherein the nanostructure and carrier cell are combined under conditions that result in binding of the ligand to the cell surface coupling receptor on the surface of the carrier cell, thereby producing a carrier cell coupled to a nanostructure.

Some aspects of the present disclosure provide methods of producing a composition comprising a carrier cell coupled to a nanostructure, the method comprising combining (a) a nanostructure surface modified to contain a chemical linker with (b) a polycation under conditions that result in a nanostructure with positive charges on its surface which interacts electrostatically with the cell membrane; and covalently conjugating the nanostructure to a cell, thereby producing a carrier cell coupled to a nanostructure.

Also provided herein are methods of producing a composition comprising a carrier cell coupled to a nanostructure, the method comprising combining (a) a nanostructure surface modified to contain a chemical linker and ligand that binds to a cell surface coupling receptor located on the surface of a carrier cell with (b) a polycation under conditions that result in a nanostructure with positive charges on its surface which interacts electrostatically with the cell membrane; combining the nanoparticle with the carrier cell comprising the cell surface coupling receptor under conditions that result in binding of the ligand to the cell surface coupling receptor; and covalently conjugating the nanostructure with positive charges on its surface which interacts electrostatically with the cell membrane to the carrier cell comprising the cell surface coupling receptor, thereby producing a carrier cell coupled to a nanostructure.

One aspect of the disclosure provides a method for delivering an agent (e.g., a biologically active protein) by administering to a subject a composition comprising a nucleated carrier cell that homes to a tumor coupled to a nanostructure (e.g., nanoparticle or liposome) comprising an agent, wherein the carrier cell comprises a cell surface coupling receptor, and wherein the nanostructure is coupled to the carrier cell with a ligand that binds to the cell surface coupling receptor, such that the agent is released from the nanostructure in vivo.

Other aspects of the disclosure relate to methods for delivering an agent (e.g., a biologically active protein) by administering to a subject a composition comprising a nucleated carrier cell that homes to a tumor coupled to a nanostructure (e.g., nanoparticle or liposome) comprising an agent, wherein the nanostructure comprises a surface associated with a polycation (e.g., polylysine), such that the agent is released from the nanostructure in vivo.

Yet other aspects of the disclosure relate to methods for delivering a biologically active protein (e.g., a cytokine) by administering to a subject a composition comprising a nucleated carrier cell that homes to a tumor coupled to a nanostructure (e.g., nanoparticle or liposome) comprising a biologically active protein, wherein the carrier cell comprises a CD45 receptor coupled to the nanostructure with a ligand that binds the CD45 receptor or the carrier cell comprises a negatively charged cell membrane and the nanostructure comprises a polycation surface which interacts electrostatically with the cell membrane, and wherein the nanostructure is a protein nanogel or a liposome, such that the biologically active protein is released from the nanostructure in vivo.

In other aspects, the disclosure provides methods for delivering an immunostimulatory cytokine by administering to a subject a composition comprising a T cell that homes to a tumor coupled to a nanostructure comprising an immunostimulatory cytokine, wherein the T cell comprises a CD45 receptor coupled to the nanostructure with a ligand that binds the CD45 receptor or the T cell comprises a negatively charged cell membrane and the nanostructure comprises a polycation surface which interacts electrostatically with the cell membrane, or both, and wherein the nanostructure is a protein nanogel or a liposome, such that the immunostimulatory cytokine is released from the nanostructure in vivo.

In another aspect, the disclosure provides a method for delivering an immunostimulatory cytokine to a tumor comprising administering to a subject having a tumor a tumor-reactive T cell coupled to a nanogel comprising an immunostimulatory cytokine, wherein the T cell comprises a CD45 receptor coupled to the nanogel with a ligand that binds the CD45 receptor and wherein the T cell comprises a negatively charged cell membrane and the nanogel comprises a polycation surface which interacts electrostatically with the cell membrane, such that the immunostimulatory cytokine is released from the nanostructure in vivo.

In another aspect, the disclosure provides a method for delivering an immunostimulatory cytokine to a tumor comprising administering to a subject having a tumor a chimeric antigen receptor (CAR) T cell coupled to a nanostructure (e.g., nanogel or liposome) comprising an immunostimulatory cytokine, wherein the CAR T cell comprises a CD45 receptor coupled to the nanostructure with a ligand that binds the CD45 receptor or wherein the CAR T cell comprises a negatively charged cell membrane and the nanostructure comprises a polycation surface which interacts electrostatically with the cell membrane, or both, such that the immunostimulatory cytokine is released from the nanostructure in vivo.

Other aspects of the disclosure provide methods for maintaining, stimulating or enhancing activity of a T cell in a subject comprising administering to a subject a composition comprising a T cell coupled to a nanostructure (e.g., nanogel or liposome) comprising an immunostimulatory cytokine, wherein the T cell comprises a CD45 receptor coupled to the nanostructure with a ligand that binds the CD45 receptor or wherein the T cell comprises a negatively charged cell membrane and the nanostructure comprises a polycation surface which interacts electrostatically with the cell membrane, or both, such that the immunostimulatory cytokine is released from the nanostructure in vivo and activity of the T cell is maintained, stimulated or enhanced.

Yet other aspects of the disclosure relate to methods for maintaining, stimulating or enhancing activity of a T cell located in the environment of a tumor, comprising administering to a subject having a tumor a carrier T cell that homes to the tumor coupled to a nanostructure (e.g., nanogel or liposome) comprising an immunostimulatory cytokine, wherein the carrier T cell comprises a CD45 receptor coupled to the nanostructure with a ligand that binds the CD45 receptor or wherein the carrier T cell comprises a negatively charged cell membrane and the nanostructure comprises a polycation surface which interacts electrostatically with the cell membrane, or both, and wherein release of the immunostimulatory cytokine from the nanogel or liposome maintains, stimulates or enhances activity of a T cell located in the environment of the tumor.

In some embodiments, the subject has a tumor. In related embodiments, the cell is a tumor-reactive T cell. In other related embodiments, the carrier cell homes to the tumor or to the tissue in which the tumor exists (e.g., lymphoid tissue). In some embodiments, the tumor is a lymphoma and the agent is an antibody, such as an anti-CD20 antibody, or a chemotherapy, such as fludaribine. Other agents having therapeutic effect on lymphoma may be used in place of or in addition to anti-CD20 antibody or fludaribine.

In some embodiments, the subject has an autoimmune disease. In some embodiments, the subject has an infection. In some embodiments, the subject is in need of hematopoietic reconstitution as a result of, for example, myeloablative chemotherapy and/or radiation.

In some embodiments, the cell is a gut-specific T cell. In some embodiments, the cell is a skin-specific T cell.

In some embodiments, the cell is autologous to the subject. In some embodiments, the cell is activated prior to administration to the subject. In some embodiments, the cell is genetically engineered, such as, for example a chimeric antigen receptor (CAR) T cell.

In some embodiments, the agent is an imaging agent. In some embodiments, the agent is an immunostimulatory protein, such as a cytokine. In some embodiments, the cytokine is IL15SA. In some embodiments, the agent is an antigen. In some embodiments, the agent is an adjuvant. In some embodiments, the adjuvant is a TLR ligand. The TLR ligand may function to stimulate antigen-specific immune responses (typically in the presence of exogenous or endogenous antigens) and/or antigen-non-specific immune responses. Thus, the TLR ligand may be used in the presence or absence of an antigen. In some embodiments, the agent is an antibody or an antibody fragment. In some embodiments, the agent is a drug. In some embodiments, the agent is a chemical compound. In some embodiments, the agent is a nucleic acid. In some embodiments, the nucleic acid is an siRNA.

In some embodiments, the agents are anti-cancer agents including anti-cancer antibodies, cancer antigens, anti-cancer chemotherapeutic agents, and the like. In various embodiments, the agents may be used at doses that are below doses required to achieve the same effects in vivo following systemic administration. In some instances, the doses are at least 2 times less, at least 5 times less, at least 10 times less, at least 20 times less, at least 50 times less, or at least 100 times less than the required systemic dose.

In some embodiments, the cell is covalently bound to a plurality of nanostructures. In some embodiments, the plurality of nanostructures comprises the same or different agents.

In some embodiments, the agent acts in an autocrine manner (i.e., it acts upon the carrier cell itself). In some embodiments, the agent acts in a paracrine manner (i.e., it acts upon cells other than the cell carrier, such as cells at the site of a tumor in vivo). In still other embodiments, the agent acts in both an autocrine and a paracrine manner.

These and other aspects and embodiments will be described in greater detail herein. This disclosure is not limited in its application to the details of construction and/or the arrangement of components set forth in the following description or illustrated in the drawings.

BRIEF DESCRIPTION OF THE DRAWINGS

The accompanying drawings are not intended to be drawn to scale. For purposes of clarity, not every component may be labeled in every drawing.

FIGS. 5C-5E show ratios of counts of ACT CD8$^+$ T-cells in the group of T+aCD45/IL-15Sa-NG to that of T+free IL-15Sa in different tissues (FIG. 5C), counts of Ki67+ ACT CD8+ T-cells in tumours analysed by intracellular staining and flow cytometry (FIG. 5D), and counts of polyfunctional ACT CD8+ T-cells in tumours by intracellular cytokine staining (FIG. 5E).

DETAILED DESCRIPTION OF THE INVENTION

Figure 1A:
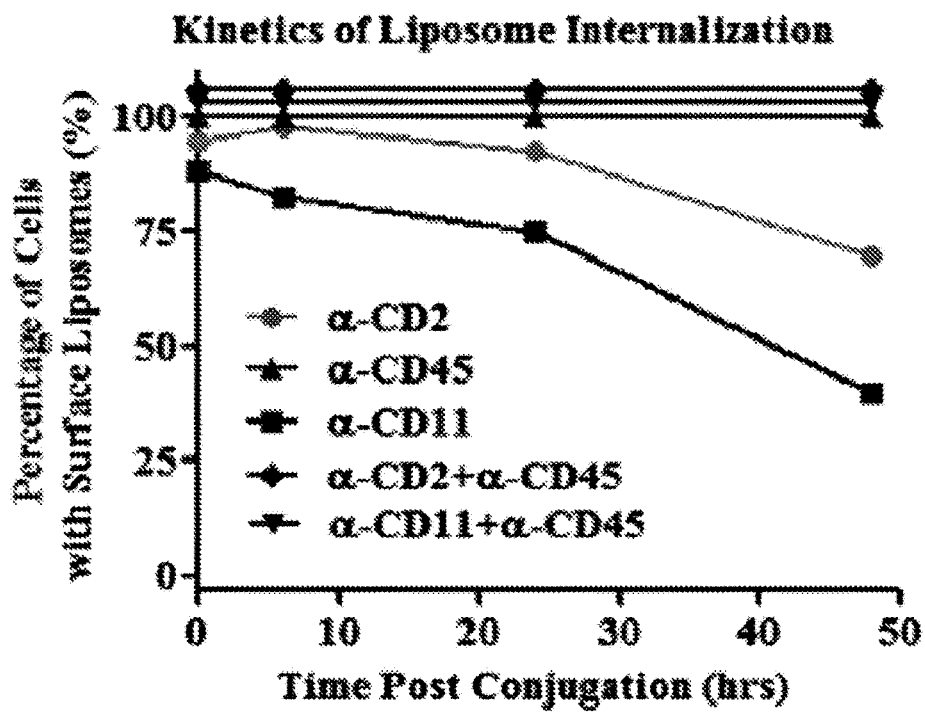
FIGS. 1A-1C show internalization kinetics of liposomes with surface antibodies, α-CD2, α-CD8, α-CD11, α-CD45, and/or α-Thy1.1.

Provided herein, in some aspects, are methods and compositions for efficiently and stably coupling a nanostructure to a carrier cell surface with minimum cellular internalization, permitting, for example, carrier cell drug delivery in vivo for targeted immunotherapy. Typically, linking or coupling a nanostructure (e.g., a synthetic nanoparticle or liposome) to the surface of a T cell, for example, triggers receptor-mediated endocytosis. To minimize or prevent nanostructures from being endocytosed by carrier cells, the nanostructures can be coupled to the surface of the carrier cell though covalent modifications (see, e.g., US20150110740 A1, incorporated herein by reference). The present disclosure is based, at least in part, on surprising results showing that the coupling of a nanostructure to a surface of a cell is facilitated by expressing a receptor with prolonged residence time at the surface of the cell and attaching a cognate ligand to the nanostructure. Surprisingly, certain cell surface receptors (e.g., CD45) are capable of maintaining nanostructures at the surface of a cell, rather than triggering the classical endocytotic internalization pathway. These cell surface coupling receptors increase loading and/or coupling efficiency of the nanostructure to the cell surface. Such cell surface receptors are referred to herein as "cell surface coupling receptors". These cell surface coupling receptors have a prolonged cell surface residence time and/or are maintained on the cell surface with minimal internalization.

Accordingly, in some aspects, the present disclosure provides compositions comprising nucleated carrier cells that express at least one cell surface coupling receptor coupled to one or more nanostructures modified to provide a ligand that binds to the cell surface coupling receptor. One such example is a T cell that expresses CD45 coupled to a nanostructure via an anti-CD45 antibody provided by the nanostructure.

Also provided herein are compositions for improving the coupling efficiency and increase loading of nanostructures (e.g.: protein nanogels) to carrier cells through the use of a polycation, which, when added to the surface of a nanostructure prior to performing a coupling reaction, functions to neutralize negatively-charged T cells. In effect, the polycation acts as a "magnet" to bring the nanostructure (e.g.: nanogel) in close proximity to the cell during a coupling reaction, thereby increasing the efficiency of the coupling reaction.

Nanostructures for Coupling to Carrier Cells

Nanostructures of the present disclosure generally are microscopic particles having at least one dimension less than 1000 nm (e.g., less than 500, less than 250, less than 100 nm). The term "nanostructure" encompasses liposomes and nanoparticles as described herein. In some embodiments, nanostructures are synthetic. That is, the nanostructures do not occur naturally.

In some embodiments, nanostructures are synthesized to comprise one or more reactive groups on their exterior surface for reaction with reactive groups on cell carriers. These nanostructure reactive groups include, without limitation, thiol-reactive maleimide head groups, haloacetyl (e.g., iodoacetyl) groups, imidoester groups, N-hydroxysuccinimide esters, and pyridyl disulfide groups. These reactive groups react with groups on the carrier cell surface and, thus, provide coupling of the nanostructures to the cell surface. It should be understood that when surface modified in this manner, the nanostructures are intended for use with specific carrier cells having "complementary" reactive groups (i.e., reactive groups that react with those of the nanostructures). In some embodiments, the nanostructures do not integrate into the lipid bilayer that comprises the cell surface.

Nanostructures may be covalently conjugated or non-covalently conjugated to the carrier cells. The process of conjugating a nanostructure to a cell is referred to herein as a "coupling reaction." Covalent conjugation typically provides a more stable (and thus longer) association between the nanostructures and the carrier cells. Covalent conjugation in some embodiments also can provide stability and, thus, more sustained localized delivery of agents in vivo. Non-covalent conjugation includes without limitation absorption onto the cell surface and/or lipid bilayer of the cell membrane.

In some embodiments, covalent attachment is achieved through a maleimide-thiol reaction, wherein there is a two-step process in which carrier cells are first incubated with maleimide-bearing nanostructures to allow conjugation to the cell surface, followed by in situ PEGylation with thiol-terminated polyethylene glycol (PEG) to cap remaining maleimide groups of the particles and avoid particle-mediated crosslinking of cells. With this approach, substantial numbers of nanostructures with diameters in the 100-300 nm range have been conjugated to cell types used commonly in cell therapy. This strategy allows particles ranging from simple liposomes (e.g., with an aqueous drug-loaded core) to more complex lipid-coated polymer or DNA-based nanostructures to be stably attached to carrier cells. Importantly, the linkage chemistry is benign and non-toxic as evidenced in part by the conjugation of up to 139 (±29) ~200 nm-diameter lipid-coated nanoparticles to the surface of cells without any deleterious effect (see U.S. Patent Application Publication No. 2011/0293705).

In some embodiments, a nanostructure is a polymersome. Polymersomes are a class of artificial vesicles that may be used for drug delivery or as artificial organelles. The vesicle membranes are made of block copolymers. Polymersomes have an ability to encapsulate and transport molecules in the central water pool or sequestered in their hydrophobic bilayer membrane. Polymersomes differ from liposomes in that they are generally more highly stable and the bilayer membranes of polymersomes are often relatively impermeable, thereby hindering the release of encapsulated molecules. Polymersomes are useful for encapsulating and protecting sensitive molecules, such as drugs, enzymes, other proteins and peptides, and DNA and RNA fragments. Polymersomes have the ability to load both hydrophilic and hydrophobic molecules, making them excellent candidates to use as drug delivery systems.

In some embodiments, nanostructures comprise a lipid bilayer on the outermost surface of the nanostructure. This bilayer may be comprised of one or more lipids of the same or different type. Examples include, without limitation, phospholipids such as phosphocholines and phosphoinositols. Specific examples include, without limitation, DMPC, DOPC, DSPC, and various other lipids such as those recited below. The size of a protein nanostructure may be determined at least two ways: based on its "dry size" and based on its "hydrodynamic size." In certain embodiments, the "dry size" of a nanostructure (e.g.: nanogel) refers to the diameter of the nanostructure (e.g.: nanogel) as a dry solid. The dry size of a nanostructure (e.g.: nanogel) may be determined, for example, by transmission electron microscopy.

In other embodiments, the "hydrodynamic size" of a nanostructure (e.g: liposome) refers to the diameter of the nanostructure (e.g.: liposome) as a hydrated gel (e.g., a liposome in an aqueous buffer). The hydrodynamic size of the nanostructure (e.g.: liposomes) may be determined, for example, by dynamic light scattering. Methods for measuring nanostructure (e.g.: liposomes) diameter by dynamic light scattering are known in the art (see, for example, Malvern Instruments, Ltd. on the world wide web at: malvern.co.uk)

In some embodiments, the dry size of a nanostructure is less than 100 nm. In some embodiments, the dry size of a nanostructure is less than 95 nm, less than 90 nm, less than 85 nm, less than 80 nm, less than 75 nm, less than 70 nm, less than 65 nm, or less than 60 nm. In some embodiments, the dry size of a nanostructure is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanostructure is 40 nm, 45 nm, 50 nm, 55 nm, 60 nm, 65 nm, 70 nm, 75 nm, 80 nm, 85 nm, 90 nm or 95 nm.

In some embodiments, the average dry size of a nanostructure within a plurality of nanostructures is less than 100 nm. In some embodiments, the average dry size of a nanostructure within such a plurality varies by no more than 5% or 10%. In some embodiments, the average dry size of a nanostructure (e.g., nanogel) within a plurality of nanostructures is less than 95 nm, less than 90 nm, less than 85 nm, less than 80 nm, less than 75 nm, less than 70 nm, less than 65 nm, or less than 60 nm. In some embodiments, the average dry size of a nanostructure (e.g., nanogel) within a plurality of nanostructures is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanostructure is 40 nm, 45 nm, 50 nm, 55 nm, 60 nm, 65 nm, 70 nm, 75 nm, 80 nm, 85 nm, 90 nm or 95 nm.

In some embodiments, the hydrodynamic size of a nanostructure is less than 100 nm. In some embodiments, the dry size of a nanostructure is less than 95 nm, less than 90 nm, less than 80 nm, less than 85 nm, or less than 75 nm. In some embodiments, the hydrodynamic size of a nanostructure is 70 to 90 nm, 70 to 85 nm, 70 to 80 nm, 75 to 90 nm, 75 to 85 nm, 75 to 80 nm, 80 to 90 nm, 80 to 85 nm or 85 to 90 nm. In some embodiments, the hydrodynamic size of a nanostructure is 70 nm, 75 nm, 80 nm, 85 nm, 90 nm, or 95 nm. In some embodiments, the hydrodynamic size of a nanostructure is 80 nm, 81 nm, 82 nm, 83 nm, 84 nm, 85 nm, 86 nm, 87 nm, 88 nm, 89 nm or 90 nm.

In some embodiments, the average hydrodynamic size of a nanostructure within a plurality of nanostructures is less than 100 nm. In some embodiments, the average hydrodynamic size of a nanostructure within such a plurality varies by no more than 5% or 10%. In some embodiments, the average hydrodynamic size of a nanostructure within a plurality of nanostructures is less than 95 nm, less than 90 nm, less than 80 nm, less than 85 nm, or less than 75 nm. In some embodiments, the average hydrodynamic size of a within a plurality of nanostructures is 70 to 90 nm, 70 to 85 nm, 70 to 80 nm, 75 to 90 nm, 75 to 85 nm, 75 to 80 nm, 80 to 90 nm, 80 to 85 nm or 85 to 90 nm. In some embodiments, the average hydrodynamic size of a nanostructure within a plurality of nanostructures is 70 nm, 75 nm, 80 nm, 85 nm, 90 nm, or 95 nm. In some embodiments, the average hydrodynamic size of a nanostructure within a plurality of nanostructures is 80 nm, 81 nm, 82 nm, 83 nm, 84 nm, 85 nm, 86 nm, 87 nm, 88 nm, 89 nm or 90 nm.

In some embodiments, nanostructures (e.g.: protein nanogels)) are provided in a dry, solid form, such as a lyophilized form. In other embodiments, nanostructures (e.g.: liposomes) are provided in a hydrated form, such as in aqueous or otherwise liquid solution.

Nanoparticles

The term "nanoparticle" includes nanogels (e.g: protein nanogels and nucleic acid nanogels), solid colloidal nanoparticles, magnetic nanoparticles, nobel metal nanoparticles, semiconductor nanoparticles, multimodal nanoparticles, composite nanoparticles, and other nanoparticles typically used for biomedical applications (see, e.g., Blanco-Andujar et al. *Annu. Rep. Prog. Chem., Sect.* A, 2010, 106, 553-568, incorporated by reference herein). It should be understood, however, that the term "nanoparticles" does not encompass viruses or viral particles or liposomes, although, in some embodiments, non-infectious virus-like particles (VLPs), which do not contain viral genetic material, are contemplated herein. Thus, in some embodiments, a composition comprises a VLP coupled to the surface of a cell. Nanoparticles are distinguished from films or other structurally layered polymers matrices.

In some embodiments, nanoparticles are synthetic. That is, the nanoparticles no not occur naturally. In some embodiments, nanoparticles are biodegradable and, thus, are not magnetic. Biodegradable nanoparticles may be synthesized using methods known in the art, including, without limitation, solvent evaporation, hot melt microencapsulation, solvent removal and spray drying. Exemplary methods for synthesizing nanoparticles are described by Bershteyn et al., *Soft Matter* 4:1787-1787, 2008 and in U.S. Patent Application Publication No. 2008/0014144 A1, the specific teachings of which relating to nanoparticle synthesis are incorporated herein by reference.

In some embodiments, nanoparticles release their agent "payload" over a number of days as a function of their degradation profile in vivo. Nanoparticles which are biodegradable in nature gradually degrade in an aqueous environment such as occurs in vivo. If the agents are dispersed throughout the nanoparticles, then their release occurs as the outermost layers of the nanoparticle degrade or as the pores within the nanoparticle enlarge. Release kinetic studies show that, in some embodiments, protein and small-molecule drugs can be released from biodegradable nanoparticles over time-courses ranging from 1 day to 2 weeks. Thus, in some embodiments biodegradable nanoparticles function to gradually release their payload into the environment of the target site(s).

In some embodiments, the diameter of a nanoparticle is, for example, 1-1000 nanometers (nm). In some embodiments, the diameter is 20-750 nm, 20-500 nm, or 20-250 nm. In some embodiments, the diameter is 50-750 nm, 50-500 nm, 50-250 nm, or 100-300 nm. In some embodiments, the diameter is 100 nm, 150 nm, 200 nm, 250 nm or 300 nm.

In some embodiments, a nanoparticle is comprised of one or more solidified polymers, arranged in a random manner. Exemplary synthetic polymers which can be used to form biodegradable nanoparticles include, without limitation, aliphatic polyesters, poly (lactic acid) (PLA), poly (glycolic acid) (PGA), co-polymers of lactic acid and glycolic acid (PLGA), polycarprolactone (PCL), polyanhydrides, poly (ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to an aqueous environment in vivo, by surface or bulk erosion.

A polymer is a natural or synthetic large molecule, or macromolecule, composed of many repeated, polymerized monomer subunits. Polymers can be formed from up to thousands of only one monomer or of a combination of monomers (copolymers). Synthetic polymers include, without limitation, plastics such as polystyrene and polyethylene. Natural polymers include, without limitation, biopolymers such as DNA and proteins. The large molecular mass of polymers relative to small molecule compounds produces unique physical properties, including toughness, viscoelasticity, and a tendency to form glasses and semicrystalline structures rather than crystals.

In some embodiments, protein nanoparticles (e.g., protein nanogels, including protein-polymer nanogels) of the present disclosure do not contain carrier proteins or other carrier molecules. For example, in some embodiments, protein nanoparticles do not contain albumin (e.g., bovine serum albumin (BSA)). Carrier proteins typically facilitate the diffusion and/or transport of different molecules. It should be understood that the term "carrier protein," as used herein, refers to a protein that does not adversely affect a biologically-active protein of a protein nanoparticle. In some embodiments, a carrier protein is an inert protein. Thus, in some embodiments, carrier proteins are not biologically active. Nanoparticles of the present disclosure, in some embodiments, do not require carrier proteins or other carrier molecules to facilitate their transport to and into cells and tissue in vivo.

Nanogels

In some embodiments, a nanoparticle is a nanogel, such as a protein nanogel or a nucleic acid nanogel. Nanogels may be composed of, for example, a hydrogel comprising particles formed by chemically or physically cross-linked polymer networks of nanoscale size. In some embodiments, nanogels may be composed of swollen nanosized networks composed of polymer chains that are hydrophilic or amphiphilic. In some embodiments, nanogels may be composed of swollen chemically cross-linked networks of cationic and neutral polymers, e.g., branched polyethylenimine (PEI) and polyethylene glycol (PEG) (PEG-cl-PEI). In some embodiments, nanogels may be composed of physically cross-linked cholesterol-modified polysaccharides (e.g., pullulan, mannan, amilopectin and dextran). Nanogels may be utilized as carriers for the transport of drugs, and can be designed to incorporate biologically active molecules through the formation of salt bonds, hydrogen bonds, or hydrophobic interactions.

In some embodiments, a nanoparticle is nucleic acid nanogel, wherein the nanoparticles are comprised of a nucleic acid internal core. Such "DNA nanoparticles" (or DNA-gel nanoparticles) are described in greater detail in published U.S. Patent Application Publication No. 20070148246. It is to be understood that the nucleic acid core of such nanoparticles may act as a scaffold for the agents being delivered in vivo and/or it may act as the agent itself. An exemplary protocol for synthesizing DNA nanoparticles is provided in U.S. Patent Application Publication No. 2011/0293705, incorporated herein by reference.

In some embodiments, the nanostructure (or nanoaparticle) is a protein nanogel. A protein nanogel refers to a plurality of proteins crosslinked (e.g., reversibly and covalently crosslinked) to each other through a degradable linker (see, e.g., US20150110740 A1, incorporated herein by reference). The proteins of a nanogel are reversibly crosslinked via the degradable linker (e.g., a disulfide linker), such that under physiological conditions, the linker degrades and releases the intact, biologically-active protein. In other embodiments, proteins of nanogels are reversibly linked to functional groups through a degradable linker such that under physiological conditions, the linker degrades and releases the intact, biologically-active protein. In each instance, the proteins are considered to be reversibly modified, as described below.

A protein that is "reversibly linked to another protein" herein refers to a protein that is attached (e.g., covalently attached) to another protein through a degradable linker. Such proteins are considered to be linked (e.g., crosslinked) to each other through the degradable linker. In some embodiments, nanogels contain a single (e.g., single type of) biologically-active protein (e.g., IL-2, IL-15, IL-15Sa, IL-2-Fc, IL-15-Fc, or IL-15Sa-Fc), while in other embodiments, nanostructures contain more than one (e.g., 2, 3, 4, 5 or more) of biologically-active protein (e.g., a combination of different proteins such as IL-2 and IL-15 (or IL-15SA)). For example, a protein nanogel may contain a combination of Protein A and Protein B, wherein Protein A is linked to Protein A, Protein A is linked to Protein B and/or Protein B is linked to Protein B.

A protein that is "reversibly linked to a functional group," or a protein that is "reversibly modified," herein refers to a protein that is attached (e.g., covalently attached) to a functional group through a degradable linker. Such a protein may be referred to herein as a "protein conjugate" or a "reversibly modified protein conjugate"—the terms may be used interchangeably herein. It should be understood that proteins and polymers each contain functional groups to which a protein can be linked via a reversible linker (e.g., degradable linker such as a disulfide linker). Examples of protein conjugates and reversibly modified proteins, as provided herein, include without limitation, a protein reversibly linked (e.g., via a degradable linker) to another protein, a protein reversibly linked to a polymer, and a protein reversibly linked to another functional group. It should be understood that the term "protein" also includes fusion proteins.

The degradable linkers provided herein, in some embodiments, comprise an N-hydroxysuccinimide ester, which is capable of reacting with proteins at neutral pH (e.g., about 6 to about 8, or about 7) without denaturing the protein. In some embodiments, the degradable linkers are "redox responsive" linkers, meaning that they degrade in the presence of a reducing agent (e.g., glutathione, GSH) under physiological conditions (e.g., 20-40° C. and/or pH 6-8), thereby releasing intact protein from the compound to which it is reversibly linked. An example of a degradable linker for use in accordance with the present disclosure is the following:

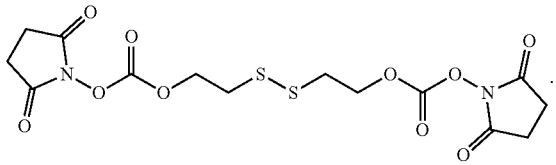

Formula I

The linker of Formula I contains a disulfide, which is cleaved in the presence of a reducing agent. For example, under physiological conditions, the disulfide bond of the linker of Formula I is cleaved by glutathione.

Proteins may be linked (e.g., covalently linked) to a degradable linker through any terminal or internal —NH$_2$ functional group (e.g., side chain of a lysine). Thus, an intermediate species formed during the reversible modification of a protein with a degradable linker of Formula I is the following:

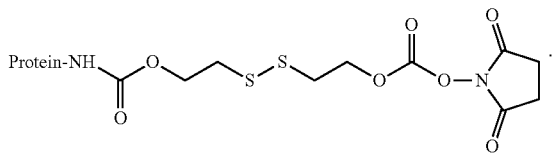

Formula II

Reversibly modified proteins provided herein can, in some embodiments, be formed or self-assemble into various nanogels including, without limitation, protein-hydrophilic polymer conjugates (e.g., reversibly modified with polyethylene glycol (PEG)), protein-hydrophobic polymer conjugates (e.g., reversibly modified PLA or PLGA), bulk crosslinked protein hydrogels, crosslinked protein nanogel particles, protein nanocapsules with different shell materials (e.g., silica), protein-conjugated nanostructures (e.g., liposome, micelle, polymeric nanoparticles, inorganic nanoparticles). Likewise, proteins crosslinked to each other, as provided herein, in some embodiments, can be formed or can self-assemble into protein nanostructures.

It is contemplated, in some embodiments that the proteins of a nanogel are irreversibly and covalently crosslinked via the non-degradable linker N-hyroxysulfosuccunimide linker.

The polymer, in some embodiments, may be crosslinked to the surface of the nanogel (e.g., to proteins exposed at the surface of the nanogel). In some embodiments, a protein nanogel is wrapped in a polymer-based, or silica, nanoshell. A nanoshell may be formed, in some embodiments, by polymerizing functional groups (e.g., silanes) of a protein conjugate with a crosslinker (e.g., silane-PEG-silane) in the presence of a catalyst (e.g., NaF).

It is contemplated that in some embodiments the proteins of the nanogel may comprise protein agents as described supra. In some embodiments, the protein nanogel may comprise, without limitation, protein(s) selected from the group consisting of therapeutic proteins, prophylactic proteins, diagnostic proteins, and imaging proteins. Examples of proteins for use in accordance with the present disclosure include, without limitation, antibodies, single chain antibodies, antibody fragments, enzymes, fusion proteins, co-factors, receptors, ligands, transcription factors and other regulatory factors, some antigens (as discussed below), cytokines, chemokines, and the like. The proteins may or may not be naturally occurring. Other proteins are contemplated and may be used in accordance with the disclosure. Such nanogels typically do not contain inert carrier proteins, such as albumin.

In some embodiments, proteins of the nanogel are biologically active proteins, such as protein agents described supra. In certain embodiments the protein agents are immunomodulatory proteins (e.g., immunostimulatory or immunoinhibitory proteins) as described herein. In certain aspects it is contemplated that the immunomodulatory protein is programmed death-ligand 1 (PD-L1), cytotoxic T-lymphocyte-associated protein 4 (CTLA-4), interleukin 10 (IL-10) or transforming growth factor beta (TGF-beta).

In some embodiments, the proteins of the nanogel are fusion proteins of a biologically active protein fused to an immunogloulin Fc domain, referred to as an Fc fusion protein (e.g., human IgG1 Fc fusion protein). In some embodiments, the biologically active protein of the nanogel is a cytokine, including, without limitation, IL-12, IL-15, IL-15Sa, IL-18, IL-2, and CCL5. In some embodiments the proteins of the nanogel are cytokines fused to Fc domains (e.g., human IgG1 Fc domains).

Proteins of the nanogel may be modified in a binary solvent that is compatible with proteins. For example, in some embodiments, a binary solvent includes aqueous buffer and a water-miscible organic solvent, such as phosphate buffered saline (PBS) and dimethyl sulfoxide (DMSO), and is used for reversibly modifying a protein with a degradable linker. The ratio of the aqueous buffer (e.g., PBS) to organic phase (e.g., DMSO) may be within a range of about 50:1 to about 20:1. In some embodiments, the ratio of inorganic phase to organic phase is about 30:1 to about 20:1, or about 25:1 (e.g., 500 μL:20 μL). In some embodiments, the organic solvent is less than 5% of the total volume of the binary buffer or the reaction containing the binary buffer.

Methods of producing protein nanogels are described in US20150110740 A1, incorporated herein by reference.

Liposomes

In some embodiments, a nanostructure is a liposome. Liposomes are closed vesicles comprising at least one lipid bilayer and an internal aqueous compartment. Liposomes may be anionic, neutral or cationic. They may be unilamellar or multilamellar. Liposomes may comprise, without limitation, unilamellar vesicle lipids, multilamellar vesicle lipids and extruded lipids including DOTMA, DOTAP, DOTIM, DDAB, alone or together with cholesterol to yield DOTMA and cholesterol, DOTAP and cholesterol, DOTIM and cholesterol, and DDAB and cholesterol. Methods for preparation of multilamellar vesicle lipids are known in the art (see, e.g., U.S. Pat. No. 6,693,086, the teachings of which relating to multilamellar vesicle lipid preparation are incorporated herein by reference). Extruded lipids are prepared in a similar manner but are then extruded through filters of decreasing size, as described in Templeton et al., *Nature Biotech*, 15:647-652, 1997, the teachings of which relating to extruded lipid preparation are incorporated herein by reference.

Liposomes may be surface modified during or after synthesis to include reactive groups complementary to the reactive groups on the carrier cells. Such reactive groups include without limitation maleimide groups. As an example, liposomes may be synthesized to include maleimide conjugated phospholipids such as without limitation DSPE-MaL-PEG2000.

In some embodiments, a nanostructure is an interbilayer-crosslinked multilamellar vesicles (ICMVs). ICMVs are a form of multilamellar lipid vesicle (MLV). MLVs are nano- or microspheres having a shell that is comprised of two or more concentrically arranged lipid bilayers. As used herein, adjacent or apposed lipid bilayers (or lipid bilayer surfaces) intend bilayers or surfaces that are in close proximity to each other but that are otherwise distinct and typically physically separate. This term does not typically mean the relationship between the two monolayers of a single bilayer.

Like the stabilized MLV described above, ICMV are nano- or microspheres having a shell that is comprised of two or more concentrically arranged lipid bilayers that are conjugated to each other as described herein. The number of lipid bilayers in the stabilized multilamellar vesicles, including the ICMV, may vary from about 2-30, but is more commonly in the range of 2-15. The bilayers are typically comprised of lipids having hydrophilic heads and hydrophobic tails that are arranged in a manner similar to a cell membrane (i.e., with the hydrophilic heads exposed to typically an aqueous environment and the hydrophobic tails buried in the bilayer).

ICMVs are stabilized via crosslinks (e.g., covalent crosslinks) between their lipid bilayers, and they are therefore referred to as "interbilayer crosslinked" MLV. As used herein, this means that at least two lipid bilayers in the shell of the vesicle are crosslinked to each other. The crosslinked bilayers are typically those that are apposed or adjacent to each other. Most or all of the lipid bilayers in the shell may be crosslinked to their apposing lipid bilayer in the shell. There may be one or more crosslinks between lipid bilayers. Typically, there may be numerous crosslinks between lipid bilayers. The arrangement and positioning of such crosslinks may be random or non-random. The degree of crosslinks (and thus the resultant stability of the vesicles) may depend upon the proportion of functionalized lipids (or other lipid bilayer components) used to make the vesicles and the crosslinking conditions (including, for example, time of incubation of the vesicles with a crosslinker). It should be understood that the higher the proportion of functionalized lipids (or other lipid bilayer components) in the vesicles, the more crosslinks that are formed, all other factors and parameters being equal. Similarly, the more favorable the conditions towards crosslinking, the greater degree of crosslinking that is achieved.

Methods of Producing Nanostructures

Provided herein are methods of producing nanostructures. An example of a nanostructure is a protein nanogel, such as a protein nanogel that contains intact, biologically-active proteins but does not contain a carrier (e.g., albumin, BSA). In some embodiments, a method of producing a carrier-free, biologically-active protein nanogel comprises contacting a protein with a degradable linker under conditions that permit reversible covalent crosslinking of proteins to each other through the degradable linker, thereby producing a carrier-free, biologically-active protein nanogel. In some embodiments, a method further comprises contacting the protein nanogel with a polymer under conditions that permit crosslinking of the polymer to proteins of the protein nanogel, thereby producing a carrier-free, biologically-active protein-polymer nanogel. In some embodiments, a plurality of protein nanogels or a plurality of protein-polymer nanogels is produced.

Typically, conditions that permit reversible covalent crosslinking of proteins to each other through a degradable linker include contacting the proteins with degradable linkers at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, proteins are incubated with the degradable linkers in an aqueous buffer (e.g., PBS) at a temperature of 4° C. to 25° C. (e.g., room temperature). In some embodiments, proteins are incubated with the degradable linkers in an aqueous buffer (e.g., PBS) at a temperature of no greater than 30° C. In some embodiments, conditions that permit reversible covalent crosslinking of proteins to each other through a degradable linker include contacting proteins with degradable linkers for 30 minutes to two hours, or 30 minutes to one hour (e.g., 30, 35, 40, 45, 50, 55 or 60 minutes). In some embodiments, proteins are incubated with the degradable linkers in an aqueous buffer (e.g., PBS) for 30 minutes to two hours, or 30 minutes one hour.

In some embodiments, the concentration of the protein in the aqueous buffer is 10 mg/mL to 50 mg/mL. For example, the concentration of the protein in an aqueous buffer may be 10 mg/mL, 15 mg/mL, 20 mg/mL, 25 mg/mL, 30 mg/mL, 35 mg/mL, 40 mg/mL, 45 mg/mL or 50 mg/mL protein/aqueous buffer).

In some embodiments, the weight percentage of protein in a carrier-free, biologically-active protein nanogel or protein-polymer nanogel is at least 75% w/w. For example, the weight percentage of protein in the carrier-free, biologically-active protein-polymer nanogels is at least 80% w/w, at least 85% w/w, at least 90% w/w, or at least 95% w/w. In some embodiments, the weight percentage of protein in a carrier-free, biologically-active protein nanogel or protein-polymer nanogel is 75% w/w to 90% w/w, 80% w/w to 90% w/w, or 85% w/w to 90% w/w.

Conditions that permit crosslinking of a polymer to proteins of a protein nanogel include contacting the protein nanogel with a polymer at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, protein nanogels are incubated with the polymers in an aqueous buffer (e.g., PBS) at a temperature of 4° C. to 25° C. (e.g., room temperature). In some embodiments, protein nanogels are incubated with the polymers in an aqueous buffer (e.g., PBS) at a temperature of no greater than 30° C. In some embodiments, conditions that permit crosslinking of a polymer to proteins of a protein nanogel include contacting the protein nanogel with a polymer for 30 minutes to two hours, or 30 minutes to one hour (e.g., 30, 35, 40, 45, 50, 55 or 60 minutes). In some embodiments, protein nanogels are incubated with the polymer in an aqueous buffer (e.g., PBS) for 30 minutes to two hours, or 30 minutes one hour.

In some embodiments, methods of the present disclosure specifically exclude contacting a protein with a degradable linker in the presence of an organic solvent (e.g., an alcohol such as ethanol or isopropanol). In some embodiments, methods of the present disclosure specifically exclude contacting a protein nanogel with a polymer in the presence of an organic solvent (e.g., an alcohol such as ethanol or isopropanol). Organic solvents may adversely affect the biological activity of the proteins.

Other methods of producing nanostructures of the present disclosure may comprise modifying a protein with a degradable linker and polymerizable functional groups, and polymerizing the polymerizable functional groups with a crosslinker and soluble fluoride.

Proteins of the disclosure may be modified with, or conjugated to, a degradable linker such as, for example, a redox responsive linker. The modification may, in some embodiments, be a covalent modification. Polymerizable functional groups may be polymerized with a crosslinker in the presence of a soluble fluoride catalyst. In some embodiments, the crosslinker is a polymer (e.g., silane-PEG-silane). In some embodiments, the soluble fluoride is sodium fluoride. In some embodiments, the soluble fluoride is potassium fluoride.

Nanostructure Surface Coatings

Ligands for Binding Cell Curface Coupling Receptors

A ligand is any molecule that binds to another molecule, such as a cell surface receptor (e.g., a cell surface coupling receptor, such as CD45). Examples of ligands include antibodies (also referred to as immunoglobulins), soluble proteins receptors (e.g., CD22; Sgroi et al. *Proc. Natl. Acad. Sci. USA,* 92:4026-30, 1995), cytokines, peptides, small molecules, co-factors, hormones and neurotransmitters. Other protein binding partners are contemplated herein. Ligands can be incorporated in a nanoparticle or liposome to facilitate coupling of the nanoparticle or liposome to a carrier cell.

The term "antibody," as used herein, includes antibodies typically comprising two large heavy chains and two small light chains, antibody fragments (e.g., fragment antigen-binding (Fab) and fragment crystallizable (Fc)) and recombinant proteins containing antibody fragments (e.g., antigen-binding portions), unless otherwise indicated. An antibody may be a monoclonal antibody or a polyclonal antibody. In some embodiments, an antibody is a human antibody or a humanized antibody.

In some embodiments, a ligand is an antibody, such as an anti-CD45 antibody. In some embodiments, the anti-CD45 antibody is a human monoclonal anti-CD45 antibody. In some embodiments, the monoclonal anti-CD45 antibody is selected from the group consisting of BC8 (ACCT©: HB-10507™), 4B2, 9.4 (ATTC©: HB-10508™) and GAP8.3 (ATTC©: HB-12™). Thus, in some embodiments, a nanostructure (e.g., protein nanogel or liposome) is linked to an anti-CD45 antibody. In some embodiments, a protein nanogel comprising a cytokine (e.g., IL-2, IL-15, IL-15-SA, or a combination thereof) is linked to an anti-CD45 antibody, and then coupled to a carrier cell (e.g., T cell) expressing CD45.

A nanostructure, in some embodiments, may comprise 10 to 10000, or more ligands, depending, in part, on the size of the nanostructure. For example, a nanostructure may comprise 10 to 10000, 10 to 1000, 10 to 100 ligands, 100 to 10000, 100 to 1000, or 1000 to 10000 ligands.

In some embodiments, a ligand is linked to a nanostructure through a crosslinking reaction. In some embodiments, for example, where the nanostructure is a protein nanogel, the same crosslinker used to produce the protein nanogel may be used to incorporate the ligand.

In some embodiments, a ligand is linked to a nanostructure (e.g., antibodies, such as anti-CD45) with a permanent (e.g., irreversible) linker. In some embodiments, the linker contains two N-hydroxysulfosuccinimide (sulfo-NHS) groups. In some embodiments, the linker contains two maleimide groups, or other reactive groups known in the art for coupling molecules to antibodies. In some embodiments the linker is a reversible linker (e.g.: a redox responsive linker that degrades in the presence of a reducing agent (e.g.: glutathione, GSH) under physiological conditions).

Nanostructures comprising ligands may be coupled to carrier cells through a "coupling reaction," as described elsewhere herein, which may be covalent or non-covalent. In some embodiments, a nanostructure is coupled to a carrier cell through free surface thiols, as described, for example, in U.S. Patent Application Publication No. 2011/0293705.

Polycations

Some aspects of the present disclosure provide nanostructures (e.g.: nanogels) comprising on their surface a polycation. A polycation is a molecule or chemical complex having positive charges at several sites. Generally, polycations have an overall positive charge. Examples of polycations for use in accordance with the present disclosure include, without limitation, polylysine (poly-L-lysine and/or poly-D-lysine), poly(argininate glyceryl succinate) (PAGS, an arginine-based polymer),), polyethyleneimine, polyhistidine, polyarginine, protamine sulfate, polyethylene glycol-b-polylysine (PEG-PLL), or polyethylene glycol-g-polylysine. Polycations may be used, as provided herein, to improve adherence of a nanoparticle to a carrier cell (e.g.: T cell) to increase efficiency of a coupling reaction. Specifically, polycations, may be used to increase loading of a nanostructure (e.g.: protein nanogel) to a carrier cell. Polycations may also be used to increase the coupling or coupling efficiency of a nanostructure to a carrier cell. It is thought that polycations enhance electrostatic interactions between negatively-charged ions of the cell membrane and positively-charged surface ions of the nanogel.

In some embodiments, a polycation is added to the surface of a nanogel prior to coupling the nanogel to the surface of a carrier cell via a cell surface coupling receptor. In some embodiments, a polycation (e.g., polyethylene glycol-b-polylysine or PEG-PLL) is added to the surface of a nanogel prior to coupling the nanogel to the surface of a cell without a cell surface coupling receptor. In some embodiments the polycation is polyethylene glycol-b-polylysine. In some embodiments the polycation is added to a nanogel prior to coupling the nanogel to the surface of a carrier cell with a cell surface coupling receptor. In some embodiments the polycation is added to a nanogel with or without anti-CD45.

In some embodiments, adding a polycation to a nanostructure increases the coupling efficiency (e.g., efficiency of coupling a nanogel to a cell) to at least 50%. For example, adding a polycation to a nanostructure may increase the coupling efficiency that coupling efficiency to 50%, 55%, 60%, 65%, 70%, 75%, 80%, 85%, 90% or 95%. In some embodiments, adding a polycation to a nanostructure increases the coupling efficiency to 60% to 90%, 70% to 90%, or 80% to 90%.

Cell Surface Coupling Receptors for Carrier Cell Coupling

Cell surface receptors (e.g., transmembrane receptors) are proteins that mediate communication between a cell and its extracellular environment. Extracellular ligands, including cytokines, growth factors, hormones, neurotransmitters and cell recognition molecules, bind to a cognate receptor, triggering conformational changes that transduce an extracellular signal, initiating intracellular signaling pathways. Cell surface receptors regulate a number of biological pathways responsible for growth, differentiation, proliferation and survival. Both T cells and B cells contain cell surface receptors responsible for activating the cells.

As indicated above, a "cell surface coupling receptor" refers to a molecule (i.e.: cell surface receptor) located at the surface of a cell (e.g.: a carrier cell) that binds to and maintains cell surface localization of a cognate ligand (e.g., a ligand linked to a nanoparticle). The cell surface coupling receptor is a cell surface receptor that stably couples ligands to the cell surface with little or no internalization over time. In certain aspects, cell surface coupling receptors exhibit prolonged cell surface retention and/or long cell surface half-life. In certain aspects cell surface coupling receptors are slowly-internalizing T-cell surface proteins. In certain aspects the cell surface coupling receptor is a slowly-internalizing receptor. Thus, aspects of the present disclosure provide compositions comprising a nanostructure linked to the surface of a carrier cell (e.g.: a nucleated carrier cell) via a binding interaction between a cell surface coupling receptor on the carrier cell and a cognate ligand located on the nanostructure.

In some embodiments, a cell surface coupling receptor (e.g., CD45), when bound to a cognate ligand (e.g., anti-CD45 antibody), stably couples a nanostructure to a carrier cell. In some embodiments, the nanostructure coupled to the carrier cell with a cell surface coupling receptor exhibits prolonged surface retention. In some embodiments, the nanostructure coupled to the carrier cell with a cell surface coupling receptor exhibits a long cell surface half-life.

In some embodiments, a cell surface coupling receptor (e.g., CD45), when bound to a cognate ligand (e.g., anti-CD45 antibody), remains at the carrier cell surface (i.e., is not internalized) for at least 24 hours. For example, a cell surface coupling receptor bound to a cognate ligand may remain at the cell surface for at least 30 hours, at least 36 hours, at least 42 hours, at least 48 hours, at least 54 hours, at least 60 hours, at least 66 hours, at least 72 hours. In some embodiments, at least 50% (e.g., at least 60%, at least 70%, at least 80%, at least 90%, or at least 95%) of the cell surface coupling receptor bound to a cognate ligand remains at the cell surface for at least at least 24 hours (e.g., at least 30 hours, at least 36 hours, at least 42 hours, at least 48 hours, at least 54 hours, at least 60 hours, at least 66 hours, at least 72 hours).

A non-limiting example of a cell surface coupling receptor is CD45. CD45 is a 147 kDa single chain transmembrane member of the protein tyrosine phosphatase (PTP) family, expressed in both T and B cells, and is required for T and B cell activation. It contains a highly glycosylated extracellular domain, a single transmembrane segment, and two tandem intracellular catalytic domains. The two catalytic domains are involved in src and JAK kinase signaling and interact with antigen-receptor complexes. Thus, in some embodiments, a nanostructure containing (e.g., at its surface) an anti-CD45 antibody is linked, or coupled, to the surface of a carrier cell expressing CD45. Internalization of such cell-surface receptors is minimal. In some embodiments, 50% or more (or more than 50%) of liposomes or nanoparticles (e.g.: nanogels) linked to a carrier cell (e.g., T cell) expressing a cell surface coupling receptor (e.g., CD45) are maintained at the surface of the cell (i.e., not internalized) for at least 24 hours (e.g., 24, 30, 36, 42, 48, 54, 60, 66, 72 hours). For example, more than 55%, more than 60%, more than 65%, more than 70%, more than 75%, more than 80%, more than 85%, or more than 90% of liposomes or nanoparticles (e.g.: nanogels) linked to a cell expressing a cell surface coupling receptor are maintained at the surface of the carrier cell for at least 24 hours. In some embodiments, a cell surface coupling receptor is a human (Homo sapiens) CD45 receptor. Examples of nucleic acids encoding human CD45 receptors include, without limitation, NCBI Reference Sequence Nos: NM_080921.3, NM_002838.4, NR_052021.1 and NM_001267798.1.

In some embodiments, the cell surface coupling receptor is a recombinant receptor (e.g., comprising nucleic acid obtained from multiple sources).

In some embodiments, a carrier cell expresses at least 2 (e.g., at least 3, at least 4 or at least 5) cell surface coupling receptors, including, for example, CD45.

In some embodiments, a carrier cell is engineered to express a cell surface coupling receptor (e.g., CD45). A cell is engineered if it contains, for example, an engineered nucleic acid. An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing.

Thus, in some embodiments, a carrier cell (e.g., a T cell) is engineered to express CD45. A carrier cell may contain, for example, an engineered nucleic acid encoding CD45. Such nucleic acids may be produced using standard molecular biology methods (see, e.g., Green and Sambrook, *Molecular Cloning, A Laboratory Manual*, 2012, Cold Spring Harbor Press). An engineered nucleic acid may be introduced into a cell by conventional methods, such as, for example, electroporation (see, e.g., Heiser W. C. *Transcription Factor Protocols: Methods in Molecular Biology*™ 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), transduction, conjugation, or microinjection of purified nucleic acid (e.g., DNA) directly into the nucleus of the cell (see, e.g., Capecchi M. R. *Cell.* 1980 November; 22(2 Pt 2): 479-88).

Carrier Cells for Coupling to Nanostructures

Aspects of the present disclosure provide compositions comprising a nanostructure (e.g.: protein nanogel or liposome) stably bound to a carrier cell (e.g., nucleated carrier cell) (or more simply, "a cell"). Carrier cells are cells to which nanoparticles are conjugated and which, when administered in vivo, typically home to target site(s). Suitable target cells are chosen based on their homing potential, their cell surface phenotype (for conjugation to the nanoparticles). Cells, in some embodiments, may be T cells (also referred to as T lymphocytes), B cells or natural killer (NK) cells, and hematopoietic progenitor cells including, without limitation, murine lineage-negative, Sca-1-positive and c-kit-positive cells and their human counterparts. Substantial levels of free thiol (—SH) groups exist on the surfaces of T cells, B cells and hematopoietic progenitor cells, thereby facilitating conjugation of nanostructures to such cells.

Carrier cells, in some embodiments, can extravasate from blood vessels (particularly when administered by intravenous injection) and thereby enter target tissues or organs. Red blood cells typically are not able to exit the blood stream. Accordingly, one important class of carrier cells includes nucleated carrier cells. Thus, in some embodiments, carrier cells are not red blood cells. In other embodiments, carrier cells are red blood cells.

Some embodiments of the present disclosure refer to isolated carrier cells. Isolated carrier cells are cells that have been separated from the environment in which they naturally occur (i.e., they are not present in vivo). T cells in vitro are an example of an isolated carrier cell. It should be understood that carrier cells may be isolated from their in vivo environment, conjugated to nanostructures of the present disclosure, and then re-introduced in vivo. Such carrier cells are still considered to be isolated cells.

The carrier cells, in some embodiments, are autologous to a subject being treated. In other embodiments, the carrier cells are non-autologous (yet preferably major histocompatibility complex (MHC) matched cells).

The carrier cells typically have a half-life in vivo, following administration (or re-infusion, in some instances) of at least 48 hours, at least 3 days, at least 4 days, at least 5 days, at least 6 days, at least 7 days, or more.

The carrier cells, in some embodiments, are genetically engineered to express one or more factors including, without limitation, co-stimulatory molecules or receptors including chimeric receptors. In other embodiments, the carrier cells are not genetically engineered. In some embodiments, the carrier cells are isolated and naturally occurring (i.e., they have not been genetically or otherwise engineered).

Depending on their nature and function, the carrier cells, in some embodiments, are manipulated prior to conjugation with the nanostructures. The carrier cells, however, need not be surface-modified in order to facilitate conjugation of the nanostructures. In some of embodiments, instead, reactive groups that normally exist on the carrier cell surface are used without having to incorporate reactive groups or other entities onto the cell surface. As a result, such carrier cells do not require the presence of exogenous entities such as antibodies or antibody fragments, among others, on their surface in order to conjugate to nanostructures.

Such manipulation may also involve activation of the carrier cells, as is routinely performed for T cells. The carrier cells may, in some embodiments, be expanded and/or activated (or stimulated, as the terms are used interchangeably herein) in vitro prior to mixing with nanostructures. Expansion and activation protocols may vary depending on the carrier cell type but can include incubation with one or more cytokines, incubation with one or more cell types, and incubation with one or more antigens. If the carrier cell is a T cell, then activation may be performed by incubating the T cells with IL-2, IL-15, IL-15 superagonist (IL-15SA or Il-15Sa), costimulatory molecules such as B7, B7.2, CD40, antibodies to various T cell surface molecules including antibodies to cell surface receptors, anti-CD3 antibodies, anti-CD28 antibodies, anti-CTLA-4 antibodies, anti-CD40L antibodies, and the like. In some embodiments, the carrier cells and more particularly the T cells, are not coated with exogenous antibodies on their cell surface (i.e., the cells have not been contacted with antibodies or antibody fragments in vitro prior to administration).

Expansion may be measured by proliferation assays involving incorporation of radiolabeled nucleotides such as tritiated thymidine. Activation may be measured by production of cytokines such as IL-2, gamma-IFN, IL-1, IL-4, IL-6 and TNF, among others. Other ways of measuring expansion and activation are known in the art and may be used in accordance with the disclosure.

Carrier cells may be selected prior to administration to a subject in order to enrich and thus administer higher numbers of such cells in smaller volumes and/or to remove other, potentially unwanted, cells from the administered composition. Selection may involve positive or negative selection including, for example, column or plate based enrichment protocols that are known in the art.

The carrier cells may be eukaryotic cells, such as mammalian cells (e.g., human cells). Alternatively, they may be non-mammalian cells. In still other embodiments, the carrier cells may be prokaryotic cells (e.g., bacterial cells). Several bacterial cell types are of particular interest. For example, attenuated *Salmonella typhimurium* is under study as a candidate vector for oral vaccine delivery (Xiang et al., *Immunol Rev* 222:117, 2008; and Iweala et al., *J Immunol* 183(4):2252, 2009) and engineered *E. coli* bacteria have been shown to be capable of specific homing to poorly oxygenated tumors (Cheong et al., *Science* 314(5803):1308, 2006). Bacteria offer new modes of administration and tissue site targeting possibilities, such as oral administration and the ability to target therapeutics to the gut and gut-associated lymphoid tissues. Such microbial vectors may offer advantages relative to autologous host cells in terms of creating off-the-shelf ready-to-use cell-nanoparticles systems. Particles conjugation to microbes can be achieved using the same suite of chemical strategies described for mammalian cells. In some instances, temporary removal of flagellar coats of microbes (e.g., via simple mechanical shearing as described by Rosu et al., *J Bacteriol* 188(14):5196, 2006) can be used to achieve optimal conjugation of particles to microbe cell bodies.

T Cells

In some embodiments, cells of the present disclosure are T cells. T cells are lymphocytes of a type produced or processed by the thymus gland and actively participating in the immune response. T cells can be distinguished from other lymphocytes, such as B cells and natural killer cells (NK cells), by the presence of a T-cell receptor (TCR) on the cell surface. Examples of T cells for use in accordance with the present disclosure include T helper cells ($T_H$ cells, CD4$^+$ T cells), cytotoxic T cells ($T_C$ cells, CTLs, CD8$^+$ T cells), memory T cells, suppressor T cells and natural killer T cells (NKT cells).

T helper cells aid other white blood cells in immunologic processes, including the maturation of B cells into plasma cells and memory B cells, and the activation of cytotoxic T cells and macrophages. They are activated by the presentation of peptide antigens by MHC class II molecules expressed on the surface of antigen-presenting cells. Upon activation, T helper cells secrete cytokines that further aid the immune response. T helper cells can differentiate into subtypes, which secrete different cytokines, causing different immune responses.

Cytotoxic T cells recognize their targets by binding to antigens associated with MHC class I molecules, which are found on the surfaces of all nucleated cells. They then destroy the virus-infected or tumor cells. Cytotoxic T cells are also implicated in transplant rejection. IL-10, adenosine, and other molecules secreted by regulatory T cells maintain the cytotoxic T cells in an inactive anergic state, preventing autoimmune diseases.

Memory T cells, which may be either CD4$^+$ or CD8$^+$, persist after an infection has been resolved. When re-exposed to their cognate antigen, they expand to large numbers of effector T cells to eliminate the pathogen more efficiently. Suppressor T cells quell T cell-mediated immunity at the end of an immune reaction and suppress autoreactive T cells that escaped negative selection in the thymus. Together with helper T cells, they constitute the regulatory T cells.

Natural killer T cells (not to be confused with natural killer cells, discussed below) link the adaptive and innate immune systems. Natural killer T cells recognize glycolipid antigen presented by CD1d, instead of antigens presented by MHC molecules. Upon activation, natural killer T cells are able to produce cytokines and release cytolytic molecules.

B Cells

In some embodiments, cells of the present disclosure are B cells. B cells are involved in humoral immunity in the adaptive immune system. They are distinguishable by the B cell receptors (BCRs) present on their outer surfaces. B cells make antibodies in response to antigens, work as antigen-presenting cells, and develop into memory B cells after activation stemming from antigen interaction. In addition, B cells secrete cytokines which are used in immune regulatory functions. B cells circulate in the blood and lymphatic system, performing immune surveillance. They do not produce antibodies until they have been fully activated. The B cell receptor (BCR), a membrane-bound immunoglobulin present on the surface of the B cell, binds to one specific antigen. B cells are activated either in a T cell-dependent manner or a T cell-independent manner. Upon activation, a B cell becomes a plasma B cell or a memory B cell. A B cell may also undergo an intermediate differentiation step, whereby it hypermutates the variable region of its immunoglobulin gene and may undergo class switching. Regulatory B cells secrete IL-10 and TGF-β and are involved in immune regulation via various mechanisms.

T and B cells may be harvested from the peripheral blood of a subject.

Natural Killer Cells

In some embodiments, cells of the present disclosure are Natural killer (NK) cells. Natural killer cells are cytotoxic lymphocytes of the innate immune response. They often lack antigen-specific cell surface receptors, and are able to react immediately without prior exposure to the pathogen. They contain viral infections while the adaptive immune response generates antigen-specific cytotoxic T cells to clear the infection completely. Small granules in their cytoplasm include perforin and granzymes, which are proteases. When these molecules are released in close proximity to the target cell, the perforin creates pores in the cell membrane of the target cell through which the granzymes and other associated molecules can enter, resulting in apoptosis or osmotic cell lysis. Natural killer cells also secrete α-defensins, antimicrobial molecules that directly kill bacteria by disrupting their cell walls, similar to the actions of neutrophils. Cytokines, including IL-12, IL-15, IL-18, IL-2 and CCL5, are released by cells in response to a viral infection and signal the NK cell to the presence of viral pathogens in the region. Natural killer cells secrete IFNγ and TNFα in response to viral infections. INFγ activates macrophages for phagocytosis and lysis, while TNFα promotes direct NK tumor cell killing. Natural killer cells also have an immune surveillance function, and are engaged in reciprocal interactions with dendritic cells, macrophages, T cells and endothelial cells.

Hematopoietic Progenitor Cells

Hematopoietic progenitor cells may be obtained from a number of sources including but not limited to cord blood, bone marrow, mobilized peripheral blood and, in some instances, differentiated embryonic stem cells.

Hematopoietic progenitor cells have been characterized in the art. Such cells in the human generally have minimally a CD34+ phenotype, although they may also be $CD59^+$, $Thy1/CD90^+$, $CD38^{lo/neg}$, $CD33^-$, and/or c-kit/$CD117^+$. They also are characterized as not expressing lineage specific markers. They can be harvested from bone marrow, cord blood or peripheral blood using affinity columns, magnetic beads, fluorescence activated cell sorting (FACS), some combination thereof, and the like. These cells have the ability to repopulate one or more hematopoietic lineages upon transplantation. Preferably, these cells repopulate more than one lineage, and even more preferably, all lineages. Repopulation or population of lineages as used herein refers to the differentiation of the stem cell into one or more lineages such that progeny of the stem cell contribute to the make-up of that lineage in the subject. It does not, however, require that the entire lineage compartment derive from the transplanted cells, however in some instances this may occur.

Isolated stem cells may be obtained by fractionating a heterogeneous cell population according to one or more markers, including by not limited to cell surface markers.

Chimeric Antigen Receptor (CAR) T Cells

T cells may be engineered to express chimeric antigen receptors (CARs). In their simplest form, CARs contain an antigen binding domain coupled with the transmembrane domain and the signaling domain from the cytoplasmic tail of the CD3 ζ chain. There is some evidence that the CD3 ζ chain is insufficient to fully activate transduced T cells. Accordingly, CARs preferably contain an antigen binding domain, a costimulatory domain, and a CD3 ζ signaling domain. Using a costimulatory domain in combination with the CD3 ζ signaling domain mimics the two-signal model of T cell activation. For example, some embodiments of the present disclosure relate to a chimeric antigen receptor comprising an antigen binding domain, a costimulatory domain, such as 4-1BB intracellular domain and a CD3 ζ signaling domain. In some embodiments, the antigen binding domain is fused to the costimulatory domain and a CD3 signaling domain via a linker, such as the CD8α hinge and transmembrane domain.

In some embodiments, CAR T cells are engineered to express antigen binding domains of a monoclonal antibody or antibody fragment, such as, for example, a Fab or an scFv. In some embodiments, a scFv is fused to the "BBz" chimeric antigen receptor, such as for example, huEGFRscFv-BBz chimeric antigen receptor (Johnson et. Al., 2015, Sci Transl Med., 7(275); US2014/0271635A1, incorporated herein by reference). The huEGFRscFv-BBz chimeric antigen receptor is a fusion protein designed based on the heavy and light chains of the EGFR inhibitor, cetuximab. Specifically, the heavy and light chains of cetuximab form a single-chain variable fragment that is fused to a portion of the extracellular and transmembrane domains of human CD8α, which links to the BBz signaling domain. The BBz domain comprises the intracellular domains of 4-1BB and CD3ζ.

The CAR antigen binding domain can be an antibody or antibody fragment, such as, for example, a Fab or an scFv. Non-limiting examples of anti-cancer antibodies include the following, without limitation:

trastuzumab (HERCEPTIN™ by Genentech, South San Francisco, Calif.), which is used to treat HER-2/neu positive breast cancer or metastatic breast cancer;

bevacizumab (AVASTIN™ by Genentech), which is used to treat colorectal cancer, metastatic colorectal cancer, breast cancer, metastatic breast cancer, non-small cell lung cancer, or renal cell carcinoma;

rituximab (RITUXAN™ by Genentech), which is used to treat non-Hodgkin's lymphoma or chronic lymphocytic leukemia;

pertuzumab (OMNITARG™ by Genentech), which is used to treat breast cancer, prostate cancer, non-small cell lung cancer, or ovarian cancer;

cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer;

IMC-1C11 (ImClone Systems Incorporated), which is used to treat colorectal cancer, head and neck cancer, as well as other potential cancer targets;

tositumomab and tositumomab and iodine $I^{131}$ (BEXXAR™ by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy;

$In^{111}$ ibirtumomab tiuxetan; $Y^{90}$ ibirtumomab tiuxetan; $In^{111}$ ibirtumomab tiuxetan and $Y^{90}$ ibirtumomab tiuxetan (ZEVALIN™ by Biogen Idec, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma;

EMD 7200 (EMD Pharmaceuticals, Durham, N.C.), which is used for treating for treating non-small cell lung cancer or cervical cancer;

SGN-30 (a genetically engineered monoclonal antibody targeted to CD30 antigen by Seattle Genetics, Bothell, Wash.), which is used for treating Hodgkin's lymphoma or non-Hodgkin's lymphoma;

SGN-15 (a genetically engineered monoclonal antibody targeted to a Lewisy-related antigen that is conjugated to doxorubicin by Seattle Genetics), which is used for treating non-small cell lung cancer;

SGN-33 (a humanized antibody targeted to CD33 antigen by Seattle Genetics), which is used for treating acute myeloid leukemia (AML) and myelodysplastic syndromes (MDS);

SGN-40 (a humanized monoclonal antibody targeted to CD40 antigen by Seattle Genetics), which is used for treating multiple myeloma or non-Hodgkin's lymphoma;

SGN-35 (a genetically engineered monoclonal antibody targeted to a CD30 antigen that is conjugated to auristatin E by Seattle Genetics), which is used for treating non-Hodgkin's lymphoma;

SGN-70 (a humanized antibody targeted to CD70 antigen by Seattle Genetics), that is used for treating renal cancer and nasopharyngeal carcinoma;

SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present invention are not limited to those described supra.

Agents for Use in Nanostructures

In some embodiments, the present disclosure provides methods for delivering an agent comprising administering to a subject a carrier cell covalently bound to a nanostructure that comprises an agent, wherein the cell does not substantially internalize the nanostructure and maintains the nanostructure on the cell surface, and wherein the agent is released from the nanostructure in vivo.

The present disclosure contemplates the delivery of agents to particular cells, and thus potentially to localized regions or tissues in vivo. As used herein, an "agent" is any atom or molecule or compound that can be used to provide benefit to a subject (including without limitation prophylactic or therapeutic benefit). The agents of particular interest, in some embodiments, are those that exert an effect on target cells, whether directly or indirectly. Some agents may exert their effects on tumor cells, pathogens, or pathogen-infected cells. The nature of the agent depends on the particular application, as should be apparent.

Nanostructures (eg: protein nanogels) may carry the agent internally including for example in pores or in a hollow core. The nanostructures may carry the agent internally and on its surface.

The present disclosure further contemplates that one or more agents may be used alongside the nanostructures, although not conjugated to or encapsulated within. For example, the nanostructures may be formulated together with one or more agents.

The agent may be without limitation a chemical entity, a protein, a polypeptide, a peptide, a nucleic acid, a virus-like particle, a steroid, a proteoglycan, a lipid, a carbohydrate, and analogs, derivatives, mixtures, fusions, combinations or conjugates thereof. The agent may be a pro-drug that is metabolized and thus converted in vivo to its active (and/or stable) form.

The agents may be naturally occurring or non-naturally occurring. Naturally occurring agents include those capable of being synthesized by the subjects to whom the particles are administered. Non-naturally occurring are those that do not exist in nature normally, whether produced by plant, animal, microbe or other living organism.

One class of agents that can be delivered in a localized manner using nanostructures includes chemical compounds that are non-naturally occurring, or chemical compounds that are not naturally synthesized by mammalian (and in particular human) cells.

A variety of agents that are currently used for therapeutic purposes can be delivered according to the present disclosure and these include without limitation immunomodulatory agents such as immunostimulatory agents, antigens (e.g., HPV protein), adjuvants, imaging agents, anti-cancer agents, anti-infective agents, and the like.

One particular class of agents is inhibitors of immunosuppression. Examples include Shp1/2 protein tyrosine phosphatase (PTPase) inhibitor (NSC-87877; CAS 56932-43-5), sunitinib, or other inhibitors of receptor tyrosine kinases, or p38 MAPK inhibitors including MAPK pathway inhibitors.

The p38 MAPK pathway inhibitor may be a RAF inhibitor such as a pan-RAF inhibitor or a selective RAF inhibitor. Examples of RAF inhibitors include RAF265, sorafenib, dabrafenib (GSK2118436), SB590885, PLX 4720, PLX4032, GDC-0879 and ZM 336372. The p38 MAPK pathway inhibitor may be a MEK inhibitor. Examples of MEK inhibitors include CI-1040/PD184352, AZD6244, PD318088, PD98059, PD334581, RDEA119, 6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile, trametinib (GSK1120212), and ARRY-438162.

The p38 MAPK pathway inhibitor may be an ERK inhibitor. Examples of ERK inhibitors include VTX11e, AEZS-131, PD98059, FR180204, and FR148083. Still other p38 MAPK inhibitors are Tocriset, SB239063, SB203580, pamapimod, dilmapimod, and PH797804.

Imaging or Diagnostic Agents. As used herein, an imaging agent is an agent that emits signal directly or indirectly thereby allowing its detection in vivo. Imaging agents such as contrast agents and radioactive agents that can be detected using medical imaging techniques, such as nuclear medicine scans and magnetic resonance imaging (MRI). Imaging agents for magnetic resonance imaging (MRI) include Gd(DOTA), iron oxide or gold nanoparticles; imaging agents for nuclear medicine include 201T1, gamma-emitting radionuclide 99 mTc; imaging agents for positron-emission tomography (PET) include positron-emitting isotopes, (18) F-fluorodeoxyglucose ((18)FDG), (18)F-fluoride, copper-64, gadoamide, and radioisotopes of Pb(II) such as 203 Pb, and 11In; imaging agents for in vivo fluorescence imaging such as fluorescent dyes or dye-conjugated nanoparticles. In other embodiments, the agent to be delivered is conjugated, or fused to, or mixed or combined with an imaging agent.

Immunostimulatory Agents. As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod, imidazoquinoline, nucleic acids comprising an unmethylated CpG dinucleotide, monophosphoryl lipid A or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Immunoinhibitory Agents. As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Anti-Cancer Agents. As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids. or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4, 5-trihydroxyphenyl), methyleneFpropanedinitrile, Herbimycin A, Daidzein (4',7-dihydroxyisoflavone), AG-126, trans-1-(3'-carboxy-4'-hydroxyphenyl)-2-(2",5"-dihydroxy-phenyl)ethane, or HDB A (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 (C23H24O8), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Protein Agents. Examples of protein agents for use in accordance with the present disclosure include, without limitation, antibodies, single chain antibodies, antibody fragments, enzymes, co-factors, receptors, ligands, transcription factors and other regulatory factors, some antigens (as discussed below), cytokines, chemokines, and the like. These protein agents may or may not be naturally occurring. Other proteins are contemplated and may be used in accordance with the disclosure.

In some embodiments, the protein agents of the disclosure are fusion proteins of a biologically active protein fused to an immunogloulin Fc domain, referred to as an Fc fusion protein (e.g., human IgG1 Fc fusion protein). In some embodiments, the biologically active protein of the nanogel is a cytokine, including, without limitation, IL-12, IL-15, IL-15-Sa, IL-18, IL-2, and CCL5. In some embodiments the proteins of the nanogel are cytokines fused to Fc domains (e.g., human IgG1 Fc domains).

In some embodiments, protein agents of the disclosure are immunomodulatory proteins (e.g., immunostimulatory or immunoinhibitory proteins). As used herein, an immunomodulatory protein is a protein that modulates (e.g., stimulates or inhibits) an immune response (including enhancing or reducing a pre-existing immune response) in a subject to whom it is administered, whether alone or in combination with another protein or agent. In certain embodiments of the disclosure immunomodulatory proteins are PD-L1, CTLA-4, IL-10 or TGF-beta.

In some embodiments, protein agents of the disclosure are immunostimulatory proteins. As used herein, an immunostimulatory protein is a protein that stimulates an immune response (including enhancing a pre-existing immune response) in a subject to whom it is administered, whether alone or in combination with another protein or agent. Examples of immunostimulatory proteins that may be used in accordance with the disclosure include, without limitation, antigens, adjuvants (e.g., flagellin, muramyl dipeptide), cytokines including interleukins (e.g., IL-2, IL-7, IL-15 (or superagonist/mutant forms of these cytokines), IL-15SA, IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Cytokines are a class of small proteins (~5-20 kDa) that are released by cells and affect the behavior of cells via cell signaling. Cytokines are produced by various cell types, including, without limitation, immune cells such as macrophages, B lymphocytes, T lymphocytes, and mast cells, and endothelial cells, fibroblasts, and a variety of stromal cells. A cytokine may be produced by more than cell type. Cytokines include, without limitation, chemokines, interferons, interleukins, lymphokines, and tumour necrosis factor. Other immunostimulatory proteins are contemplated and may be used in accordance with the disclosure.

In some embodiments the immunostimulatory protein is IL-15SA. The combination of human IL15 with soluble human IL-15Rα generates a complex termed IL-15 superagonist (IL-15SA) that possesses greater biological activity than human IL-15 alone.

Soluble human IL-15Rα, as well as truncated versions of the extracellular domain, has been described in the art (Wei et L. 2001 *J of Immunol.* 167: 277-282). The amino acid sequence of human IL-15Rα is set forth in SEQ ID NO: 9, Accordingly, some aspects of the disclosure relate to IL-15SA comprising a complex of human IL-15 and soluble human IL-15Rα molecules. In some aspects of the disclosure, IL-15SA comprises a complex of human IL-15 and soluble human IL-15Rα comprising all or a portion of the extracellular domain, without the transmembrane air cytoplasmic domain. In some aspects of the disclosure, IL-15SA comprises a complex of human IL-15 and soluble human IL-15Rα comprising the full extracellular domain or a truncated form of the extracellular domain which retains IL-15 binding activity. Some aspects of the disclosure relate to IL-15SA comprising a complex of human IL-15 and soluble human IL-15Rα comprising a truncated form of the extracellular domain which retains IL-15 binding activity, such as amino acids 1-60, 1-61, 1-62, 1-63, 1-64 or 1-65 of human IL-5Rα. In some aspects of the disclosure, IL-15SA comprises a complex of human IL-15 and soluble human IL-15Rα comprising a truncated form of the extracellular domain which retains IL-15 binding activity, such as amino acids 1-80, 1-81, 1-82, 1-83, 1-84 or 1-85 of human IL-15Rα. In some aspects of the disclosure, IL-15SA comprises a complex of human IL-15 and soluble human IL-15Rα comprising a truncated form of the extracellular domain which retains IL-15 binding activity, such as amino acids 1-180, 1-181, or 1-182 of human IL-15Rα.

Some aspects of the disclosure relate to IL-15SA comprising a complex of human IL-15 and soluble human IL-15Rα comprising a truncated form of the extracellular domain which retains IL-15 binding activity and comprises a Sushi domain. The Sushi domain of IL-15Rα is described in the art as approximately 60 amino acids in length and comprises 4 cysteines. (Wei el al., 2001). Truncated forms of soluble human IL-15Rα which retain IL-15 activity and comprise a Sushi domain are useful in IL-15SA of the present disclosure.

Mutant forms of human IL-15 are known in the art. Accordingly, the present disclosure provides any of the foregoing IL-15SA complexes in which human IL-15 is wild-type or mutant IL-15 comprising one or more mutations (e.g., one or more amino acid substitutions, additions or deletions). An exemplary IL-15 mutant having increased biological activity relative to wild-type IL-15 for use in the IL-15SA of the present disclosure comprises an asparagine to aspartic acid substitution at amino acid 72 (N72D), (Zhu et al., 2009 *J of Immunol.* 183:3598.)

In any of the foregoing embodiments, the present disclosure relates to a complex comprising soluble human IL-15Rα expressed as a fusion protein, such as an Fc fusion as described herein (e.g., human IgG1 Fc), with IL-15. In some embodiments, IL-15SA comprises a dimeric human IL-15RαFc fusion protein (e.g., human IgG1 Fc) complexed with two human IL-15 molecules.

In some embodiments an IL-15SA cytokine complex comprises an IL-15 molecule comprising an amino acid sequence set forth in SEQ ID NO: 1, SEQ ID NO: 4, SEQ ID NO: 5, or SEQ ID NO: 6. In some embodiments, an IL-15SA cytokine complex comprises a soluble IL-15Rα molecule comprising a sequence of SEQ ID NO: 3, SEQ ID NO: 7 or SEQ ID NO: 8.

In some embodiments the IL-15SA is a cytokine complex comprising a dimeric IL-15RαFc fusion protein complexed with two IL-15 molecules. In some embodiments, IL-15-SA comprises a dimeric IL-15RαSu(Sushi domain)/Fc (SEQ ID NO: 2) and two IL-15N72D (SEQ ID NO: 1) molecules (also known as ALT-803, as described in US20140134128, incorporated herein by reference. In some embodiments, the IL-15SA comprises a dimeric IL-15RαSu/Fc molecule (SEQ ID NO: 2) and two IL-15 molecules (SEQ ID NO: 4). In some embodiments, the IL-15SA comprises a dimeric IL-15RαSu/Fc molecule (SEQ ID NO: 2) and two IL-15 molecules (SEQ ID NO: 5). In some embodiments, the IL-15SA comprises a dimeric IL-15RαSu/Fc molecule (SEQ ID NO: 2) and two IL-15 molecules (SEQ ID NO: 6).

In some embodiments, the IL-15SA comprises a dimeric IL-15RαSu/Fc molecule (SEQ ID NO: 2) and two IL-15 molecules comprising sequences selected from SEQ ID NO: 1, 4, 5, and 6.

In some embodiments, the IL-15SA comprises a soluble IL-15Rα molecule (SEQ ID NO: 3) and two IL-15 molecules (SEQ ID NO: 1). In some embodiments, the IL-15SA comprises a soluble IL-15Rα molecule (SEQ ID NO: 3) and two IL-15 molecules (SEQ ID NO: 4). In some embodiments, the IL-15SA comprises a soluble IL-15Rα molecule (SEQ ID NO: 3) and two IL-15 molecules (SEQ ID NO: 5). In some embodiments, the IL-15SA comprises a soluble IL-15Rα molecule (SEQ ID NO: 3) and two IL-15 molecules (SEQ ID NO: 6).

In some embodiments, the IL-15SA comprises a soluble IL-15Rα molecule (SEQ ID NO: 7) and two IL-15 molecules (SEQ ID NO: 1). In some embodiments, the IL-15SA comprises a soluble IL-15Rα molecule (SEQ ID NO: 7) and two IL-15 molecules (SEQ ID NO: 4). In some embodiments, the IL-15SA comprises a soluble IL-15Rα molecule (SEQ ID NO: 7) and two IL-15 molecules (SEQ ID NO: 5). In some embodiments, the IL-15SA comprises a soluble IL-15Rα molecule (SEQ ID NO: 7) and two IL-15 molecules (SEQ ID NO: 6).

In some embodiments, the IL-15SA comprises a soluble IL-15Rα molecule (SEQ ID NO: 8) and two IL-15 molecules (SEQ ID NO: 1). In some embodiments, the IL-15SA comprises a soluble IL-15Rα molecule (SEQ ID NO: 8) and two IL-15 molecules (SEQ ID NO: 4). In some embodiments, the IL-15SA comprises a soluble IL-15Rα molecule (SEQ ID NO: 8) and two IL-15 molecules (SEQ ID NO: 5). In some embodiments, the IL-15SA comprises a soluble IL-15Rα molecule (SEQ ID NO: 8) and two IL-15 molecules (SEQ ID NO: 6).

In some embodiments, the IL-15SA comprises a dimeric IL-15RαSu/Fc (SEQ ID NO: 2) molecule and two IL-15 molecules (SEQ ID NO: 5). In some embodiments, the IL-15SA comprises a dimeric IL-15RαSu/Fc (SEQ ID NO: 2) molecule and two IL-15 molecules (SEQ ID NO: 6).

In some embodiments, the IL-15SA comprises SEQ ID NO: 1 and SEQ ID NO: 3. In some embodiments IL-15SA comprises SEQ ID NO: 4 or SEQ ID NO: 5. In some embodiments the IL-15SA comprises SEQ ID NO: 4 and SEQ ID NO: 2. In some embodiments the IL-15SA comprises SEQ ID NO: 5 and SEQ ID NO: 2 In some embodiments the IL-15SA comprises SEQ ID NO: 6 and SEQ ID NO: 2. In some embodiments, the IL-15SA comprises SEQ ID NO: 4 and SEQ ID NO: 3. In some embodiments the IL-15SA comprises SEQ ID NO: 5 and SEQ ID NO: 3.

In some embodiments, protein agents of the disclosure are cancer antigens. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2, (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens are contemplated and may be used in accordance with the disclosure.

In some embodiments, the protein of the nanogel is human papillomavirus (HPV) protein.

In some embodiments, protein agents of the disclosure are antibodies or antibody fragments including, without limitation, bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

Anti-Infective Agents. The agent may be a prophylactic agent or an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Other anti-bacterials may be without limitation Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; B acitracin; B acitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin.

Anti-mycobacterial agents may be without limitation Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate or Trecator-SC (Ethionamide).

Anti-viral agents may be without limitation amantidine and rimantadine, ribivarin, acyclovir, vidarabine, trifluorothymidine, ganciclovir, zidovudine, retinovir, and interferons.

Anti-viral agents may be without limitation further include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime or integrase inhibitors.

Anti-fungal agents may be without limitation imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin).

Other anti-infective agents may be without limitation Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

Adjuvants. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, Leishmania elongation factor (a purified Leishmania protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be Toll-like receptor (TLR) ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod, resiquimod). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Compositions and Methods of Administration

Compositions provided herein comprise a nucleated carrier cell that homes to a tumor and is coupled to a nanostructure (e.g., a protein nanogel or a liposome) comprising an agent (e.g., a biologically active protein), wherein the carrier cell comprises a cell surface coupling receptor (e.g., CD45) and is coupled to the nanostructure with a ligand that binds the receptor or the carrier cell comprises a negatively charged cell membrane and the nanostructure comprises a polycation surface which interacts electrostatically with the cell membrane.

In certain aspects the composition comprises a carrier cell having a CD45 receptor and the carrier cell is coupled to the nanostructure having a ligand that binds the CD45 receptor. In certain aspects the ligand is an anti-CD45 monoclonal antibody.

In certain aspects the carrier cell comprises a negatively charged cell membrane and the nanostructure comprises a polycation surface which interacts electrostatically with the cell membrane. In certain aspects, the polycation is polylysine. In certain aspects, the polycation is polyethylene glycol-b-polylysine (PEG-PLL).

In some embodiments, the composition comprises a protein nanogel. In certain aspects the protein nanogel comprises a plurality of biologically active proteins reversibly and covalently crosslinked to each other through a degradable linker. In some embodiments, the degradable linker is a redox responsive linker that comprises a disulfide bond.

In some embodiments, the composition is a liposome. In certain embodiments the liposome comprises a plurality of biologically active proteins. In certain aspects the liposome is an interbilayer-crosslinked multilamellar or unilamellar vesicle.

In some embodiments, the composition comprises a carrier cell wherein the carrier cell is a T cell, a B cell a Natural Killer (NK) cell or a stem cell. In some aspects, the carrier cell is a T cell. In some aspects, the T cell is a CD8$^+$ T cell or a CD4$^+$ T cell. In some aspects, the T cell is an adoptively transferred T cell. In some aspects, the T cell is a chimeric antigen receptor (CAR) T cell.

In some embodiments, the composition comprises a nanostructure comprising biologically active protein wherein the biologically active protein is selected from the group consisting of antibodies, antibody fragments, soluble protein receptors and cytokines. In some aspects, the cytokine is IL-2, IL-15 or IL-15SA. In some aspects, the cytokine is IL-15-Sa. In some aspects, the IL-15Sa comprises a complex comprising a dimeric IL-15RαSu/Fc and two IL-15N72D molecules. In some aspects, the dimeric IL-15RαSu/Fc comprises an amino acid sequence set forth in SEQ ID NO: 1 and the IL-15N72D molecule comprises an amino acid sequence set forth in SEQ ID NO: 2.

In some embodiments the composition comprises a pharmaceutically acceptable carrier. In some aspects the composition is useful as a medicament for delivering a biologically active protein to a subject having a tumor.

Certain aspects of the disclosure provide methods of treating cancer in a subject comprising administering to a subject in need thereof a composition as described herein.

Certain aspects of the disclosure provide a composition comprising a nucleated carrier cell (e.g.: a T cell) that homes to a tumor and is coupled to a nanostructure comprising a biologically active protein, wherein (a) the carrier cell comprises a CD45 receptor and is coupled to the nanostructure with a ligand that binds the CD45 receptor; or (b) the carrier cell comprises a negatively charged cell membrane and the nanostructure comprises a polycation surface which interacts electrostatically with the cell membrane; or (c) the carrier cell comprises a CD45 receptor and is coupled to the nanostructure with a ligand that binds the CD45 receptor, and the carrier cell comprises a negatively charged cell membrane and the nanostructure comprises a polycation surface which interacts electrostatically with the cell membrane.

Certain aspects of the disclosure provide a composition comprising a nucleated carrier cell (e.g.: a T cell) comprising a CD45 receptor and a nanostructure comprising a biologically active protein, wherein carrier cell is coupled to the nanostructure with a ligand that binds the CD45 receptor.

Certain aspects of the disclosure provide a composition comprising a nucleated carrier cell (e.g.: a T cell) that homes to a tumor and is coupled to a nanostructure comprising a biologically active protein, wherein the carrier cell comprises a negatively charged cell membrane and the nanostructure comprises a polycation surface which interacts electrostatically with the cell membrane.

Certain aspects of the disclosure provide a composition comprising a nucleated carrier cell comprising a CD45 receptor and a protein nanogel, wherein the carrier cell is coupled to the protein nanogel with a ligand that binds the CD45 receptor, and wherein the protein nanogel comprises a plurality of biologically active proteins reversibly and covalently crosslinked to each other through a degradable linker.

Certain aspects of the disclosure provide a composition comprising a nucleated carrier cell (e.g.: a T cell) that homes to a tumor and is coupled to a protein nanogel, wherein the carrier cell comprises a negatively charged cell membrane and the protein nanogel comprises a polycation surface which interacts electrostatically with the cell membrane, and wherein the protein nanogel comprises a plurality of biologically active proteins reversibly and covalently crosslinked to each other through a degradable linker.

Certain aspects of the disclosure provide a composition comprising a nucleated carrier cell (e.g.: a T cell) comprising a CD45 receptor and a liposome comprises a plurality of biologically active proteins, wherein the carrier cell is coupled to the liposome with a ligand that binds the CD45 receptor.

The compositions provided herein may be used for a variety of biomedical and pharmaceutical applications. In some embodiments, the compositions are used for agent (e.g., drug) delivery in vivo for targeted immunotherapy. In some embodiments, the compositions are used in adoptive cell therapy. Adoptive cell therapy (ACT) is a highly personalized cancer therapy that typically involves administration to the cancer-bearing host of immune cells with direct anticancer activity. The invention contemplates administration of the compositions of the invention to subjects having or at risk of developing a cancer including for example a solid tumor cancer. Compositions, including pharmaceutical compositions, comprising protein nanostructures (e.g., protein nanogels) are provided herein. Also provided herein are compositions, including pharmaceutical composition, comprising a protein nanostructure (e.g., protein nanogels) coupled to a carrier cell. A composition can be administered to a subject in pharmaceutically-acceptable amounts and in pharmaceutically-acceptable compositions. The term "pharmaceutically acceptable" means a non-toxic material that does not interfere with the effectiveness of the biological activity of the active ingredients (e.g., biologically-active proteins of the nanostructures). Such compositions may, in some embodiments, contain salts, buffering agents, preservatives, and optionally other therapeutic agents.

Pharmaceutical compositions also may contain, in some embodiments, suitable preservatives.

Pharmaceutical compositions may, in some embodiments, be presented in unit dosage form and may be prepared by any of the methods well-known in the art of pharmacy.

Pharmaceutical compositions suitable for parenteral administration, in some embodiments, comprise a sterile aqueous or non-aqueous preparation of the nanostructures, which is, in some embodiments, isotonic with the blood of the recipient subject. This preparation may be formulated according to known methods. A sterile injectable preparation also may be a sterile injectable solution or suspension in a non-toxic parenterally-acceptable diluent or solvent.

Pharmaceutical compositions of the present disclosure are administered, in some embodiments, by a conventional route, including injection or by gradual infusion over time. Administration may, for example, be oral, intravenous, intraperitoneal, intramuscular, intracavity, intratumor, or transdermal.

Pharmaceutical compositions of the present disclosure are administered, in some embodiments, in effective amounts. An "effective amount" is that amount of any of the nanostructure provided herein that alone, or together with further doses and/or other therapeutic agents, produces a desired response (e.g., pseudoautocrine stimulation, augment T cell expansion and minimize systemic side effects of adjuvant drugs in vivo).

Pharmaceutical compositions of the present disclosure, in some embodiments, may be sterile and contain an effective amount of a nanostructure (e.g., nanogel), alone or in combination with another agent, for producing the desired response in a unit of weight or volume suitable for administration to a subject (e.g., human subject). The response can, for example, be measured by determining the physiological effects of the nano structure composition.

The doses of compositions administered to a subject may be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that subject/patient tolerance permits.

Methods of Administration

The disclosure also provides methods of administering compositions comprising carrier cells coupled to nanostructures in vivo to subjects. The methods of the disclosure can be practiced in a subject that is likely to benefit from delivery of an agent (e.g., a biologically active protein) as described herein. Human subjects are preferred subjects in some embodiments. Subjects also include animals such as household pets (e.g., dogs, cats, rabbits, ferrets), livestock or farm animals (e.g., cows, horses, pigs, sheep, chickens and other poultry), laboratory animals (e.g., mice, rats, rabbits), and the like. Subjects also include fish and other aquatic species.

The subjects to whom compositions are delivered may be normal, or healthy, subjects. Alternatively they may have or may be at risk of developing a condition that can be diagnosed or that can benefit from delivery of one or more agents as disclosed herein. Such conditions include cancer (e.g., solid tumor cancers), autoimmune disorders, allergies or allergic conditions, asthma, transplant rejection, and the like.

Tests for diagnosing various conditions embraced by the present disclosure are known in the art and will be familiar to the ordinary medical practitioner. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject having a cancer is a subject who has detectable cancer cells. A subject at risk of developing a cancer is a subject who has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (e.g., carcinogens) such as tobacco, asbestos, or other chemical toxins, and subjects previously treated for cancer and in apparent remission.

Subjects having an infection are those that exhibit symptoms thereof including without limitation fever, chills, myalgia, photophobia, pharyngitis, acute lymphadenopathy, splenomegaly, gastrointestinal upset, leukocytosis or leukopenia, and/or those in whom infectious pathogens or byproducts thereof can be detected.

A subject at risk of developing an infection is one that is at risk of exposure to an infectious pathogen. Such subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery, etc.

The subject may have or may be at risk of developing an infection such as a bacterial infection, a viral infection, a fungal infection, a parasitic infection or a mycobacterial infection. In these embodiments, the nanostructures may comprise an anti-microbial agent such as an anti-bacterial agent, an anti-viral agent, an anti-fungal agent, an anti-parasitic agent, or an anti-mycobacterial agent and the cell carriers (e.g., the T cells) may be genetically engineered to produce another agent useful in stimulating an immune response against the infection, or potentially treating the infection.

In some instances, the subjects to whom the compositions are administered are in need of hematopoietic reconstitution. Such subjects may have been exposed to a deliberate or accidental myeloablative event, including without limitation myeloablative chemotherapy and/or whole body radiation, as may be given as part of a therapeutic regimen for non-solid cancers or metastatic cancers. The disclosure provides method of administering to such subjects hematopoietic progenitor cells conjugated to nanostructures that comprise agents capable of stimulating the proliferation of the progenitor cells. In some instances, the agents may also be differentiating agents (i.e., agents that drive the progenitor cells and their progeny to differentiate, optionally towards all lineages or a subset of lineages. In other instances, the agents may be self-renewal agents (i.e., agents that drive the progenitor cells to self-renew). In yet other instances, the carrier cells may be conjugated to nanostructures that comprise both types of agents, whether such agents be in the same or different nanostructures. Moreover, the disclosure provides that exposure of the subject to these different agents may be staggered (e.g., exposure to the self-renewing agents may occur before exposure to the differentiating agents).

Methods of Treatment

Methods of Treating Cancer

The disclosure provides administration of compositions as described herein to subjects having or at risk of developing a cancer including for example a solid tumor cancer. The cancer may be carcinoma, sarcoma or melanoma. Carcinomas include without limitation to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Sarcomas are rare mesenchymal neoplasms that arise in bone (osteosarcomas) and soft tissues (fibrosarcomas). Sarcomas include without limitation liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), and chondrosarcoma.

Melanomas are tumors arising from the melanocytic system of the skin and other organs. Examples of melanoma include without limitation lentigo maligna melanoma, superficial spreading melanoma, nodular melanoma, and acral lentiginous melanoma.

The cancer may be a solid tumor lymphoma. Examples include Hodgkin's lymphoma, Non-Hodgkin's lymphoma, and B cell lymphoma.

The cancer may be without limitation bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma, or rhabdomyosarcoma.

Method of Treating Infection

The disclosure also provides methods of administrating compositions described herein to subjects having or at risk of developing an infection such as a bacterial infection, a viral infection, a fungal infection, a parasitic infection or a mycobacterial infection. The bacterial infection may be without limitation an *E. coli* infection, a *Staphylococcal* infection, a *Streptococcal* infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteriodes* infection, *H. pylori* infection, or anthrax infection.

The mycobacterial infection may be without limitation tuberculosis or leprosy respectively caused by the *M. tuberculosis* and *M. leprae* species.

The viral infection may be without limitation a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza A virus infection, H1N1 (swine flu) infection, respiratory syncytial virus infection, varicella-zoster virus infections, small pox infection, monkey pox infection, SARS infection or avian flu infection.

The fungal infection may be without limitation candidiasis, ringworm, histoplasmosis, blastomycosis, paracoccidioidomycosis, crytococcosis, aspergillosis, chromomycosis, mycetoma infections, pseudallescheriasis, or tinea versicolor infection.

The parasite infection may be without limitation amebiasis, *Trypanosoma cruzi* infection, *Fascioliasis*, *Leishmaniasis*, *Plasmodium* infections, *Onchocerciasis*, *Paragonimiasis*, *Trypanosoma brucei* infection, *Pneumocystis* infection, *Trichomonas vaginalis* infection, *Taenia* infection, *Hymenolepsis* infection, *Echinococcus* infections, *Schistosomiasis*, neurocysticercosis, *Necator americanus* infection, or *Trichuris trichuria* infection.

Methods of Treating Allergy and Asthma

The disclosure further provides administration of the compositions described herein to subjects having or at risk of developing an allergy or asthma. An allergy is an acquired hypersensitivity to an allergen. Allergic conditions include but are not limited to eczema, allergic rhinitis or coryza, hay fever, bronchial asthma, urticaria (hives) and food allergies, and other atopic conditions. Allergies are generally caused by IgE antibody generation against harmless allergens. Asthma is a disorder of the respiratory system characterized by inflammation, narrowing of the airways and increased reactivity of the airways to inhaled agents. Asthma is frequently, although not exclusively, associated with atopic or allergic symptoms. Administration of Th1 cytokines, such as IL-12 and IFN-gamma, according to the disclosure can be used to treat allergy or asthma.

Methods of Treating Autoimmune Disease

The disclosure provides administration of the compositions described herein to subjects having or at risk of developing an autoimmune disease. Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases are generally considered to be Th1 biased. As a result, induction of a Th2 immune response or Th2 like cytokines can be beneficial. Such cytokines include IL-4, IL-5 and IL-10.

Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

Transplant Therapy

The methods provided herein may also be used to modulate immune responses following transplant therapy. Transplant success is often limited by rejection of the transplanted tissue by the body's immune system. As a result, transplant recipients are usually immunosuppressed for extended periods of time in order to allow the transplanted tissue to survive. The disclosure provides localized delivery of immunomodulators, and particularly immunoinhibitory agents, to transplant sites in order to minimize transplant rejection. Thus, the disclosure provides administration of the compositions to subjects that are going to undergo, are undergoing, or have undergone a transplant. The foregoing lists are not intended to be exhaustive but rather exemplary. Those of ordinary skill in the art will identify other examples of each condition type that are amenable to prevention and treatment using the methods of the disclosure.

Effective Amounts, Regimens, Formulations

The compositions described herein are administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ.

The disclosure provides pharmaceutical compositions. Pharmaceutical compositions are sterile compositions that comprise cells, nanostructures and/or agent(s), preferably in a pharmaceutically-acceptable carrier. The term "pharmaceutically-acceptable carrier" means one or more compatible solid or liquid filler, diluents or encapsulating substances which are suitable for administration to a human or other subject as described herein. The term "carrier" denotes an organic or inorganic ingredient, natural or synthetic, with which the cells, nanostructures and agent(s) are combined to facilitate administration. The components of the pharmaceutical compositions are commingled in a manner that precludes interaction that would substantially impair their desired pharmaceutical efficiency.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides, or liposomes.

Other Embodiments

In a first aspect, the present disclosure provides a composition comprising a nucleated carrier cell that homes to a tumor and is coupled to a nanostructure comprising an agent, wherein the carrier cell comprises a cell surface coupling receptor, and wherein the nanostructure is coupled to the carrier cell with a ligand that binds to the cell surface coupling receptor. In some embodiments of the first aspect, the ligand is selected from the group consisting of antibodies, antibody fragments, soluble protein receptors, cytokines, peptides, small molecules, co-factors, hormones and neurotransmitters. In some embodiments, the cell surface receptor is CD45, such as a receptor that binds or is bound by an anti-CD45 monoclonal antibody (e.g., a human anti-CD45 antibody or a humanized anti-CD45 antibody). In some embodiments, the anti-CD45 monoclonal antibody is selected from the group consisting of BC8, 4B2, 9.4 and GAP8.3. In any of the foregoing embodiments of the first aspect, the carrier cell is a T cell, a B cell or a Natural Killer (NK) cell. In some embodiments, the carrier cell is a T cell, such as a $CD8^+$ T cell or a $CD4^+$ T cell. In some embodiments, the T cell is an adoptively transferred T cell. In some embodiments, the T cell is a chimeric antigen receptor (CAR) T cell.

In any of the foregoing embodiments of the first aspect, the nanostructure is selected from the group consisting of: liposomes, protein nanogels, nucleic acid nanogels and solidified polymers. In some embodiments, the nanostructure is a liposome. In some embodiments, the liposome is an interbilayer-crosslinked multilamellar vesicle (ICMV). In some embodiments, the nanostructure is a protein nanogel. In any of the foregoing embodiments of the first aspect, the nanostructure has a diameter of 1 to 1000 nanometers (nm). In some embodiments, the nanostructure has a diameter of 50 to 500 nm. In any of the foregoing embodiments of the first aspect, the ligand is covalently conjugated to the nanostructure. In some embodiments, the ligand is covalently conjugated to the nanostructure via a maleimide-thiol interaction.

In any of the foregoing embodiments of the first aspect, the agent is selected from the group consisting of a therapeutic agent, a prophylactic agent, a diagnostic agent and an imaging agent. In some embodiments, the agent is selected from the group consisting of proteins, nucleic acids and small molecule drugs. In some embodiments, the agent is a protein. In some embodiments, the protein is a cytokine. In some embodiments, the cytokine is IL-2, IL-15 or IL-15-Sa. In any of the foregoing embodiments of the first aspect, the nanostructure comprises on its surface a polycation. In some embodiments, the polycation is polylysine. In some embodiments, the polycation is polyethylene glycol-b-polylysine (PEG-PLL).

In a second aspect, the present disclosure provides a composition comprising a nucleated carrier cell that homes to a tumor coupled to a nanostructure comprising an agent, wherein the nanostructure comprises a surface associated with a polycation. In some embodiments, the carrier cell is a T cell, a B cell or a Natural Killer (NK) cell. In some embodiments, the carrier cell is a T cell. In some embodiments, the T cell is a $CD8^+$ T cell or a $CD4^+$ T cell. In some embodiments, the T cell is an adoptively transferred T cell. In some embodiments, the T cell is a chimeric antigen receptor (CAR) T cell. In any of the foregoing embodiments of the second aspect, the nanostructure is selected from the group consisting of: liposomes, protein nanogels, nucleic acid nanogels and solidified polymers. In some embodiments, the nanostructure is a liposome. In some embodiments, the liposome is an interbilayer-crosslinked multilamellar vesicle (ICMV). In some embodiments, the nanostructure is a protein nanogel. In some embodiments, the nanostructure has a diameter of 1 to 1000 nanometers (nm). In some embodiments, the nanostructure has a diameter of 50 to 500 nm. In any of the foregoing embodiments of the second aspect, the carrier cell is covalently conjugated to the nanostructure via a maleimide-thiol interaction.

In any of the foregoing embodiments of the second aspect, the agent is selected from the group consisting of a therapeutic agent, a prophylactic agent, a diagnostic agent and an imaging agent. In some embodiments, the agent is selected from the group consisting of proteins, nucleic acids and small molecule drugs. In some embodiments, the agent is a protein. In some embodiments, the protein is a cytokine. In some embodiments, the cytokine is IL-2, IL-15 or IL-15-Sa. In any of the foregoing embodiments of the second aspect, the polycation is polylysine. In some embodiments, the polycation is polyethylene glycol-b-polylysine (PEG-PLL).

In a third aspect, the present disclosure provides a composition comprising a T cell having a CD45 receptor coupled to a protein nanogel that comprises a polycation, wherein the T cell is coupled to the protein nanogel with a ligand that binds the CD45 receptor. In some embodiments, the ligand is selected from the group consisting of antibodies, soluble protein receptors, cytokines, peptides, small molecules, cofactors, hormones and neurotransmitters. In some embodiments, the ligand is an anti-CD45 monoclonal antibody, such as a human anti-CD45 antibody or a humanized anti-CD45 antibody. In some embodiments, the anti-CD45 monoclonal antibody is selected from the group consisting of BC8, 4B2, 9.4 and GAP8.3. In any of the foregoing embodiments of the third aspect, the T cell is a $CD8^+$ T cell or a $CD4^+$ T cell. In some embodiments, the T cell is an adoptively transferred T cell. In some embodiments, the T cell is a chimeric antigen receptor (CAR) T cell. In any of the foregoing embodiments of the third aspect, the protein nanogel has a diameter of 1 to 1000 nanometers (nm). In some embodiments, the protein nanogel has a diameter of 50 to 500 nm. In any of the foregoing embodiments of the third aspect, the ligand is covalently conjugated to the protein nanogel. In some embodiments, the anti-CD45 antibody is covalently conjugated to the protein nanogel via a linker that contains two N-hydroxysulfosuccinimide groups.

In any of the foregoing embodiments of the third aspect, the protein nanogel comprises a protein selected from the group consisting of therapeutic proteins, prophylactic proteins, diagnostic proteins and imaging proteins. In some embodiments, the protein nanogel comprises a cytokine. In some embodiments, the cytokine is IL-2, IL-15 or IL-15-Sa. In any of the foregoing embodiments of the third aspect, the polycation is polylysine. In some embodiments, the polycation is polyethylene glycol-b-polylysine (PEG-PLL).

The invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teachings that are referenced herein.

SEQUENCE TABLE A

| SEQ ID NO: | Name* | Sequence |
|---|---|---|
| 1 | Human IL-15 (N72D mutant) | NWVNVISDLKKIEDLIQSMHIDATLYTESDVHPSCKVTAMK CFLLELQVISLESGDASIHDTVENLIILAN<u>D</u>SLSSNGNVTESG CKECEELEEKNIKEFLQSFVHIVQMFINTS |
| 2 | Human IL-15RαSu/Fc (IgG1 CH2-CH3 (Fc domain)) | ITCPPPMSVE HADIWVKSYS LYSRERYICN SGFKRKAGTS SLTECVLNKA TNVAHWTTPS LKCIREPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 3 | Human IL-15RαSu (65aa-truncated extracellular domain) | ITCPPPMSVE HADIWVKSYS LYSRERYICN SGFKRKAGTS SLTECVLNKA TNVAHWTTPSLKCIR |
| 4 | Human IL-15 isoform 2 | MVLGTIDLCSCFSAGLPKTEANWVNVISDLKKIEDLIQSMH IDATLYTESDVHPSCKVTAMKCFLLELQVISLESGDASIHD TVENLIILANNSLSSNGNVTESGCKECEELEEKNIKEFLQSF VHIVQMFINTS |
| 5 | Human IL-15 isoform 1 | MRISKPHLRSISIQCYLCLLLNSHFLTEAGIHVFILGCFSAGL PKTEANWVNVISDLKKIEDLIQSMHIDATLYTESDVHPSCK VTAMKCFLLELQVISLESGDASIHDTVENLIILANNSLSSNG NVTESGCKECEELEEKNIKEFLQSFVHIVQMFINTS |
| 6 | Human IL-15 (without signal peptide) | NWVNVISDLKKIEDLIQSMHIDATLYTESDVHPSCKVTAM KCFLLELQVISLESGDASIHDTVENLIILANNSLSSNGNVTES GCKECEELEEKNIKEFLQSFVHIVQMFINTS |
| 7 | Human IL-15Rα (85aa-truncated extracellular domain) | ITCPPPMSVEHADIWVKSYSLYSRERYICNSGFKRKAGTS SLTECVLNKATNVAHWTTPSLKCIRDPALVHQRPAPPSTVT TAGV |

SEQUENCE TABLE A-continued

| SEQ ID NO: | Name* | Sequence |
|---|---|---|
| 8 | Human IL-15Rα (182aa-truncated extracellular domain) | ITCPPPMSVEHADIWVKSYSLYSRERYICNSGFKRKAGTS SLTECVLNKATNVAHWTTPSLKCIRDPALVHQRPAPPSTVT TAGVTPQPESLSPSGKEPAASSPSSNNTAATTAAIVPGSQL MPSKSPSTGTTEISSHESSHGTPSQTTAKNWELTASASHQPP GVYPQGHSDTTVAISTST |
| 9 | Human IL-15Rα Full length (Swiss prot: Q13261.1) | MAPRRARGCRTLGLPALLLLLLRPPATRGITCPPPMSVEH ADIWVKSYSLYSRERYICNSGFKRKAGTSSLTECVLNKAT NVAHWTTPSLKCIRDPALVHQRPAPPSTVTTAGVTPQPESL SPSGKEPAASSPSSNNTAATTAAIVPGSQLMPSKSPSTGTTE ISSHESSHGTPSQTTAKNWELTASASHQPPGVYPQGHSDTT VAISTSTVLLCGLSAVSLLACYLKSRQTPPLASVEMEAMEA LPVTWGTSSRDEDLENCSHHL |

*Su, refers to sushi domain.

EXAMPLES

While many nanostructures close to the cell surface are internalized rapidly via endocytosis or passive membrane permeation, some can retain on cell surface for a longer period of time. The reasons for the differences in internalization kinetics still remain elusive. Thus, studying the slowly-internalizing cell surface proteins bound by nanostructures provides insight into designing nanostructures with long surface retention. Currently, most effort is devoted to design internalizing drug conjugates to deliver intracellular drugs. However, if cell surface receptors with minimal internalization can be employed to design new structures with prolonged stability and residence time on cell surface, expanded drug libraries (e.g.: extracellular drugs such as cytokines and small molecule drugs) can be delivered to cells. The prolonged stability and maintenance of nanostructures on the cell surface also improves the efficacy and efficiency of nanostructures for use in drug delivery, imaging, tracking and diagnostic purposes.

Example 1. Identification of CD45 as Stable Cell Surface Anchor for Maximizing Liposome Loading An interlayer-crosslinked multilamellar vesicle (ICMV) (Nature Mater. 2011, 10, 243-251) is one type of particle that can remain on the cell surface (e.g., T cell surface) for more than four days. A candidate pool of slowly-internalizing receptors was obtained by mass spectrometry analysis of the total surface proteins ICMVs bound most abundantly. The screening for the main contributors for ICMVs' long surface retention was conducted by using liposomes which are surface coupled with an antibody against top candidate surface receptors such as CD2, CD11 and CD45. Antibody-conjugated liposomes coupled to carrier cells.

Liposome Synthesis

Antibody-conjugated liposomes were produced by hydrating dried high-$T_M$ phospholipid films containing 2.5% PEG-maleimide and 1% biotin head groups. Specifically, vacuum dried lipid films composed of 1,2-distearoyl-sn-glycero-3-phospho ethanolamine-N-[maleimide(polyethylene glycol)-2000 (maleimide-PEG$_{2000}$-DSPE)/cholesterol/hydrogenated Soy L-α-phosphatidylcholine (HSPC)/1,2-distearoyl-sn-glycero-3-phosphoethanolamine-N-[biotinyl (polyethylene glycol)-2000 (biotin-PEG$_{2000}$-DSPE) (Avanti Polar Lipids, Alabaster, Ala., USA) in a molar ratio of 2.5/27/68/1.5 together with 1% of a fluorescent lipophilic tracer dye DiD were rehydrated in 250 μL of 50-mM 4-(2-hydroxyethyl)-1-piperazineethanesulfonic acid (HEPES)/150-mM NaCl-buffer (pH=6.5). Lipids were vortexed every 10 min for 1 h at 62° C. to form vesicles and size extruded through a polycarbonate membrane (0.2 μm). After washing in excess PBS and spinning down by ultracentrifugation at 110,000×g for 4 h, liposomes were re-suspended in 100 μl PBS per 1.4 mg of lipids. For coupling to maleimide groups of the liposomes, antibody, cytokine and antibody/cytokine mixtures at different molar ratios (2-5 mg/mL) were treated with 1.8 mM dithiothreitol (DTT) in the presence of 10 mM EDTA at 25° C. for 20 min to expose hinge region free thiols. DTT was subsequently removed by using Zeba desalting columns before mixing with maleimide-bearing liposomes (1/1 wt./wt. for protein/lipid) in PBS. After incubation for 18 h at 25° C. on a rotator, excess protein was removed by ultracentrifugation in excess PBS. Unbound liposomes were washed off before T cells were incubated in Roswell Park Memorial Institute (RPMI) media at 37° C.

Antibodies (Ab) against surface receptors CD2, CD11, CD45 or a 1:1 ratio mixture of antibodies against two surface markers (e.g.: CD2/CD45 or CD11/CD45) were reduced by DTT to expose hinge region free thiol and then coupled to the liposome surface via a maleimide-thiol reaction, as described above. Antibodies were obtained from BioXcell (West Lebanon, N.H., USA), including anti-mouse CD45 antibody, clone number: MB23G2.

Liposome Coupling to Carrier Cells

Antibody-conjugated liposomes (0.7 mg lipids) in 100 μL PBS were incubated with 20×10$^6$ primed pmel-1 Thy1.1$^+$ CD8$^+$ T-cells in 0.5 ml complete RPMI supplemented with 10% fetal calf serum (FCS) for 30 min at 37° C. with gentle agitation every 15 min. Conjugated T-cells were washed with PBS (20 mL×2) to remove unbound liposomes and incubated in RPMI media with recombinant IL-7 (1.5 ng/mL) and 10% FCS at 0.5×10$^6$ cells/mL at 37° C.

Liposome Characterization

Figure 1B:
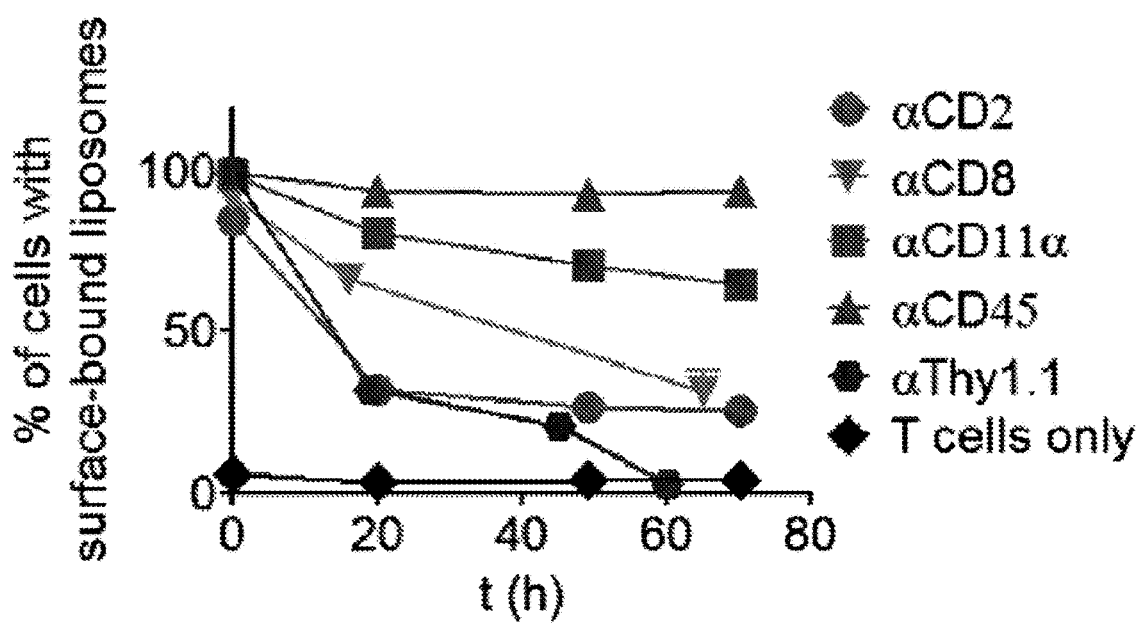
Figure 1C:
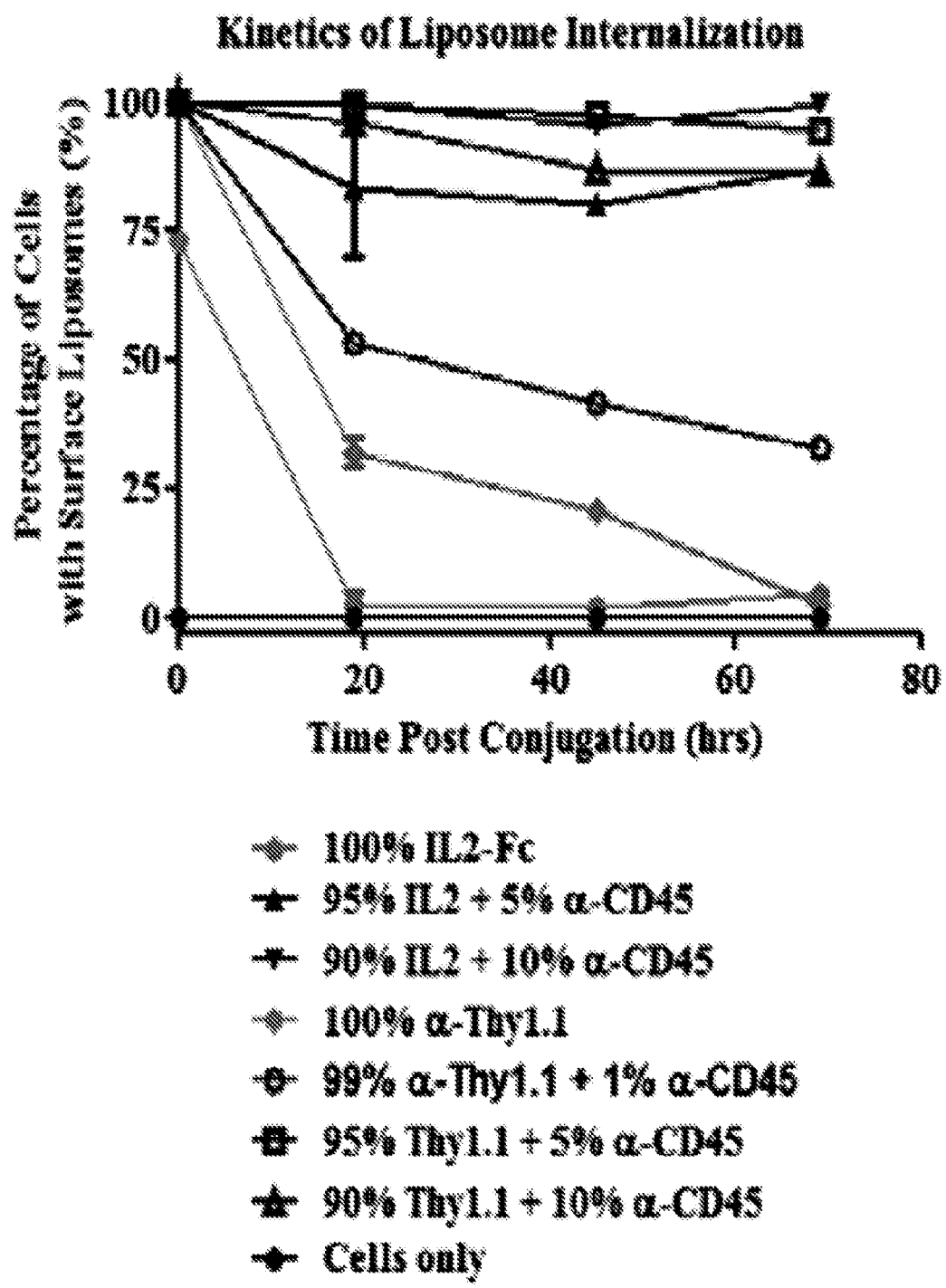

Unbound liposomes were washed off and cells were incubated at 37° C. in complete RPMI. Cells were stained by streptavidin-fluorophore and analyzed by flow cytometer at zero (0) hours (hr), 6 hr, 24 hr and 48 hr post conjugation (FIG. 1A) or zero (0) hr, 19 hr, 45 hr and 69 hrs after conjugation (FIG. 1B and FIG. 1C). The percentage of fluorescently labeled cells was plotted over time. Only T cells with surface liposomes would be fluorescently labeled as internalized liposomes did not have access to the streptavidin-dye. After 48 hrs, almost 100% of cells still had anti-CD45 (α-CD45) antibody decorated liposomes anchoring on their surface while surface anti-CD11 (α-CD11) antibody and anti-CD2 (α-CD2) antibody liposomes were only found on 30% and 70% of cells respectively (FIG. 1A). Unexpectedly, CD45 exhibited prolonged cell surface residence time over the faster internalization receptors CD11 and CD2. When α-CD45 was used in combination with α-CD2 or α-CD11 to surface decorate liposomes, liposomes anchored on both CD45 and CD2 (or CD45 and CD11) still remained on 100% of cells after two days regardless of the binding to the faster internalization receptor CD2 and CD11 (FIG. 1A). Anti-CD45 liposomes exhibited prolonged cell surface retention not only compared to CD2 and CD11, but also CD8 and Thy1.1 (FIG. 1B).

To further confirm the non-internalizing property of CD45 on liposomes, CD45 was tested together with a well-known internalizing IL-2 receptor and a congeneric marker Thy1. Antibodies against Thy1 (α-Thy1.1) or engineered IL-2-Fc protein composed of IL-2 fused to a mouse Fc antibody framework (prepared as previously described, (*J Controlled Release* 2013, 172, 426-435) were coupled to the liposome surface as described above. A ligand mixture containing fixed amounts of different mole ratios of α-Thy1.1 and α-CD45 (or IL-2-Fc and α-CD45) was also used to decorate the liposome surface. After conjugation to activated CD8+ T cells, 95% of IL-2-Fc liposomes and 70% of α-Thy1.1 liposomes were internalized within 20 hours respectively (FIG. 1C). Only 1 mol % of α-CD45 in the ligand cocktail assured 67% of cells had α-Thy1.1/α-CD45 liposomes on the surface even after 70 hours and 5% of α-CD45 assured almost 100% of cells with surface liposomes after 3 days. Similarly, 5% of α-CD45 reversed the fast internalization of IL-2 receptor and almost 90% of cells with surface retained IL-2-Fc/α-CD45 liposomes after 3 days. 100% of cells had IL-2-Fc/α-CD45 liposomes on surface when 10% α-CD45 was used (FIG. 1C). Surprisingly, binding of CD45 is safe to T cells despite the fact that CD45 is one of the most abundant glycoproteins on the lymphoid cells. When T cells were incubated with IL-2-Fc liposomes, the presence of α-CD45 liposomes (0.2 µg/ml) did not change the IL-2 signaling or affect T cell survival and proliferation (data not shown).

Figure 2:
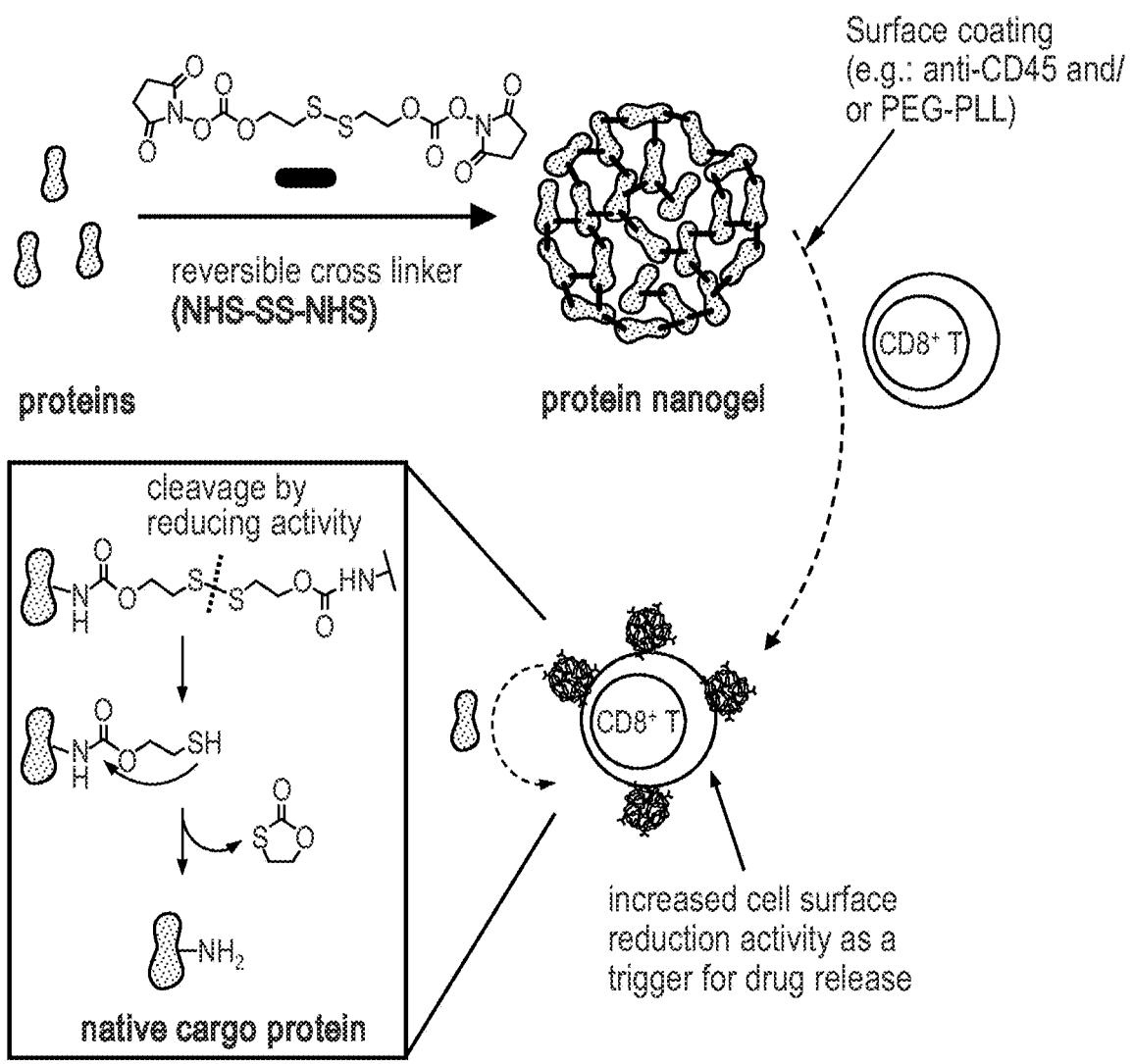
FIG. 2 shows a schematic of an example of preparation and surface modification of cytokine nanogels for cell surface coupling.

Example 2. Preparation and Surface Modification of Cytokine Nanogels for Efficient and Stable T Cell Surface Coupling Cytokine nanogels (NGs) were prepared as described in International Publication Number WO 2015/048498 A2, published on 2 Apr. 2015, incorporated by reference herein. Further modifications we made to the cytokine nanogels as described herein. Generally, the cytokines were chemically crosslinked with a reversible linker (NHS-SS-NHS) to form crosslinked nano-structure of proteins, named protein nanogel (NG, FIG. 2). After completion the crosslinking reaction of cytokines, anti-CD45 antibody and/or polycations are added in situ for modifying the NG surface (FIG. 2). Following synthesis, the nanogels were characterized and coupled to carrier cells as described further below.

Synthesis of Nanogels

Synthesis of NHS-SS-NHS crosslinker: In a 125 mL round-bottom flask, 2-hydroxyethyl disulfide (1.54 g, 10 mmol) was dissolved in tetrahydrofuran (THF, 30 mL, anhydrous) and added dropwise to the solution of phosgene (15 mL, 15 wt. % in toluene, 22 mmol). The mixture was stirred at 25° C. for 10 h followed by the removal of the solvent under vacuum. N-hydroxysuccinimide (NHS) (2.3 g, 22 mmol) was dissolved in THF (30 mL, anhydrous) and added as one portion, and then dry triethylamine (1.57 mL, 11 mmol) was injected. The reaction was carried at 40° C. for 16 h. The solvent was removed under vacuum and the mixture was filtered to remove precipitates. The crude product was purified by silica gel column chromatography (dichloromethane/methanol=10/1) and recrystallized with icy hexane (80 mL). The resulting white solid was dried under vacuum (3.1 g, yield 71%). $^1$H-NMR (CDCl$_3$, 500 MHz): δ 4.58 (t, 4H), 3.05 (t, 4H), 2.84 (s, 8H). $^{13}$C-NMR (CDCl$_3$, 500 MHz): δ 168.77, 151.66, 68.84, 36.68, 25.69. ESI (m/z): calcd for $C_{14}H_{16}N_2O_{10}S_2$, 436.4 [M]; found, 459.0 [M+Na]$^+$.

Nanogel Assembly

Human IL-15Sa nanogels: NHS-SS-NHS (93.5 µg, 0.214 µmol) was dissolved in 9.35 µL DMSO was added to IL-15Sa(ALT-803 (1320 µg, 0.0143 mol), Altor BioScience Corporation (Miramar, Fla., USA.) See also US2014/0134128 and *Cytokine* 2011, 56, 804-810) solution in 132 µL phosphate buffered saline (PBS) pH 7.4. The mixture was rotated at 25° C. for 30 min followed by the addition of 1188 µL PBS buffer. For nanogels (NGs) incorporating the CD45 targeting antibody, anti-CD45 (215 µg, 0.0014 µmol) in 31.7 µL PBS buffer was then added to the diluted solution. Either anti-mouse CD45RB (clone: MB23G2: purchased from BioXCell (West Lebanon, N.H., USA)) or anti-human CD45 (clone: MEM-28: purchased from Abcam (Cambridge, United Kingdom)) was used. The reaction mixture was rotated at 25° C. for another 30 min. The preparation of IL-15Sa-NG without anti-CD45 was similar except that anti-CD45 was replaced by the permanent linker, NH$_2$-PEG$_{10k}$-NH$_2$ (715 µg, 0.0715 µmol) (Laysan Bio: Arab, Ala., USA) in 35.8 µL PBS buffer. Non-degradable NGs (e.g., aCD45/IL-15Sa-NG (non-deg.)) were prepared using a permanent linker, bis(sulfosuccinimidyl) substrate (Thermo Fisher Scientific, Waltham, Mass., USA) in lieu of NHS-SS-NHS.

Other protein nanogels: IL-2-Fc protein NGs were prepared with similar protein concentrations and the same crosslinker/protein mole ratio. IL-2-Fc is a bivalent fission protein of the C-terminus of murine wild type IL-2 linked to a mouse IgG2a backbone. IL-2Fc was prepared as previously described (*J Controlled Release* 2013, 172, 426-435). Bovine Serum Albumin (BSA) (Sigma-Aldrich, St Louis, Mo., USA) and Human IgG (Jackson Immuno Research Labs, West Grove, Pa., USA) nanogel controls were also prepared with similar protein concentrations and the same crosslinker/protein mole ratios as described above. The resultant NGs were then washed with PBS (1.5 mL×3) in an Amicon centrifugal filter (molecular weight cut-off=100 kDa, Millipore, Billerica, Mass., USA). For example, in the preparation of mouse IL-2Fc nanogels, reversible disulfide crosslinker (107.9 µg, 0.247 µmol) dissolved in 10.8 µL DMSO was added to IL-2-Fc (1650 µg, 0.0165 µmol) solution in 165 µL PBS buffer. The mixture was rotated at room temperature (rt) for 30 min followed by the addition of 1485 µL PBS buffer. Anti-CD45 (247.5 µg, 0.0016 µmol) in 43 µL PBS buffer was then added to the diluted solution. The reaction mixture was rotated at room temperature for another 30 min. The resultant IL-2-Fc NGs was collected with Millipore Amicon ultra-centrifugal filter (molecular weight cutoff=100,000 Da) and washed with PBS (1.5 mL×3). The final concentration of IL-2-Fc NG was determined with Nanodrop (A280). The purified IL-2-Fc NG was stored in PBS at 4° C. before use. The preparation of IL-2Fc nanogels without anti-CD45 was similar except that anti- CD45 was replaced by the permanent linker, $NH_2$-$PEG_{10K}$-$NH_2$ (715 µg, 0.0715 µmol) (Laysan Bio: Arab, Ala., USA) in 35.8 µL PBS buffer.

Polylysine Modification of Nanogels

In order to enrich more NGs onto T cell surface, a polycation (e.g., polyethylene glycol-b-polylysine (PEG-PLL)) was added in situ to some samples prior to carrier cell coupling. For example, freshly prepared anti-CD45/IL-15Sa-NG solution was diluted to 1 µg/µL followed by the addition of polyethylene glycol-b-polylysine ($PEG_{5K}$-$PLKC_{200}$, 19 µg, 0.0005 µmol or 43.6 µg, 0.0011 µmol) (Alamanda Polymers, Huntsville, Ala., USA) in 43.6-µL PBS prior to T cell coupling described below. The mixture was then rotated at 25° C. for 30 min and used without further purification.

Fluorescence and Biotin Labelling of NGs.

To prepare fluorescently-labeled NGs, cytokine cargos were fluorescently labeled with Alexa Fluor 647 NHS ester (Thermo Fisher Scientific) and purified with Amicon ultra-centrifugal filters (molecular weight cut-off 50 kDa). Fluorescent cytokine was mixed with non-labelled cytokine (10 mol % labelled cytokine) for the preparation of fluorescent NGs following the same procedure as described above. For the preparation of biotinylated NGs, NHS-SS-NHS (93.5 µg, 0.214 µmol) dissolved in 9.35 µL DMSO was added to IL-15Sa (1320 µg, 0.0143 µmol) solution in 132 µL PBS buffer. The mixture was rotated at 25° C. for 20 min followed by the addition of EZ-Link NHS-LC-LC-Biotin (40.6 µg, 0.072 mol, Thermo Fisher Scientific) in 7.5 µL DMSO. The mixture was rotated at 25° C. for another 20 min and then diluted with 1188 µL PBS buffer followed by the addition of anti-CD45 (215 µg, 0.0014 µmol) in 31.7 µL PBS buffer. The rest procedure was the same as described above.

Coupling of NGs to Carrier Cells

In a typical experiment, aCD45/IL-15Sa-NG (950 µg, 0.010 µmol) labelled with Alexa Fluor 647 in 950 µL PBS was added to mouse $CD8^+$ T-cells ($95 \times 10^6$) in 475 µL HBSS followed by incubation at 37° C. for 1 h. The T-cells with surface coupled NGs were collected by centrifugation at 800×g for 5 min, washed with PBS (1.0 mL×2), and resuspended in buffer or media at desired concentrations for in vitro or in vivo studies. For measurements of total NG coupling, fluorescently-labelled NGs were coupled to T-cells, and supernatants were collected and measured for fluorescence intensity at excitation/emission wavelengths of 640/680 nm using a plate reader (Tecan Infinite® M1000 PRO). Fluorescence readings were converted to NG concentrations using standard curves prepared from serial dilutions of NG stock solutions. The amount of coupled NG was calculated by subtracting the unbound NG from the total added amount. NG loading per cell was controlled by varying the mass of NGs added to cells for coupling. For the conjugation of NGs lacking anti-CD45 to T-cells, IL-15Sa-NG (950 µg, 0.010 µmol) in PBS (950 µL) was first activated with sulfosuccinimidyl 4-(N-maleimidomethyl)cyclohexane-1-carboxylate (218 µg, 0.50 µmol) or bis(sulfosuccinimidyl) substrate (286 µg, 0.50 mol), collected with Amicon ultra-centrifugal filter (molecular weight cut-off 50 kDa) and washed with PBS (1.5 mL×3), and then added to $CD8^+$ T-cells ($95 \times 10^6$) in 475 µL HBSS followed by incubation at 37° C. for 1 hr. Cells were washed and collected similarly. The amount of conjugated NG was determined similarly as described above. Coupling of NGs with or without anti-human CD45 to human $CD8^+$ T-cells followed the similar procedures as described above. Similar assays were performed with anti-CD3/CD28-activated human $CD8^+$ T cells isolated from peripheral blood mononuclear cells.

The modified cytokine NGs showed higher efficiency for T cell coupling compared with non-modified NGs (Tables 1-3). The amount of PEG-PLL added in the coupling reaction was titrated, and it was found that the trend of increased coupling efficiency with increased amount of PEG-PLL added (Table 1). Unexpectedly, the coupling efficiency to T cells can be improved to 40.4% when only 0.05 equiv. PEG-PLL was added to the IL-2-Fc NGs with slightly increased particle size (180.0±2.8 nm) compared with coupling efficiency of 13.2% for unmodified NGs. Surface density of NGs of 4.04 µg/$1 \times 10^6$ cells were easily achieved, which permits high loading of cytokine drug to adoptively transferred T cells for prolonged expansion and anticancer activity. Due to the different coupling efficiency, T cells with different surface density of IL-2-Fc NGs were obtained, which was verified with flow cytometry (data not shown). A similar study was performed with human IL-15Sa NGs. Coupling efficiency of 77.0% was achieved when 0.05 equiv. PEG-PLL was added to human IL-15Sa NGs (Table 2). T cells with different surface density of human IL-15Sa NGs were also obtained and verified with flow cytometry (data not shown).

TABLE 1

Polycations improve the coupling efficiency of mouse IL-2-Fc nanogels on T cell surface. Nanogels contained fixed amounts of CD45 to IL-2Fc (1:10 moles) [a]Different amount of PEG-PLL was mixed with mouse IL-2-Fc nanogels right before the coupling reaction; [b]The size of the nanogel was measured with dynamic light scattering after adding PEG-PLL; [c]Coupling efficiency = conjugated nanogel/total nanogel added to T cells; [d] The amount of surface-bound nanogel was calculated based on the feeding amount of nanogel (5 µg/100,000 cells) and coupling efficiency.

| Entry | PEG-PLL (equiv. of IL2-Fc, mol/mol)[a] | Size (nm)[b] | Coupling efficieny[c] | Surface-bound nanogel (µg/1 × $10^6$ cells)[d] |
|---|---|---|---|---|
| 1 | 0 | 85.1 ± 2.6 | 13.2% | 0.66 |
| 2 | 0.01 | 101.2 ± 4.9 | 33.1% | 1.66 |
| 3 | 0.02 | 111.3 ± 1.2 | 33.3% | 1.66 |
| 4 | 0.05 | 180.0 ± 2.8 | 40.4% | 2.02 |
| 5 | 0.06 | 601.9 ± 16.5 | 80.2% | 4.04 |

TABLE 2

Polycations improve the coupling efficiency of human IL-15Sa nanogels on the T cell surface. Nanogels contained fixed amounts of CD45 to IL-15Sa (1:10 moles). [a] Different amount of PEG-PLL was mixed with human IL-15Sa nanogel right before the coupling reaction; [b]The size of the nanogel was measured with dynamic light scattering after adding PEG-PLL; [c]Coupling efficiency = conjugated nanogel/total nanogel added to T cells; [d]The amount of surface-bound nanogel was calculated based on the feeding amount of nanogel (5 µg/100,000 cells) and coupling efficiency.

| Entry | PEG-PLL (equiv. of IL-15Sa, mol/mol)[a] | Size (nm)[b] | Coupling efficieny[c] | Surface-bound nanogel (µg/1 × $10^6$ cells)[d] |
|---|---|---|---|---|
| 1 | 0 | 71.1 ± 5.3 | 25.6% | 1.28 |
| 2 | 0.02 | 297.8 ± 11.4 | 35.4% | 1.77 |
| 3 | 0.05 | 280.8 ± 13.1 | 77.0% | 3.85 |
| 4 | 0.08 | 301.5 ± 15.5 | 89.6% | 4.48 |

TABLE 3

Hydrodynamic size and ξ-potential of IL-15Sa-NGs, before and after surface modification with anti-CD45 and PEG-PLL.

| surface modification | Size (nm) | zeta potential (mV) |
|---|---|---|
| before | 89.6 ± 9.3 | −10.3 |
| after | 121.0 ± 13.1 | 7.03 |

To evaluate the TCR signaling responsiveness of protein nanogels resting on primed mouse T cells we isolated using the following protocol. Spleens from C57Bl/6 or pmel-1 Thy1.1⁺ mice (Jackson Laboratory) were ground through a 70-µm cell strainer and red blood cells were removed by incubating with ACK lysis buffer (2 mL per spleen) for 5 min at 25° C. Resting CD4⁺ or CD8⁺ T-cells were isolated from splenocytes directly via magnetic negative selection using an EasySep™ Mouse CD4⁺ or CD8⁺ T-cell Enrichment Kit (Stemcell Technologies, Vancouver, Canada) respectively. For activated CD8⁺ T-cells, the splenocytes were washed with PBS and then cultured in RPMI 1640 medium containing 10% FCS, con-A (2 µg/mL) and IL-7 (1 ng/mL) at 37° C. for activation. After 2-day incubation, dead cells were removed by Ficoll-Pague Plus gradient separation and CD8⁺ T-cells were isolated using an EasySep™ Mouse CD8⁺ T-cell Enrichment Kit. Purified CD8⁺ T-cells were re-suspended at 1.5×$10^6$ per mL in RPMI containing 10 ng/mL recombinant murine IL-2. After 24 h, cells were washed 3 times in PBS and re-suspended in buffer or media for in vitro and in vivo studies.

Human CD8⁺ T-cells were also isolated for parallel experiments. Total peripheral blood mononuclear cells (PBMCs) were obtained from healthy donors (New York Blood Center, Long Island City, N.Y., USA). Resting CD8⁺ T-cells were isolated directly using an RosetteSep™ Human CD8⁺ T-Cell Enrichment Cocktail (Stemcell). The human CD8⁺ T-cells were activated in non-tissue culture plated coated with anti-human CD3 (2.5 µg/mL) and anti-human CD28 (1.0 µg/mL) in the presence of human IL-2 (50 UI/mL) for 2 days. Cells were washed 3 times in PBS and re-suspended in buffer or media for in vitro studies.

T-cell surface reduction activity was determined using a commercial WST-1 assay kit containing WST-1 and an electron coupling reagent (Roche, Basel, Switzerland). Resting or concanavalin A (con-A)-primed CD8⁺ T-cells from C57Bl/6 mice were suspended in Hank's Balanced Salt Solution (HBSS) at 1×$10^6$/mL. The commercial WST-1 reagent mixture (10 µL) was added to the T-cell suspension (200 µL). The cells were incubated at 37° C. for 1 h. WST-1 formazan production rate was measured with a plate reader (Tecan Infinite® M1000 PRO, Tecan, Männedorf, Switzerland) for increased absorbance at 450 nm during the incubation. For the measure of cell surface reduction in response to TCR triggering, resting or con-A-activated CD8⁺ T-cells were incubated with anti-CD3/CD28-coated beads (1:1 cell: bead ratio) or gp100 peptide (10 µg/mL) in the presence of IL-7 (1 ng/mL) at 37° C. for 24 h. Cells were washed and resuspended in HBSS (1×$10^6$/mL) and measured for surface reduction with the same commercial WST-1 reagent mixture after 1-h incubation at 37° C.

Figure 3A:
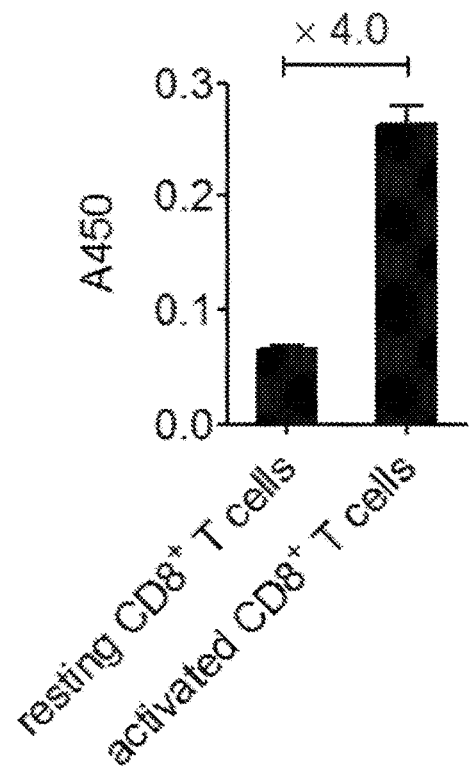
FIG. 3A shows cell surface reduction rates of resting and primed CD8$^+$ T cells.

Primed CD8⁺ T-cells showed markedly elevated cell surface reduction rates compared with resting T-cells as measure by the WST-1 assay (FIG. 3A). T-cell surface redox activity further increased following stimulation with antigen or anti-CD3/CD28-coated beads. We reasoned that increased redox activity at the T-cell surface could be exploited to obtain antigen-triggered adjuvant protein release using reduction-responsive nanoparticles bound to the plasma membrane of T-cells. Thus, the disulphide cross-linker was designed to cleave in response to reducing conditions at the T-cell surface, followed by release of un-adducted protein cargo through a self-immolative reaction. We focused on promising therapeutic cytokine cargos. Primed pmel-s CD8⁺ T-cells were conjugated with anti-CD45/cytokine- or cytokine only-biotinylated NGs, incubated for indicated periods of time, then stained with streptavidin for analysis of cell-surface NGs by flow cytometry. With anti-CD45 on the nanogel surface, both the IL-2-Fc NG and IL-15Sa NG showed increase coupling on the T cell surface. Cytokine release from the nanogel also occurred at the expect molecular weight indicating the intact cytokine without residual chemical groups.

Figure 3B:
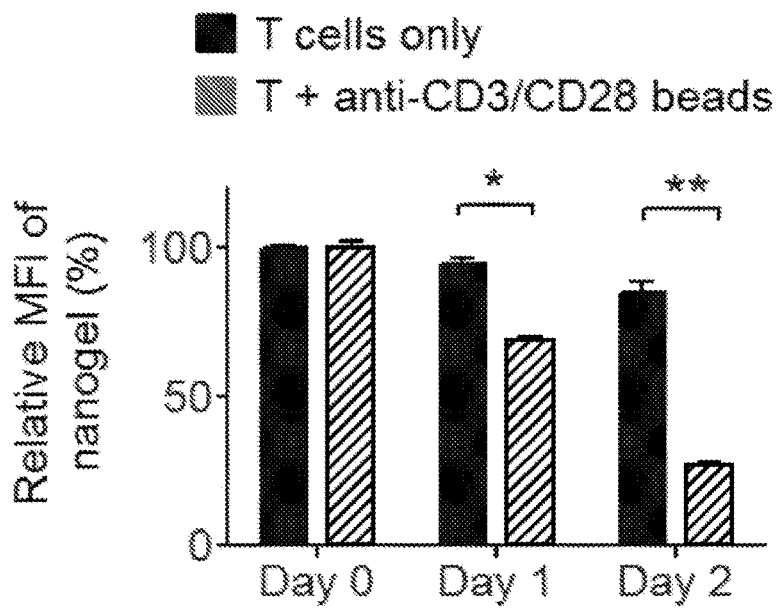
FIG. 3B shows anti-CD45 mediated anchoring of nanogels to the T cell surface enables TCR-responsive protein cargo release.

In addition, anti-CD45 NGs coupled to human primed T cells also releases protein much faster when the cells were stimulated with anti-CD3/CD28 beads (FIG. 3B). Results surprisingly show that surface modified anti-CD45 and polycations, the cytokine NGs can be efficiently coupled to and stably anchored on the T cell surface enabling TCR-responsive protein cargo release in vitro.

Example 3. Cytokine Nanogels Promote Effector T Cell Expansion In Vitro and In Vivo In vitro proliferation assays of T cells were conducted to determine the effect of anti-CD45 on T cell expansion. Naïve pmel-1 CD8+ T-cells were labelled with carboxyfluorescein succinimidyl ester (CFSE) and then conjugated with aCD45/IL-15Sa-NG, IL-15Sa-NG, or aCD45/IL-15Sa-NG (non-deg.) respectively as described above. After removing unbound NGs, T-cells were resuspended in RPMI with 10% FCS ($5.0\times10^5$/mL) and added to anti-CD3/CD28 coated beads at a 1:2 bead:T-cell ratio. Free IL-15Sa was added to the cells in control groups at equivalent dose (pulsed or continuous). Cell media were replaced every 3 days and free IL-15Sa was replenished in the continuous treatment group. At selected time points, replicates of T-cells were added with counting beads and washed with flow cytometry buffer (PBS with 2% FCS) followed by aqua live/dead staining. Cells were stained for surface markers (CD8, CD122) with antibodies followed by fixation and permeabilization with Intracellular Fixation & Permeabilization Buffer Set (eBioscience). Cells were then stained intracellularly for pSTAT5 and Ki67, and analysed with a flow cytometer (BD Canto, BD Biosciences).

Figure 4:
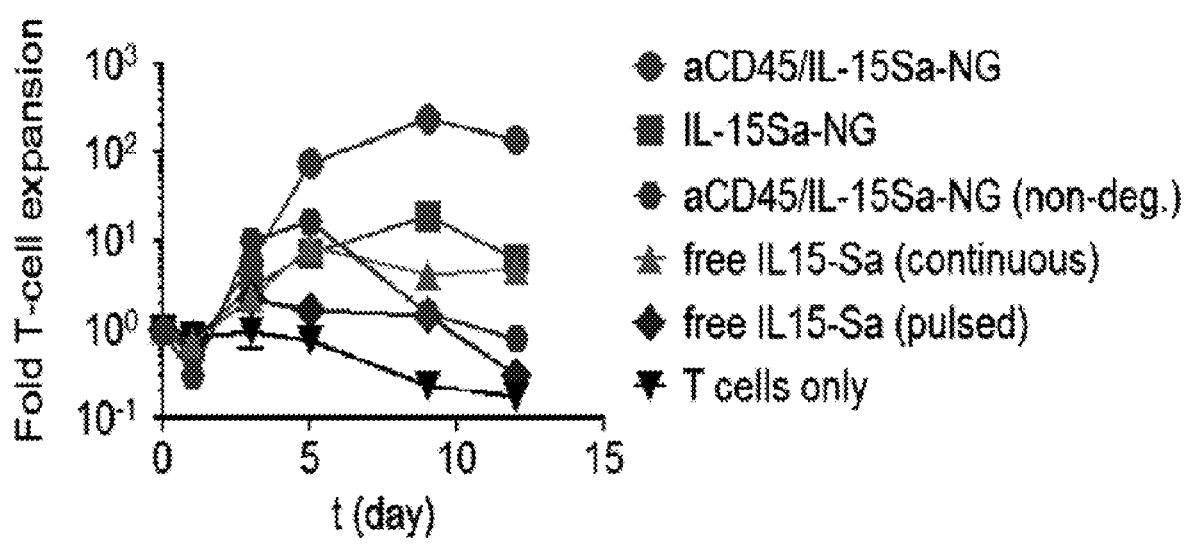
FIG. 4 shows IL-15Sa nanogels promote T cell expansion in vitro.

Anti-CD45/IL-15Sa-NG coupled to T-cells stimulated with anti-CD3/CD28 beads proliferated extensively, expanding ~100-fold in 5 days, much greater than T-cells pulsed with the same total quantity of free IL-15Sa for 1 hr. NG coupled T-cells also expanded more than cells cultured continuously with free IL-15Sa, suggesting cell surface localization of the NGs enhanced receptor engagement (FIG. 4). Nanogels linked to T-cells covalently rather than via anti-CD45 (IL-15Sa-NGs) and NGs formed with a non-degradable crosslinker (aCD45/IL-15Sa-NGs (non-deg.)) stimulated weaker T-cell expansion than redox-responsive, aCD45/IL-15Sa-NGs (FIG. 4); thus, prolonged cell surface retention and release of cytokine from NGs were both important for maximal stimulation. NGs enhanced T-cell proliferative responses to anti-CD3/CD28 beads at doses as low as ~30 ng IL-15Sa/$10^6$ cells. IL-15Sa-coupled T-cells maintained approximately constant levels of IL-15Rβ (CD122) and maintained stimulation of T-cells for at least a week in culture, as evidenced by elevated levels of pSTAT5 and Ki67 over 9 days. Addition of a CD45 inhibitor did not alter the proliferative response to the NGs, implying that NG anchoring did not trigger suppressive CD45 phosphatase activity. Thus, IL-15Sa NG backpacks provide sustained and potent stimulation of T-cells in the presence of TCR activation.

This might be due to the combined effect of (1) prolonged surface retention of IL-15Sa/α-CD45 NG thus more IL-15Sa released before internalization and (2) enhanced loading of the cytokine nanogel to the cell surface, thus enhanced IL-15Sa loading on the cell surface as additional anchor CD45 facilitates binding of IL-15Sa/α-CD45 NG.

To determine the In vivo effect of IL-Sa/anti-CD45 NGs on T cell expansion in tumor bearing mice using the syngeneic B16F10 melanoma mouse model (*Proc. Natl. Acad. Sci. U.S.A.*, 2004, 101, 1969-1974). B16F10 melanoma cells (American Tissue Culture Collection (Manassas, Va., USA) ($5.0\times10^5$) were injected subcutaneously (s.c.) in the flanks of C57Bl/6 mice on day 0. Animals were sublethally lymphodepleted by total body irradiation (5 Gy) 6 days post tumour inoculation. Primed pmel-1 CD8+ T-cells ($1.0\times10^7$) alone or with surface coupled NGs in 200 μl PBS were administered intravenously (i.v.) at day 7. Treatment groups, included T cell alone, T cells followed by a systemic injection of free IL-15Sa (40 ug), and T cells coupled with an anti-CD45IL-15Sa-NG (40 ug). Tumour area (product of 2 measured orthogonal diameters) and body weight were measured every two days. To monitor in vivo T-cell expansion and function, mice were sacrificed on day 14 for necropsy and flow cytometry analyses, unless body weight loss was beyond 20% of predosing weight, or tumour area reached 150 mm² (as predetermined endpoint), or the animal had become moribund at which point mice were euthanized.

Inguinal lymph nodes (distal or tumour draining lymph node) and spleens were ground through a 70-μm cell strainer. Splenocytes were then lysed with ACK lysis buffer (2 mL per spleen) for 5 min at 25° C. to remove red blood cells. Blood samples (200 μL) were lysed with ACK lysis buffer (1 mL×2) for 5 min at 25° C. Tumours were weighed and ground through a 70-μm cell strainer. All cells were added with counting beads and washed with flow cytometry buffer (PBS with 2% FCS) followed by aqua live/dead staining. Cells were stained for surface markers (CD8, Thy1.1, CD4, NK1.1) with antibodies followed by fixation and permeabilization with Cytofix/Cytoperm (BD Biosciences). Cell were then stained intracellularly for Ki67. After washing with FACS buffer, cells were re-suspended in FACS buffer and analysed by flow cytometry. For intracellular cytokine staining, samples in single-cell suspensions were incubated with gp100 peptide (10 μg/mL) at 37° C. for 2 h followed by the addition of brefeldin A (eBioscience, San Diego, Calif., USA) and incubation for another 4 h. Following surface staining as described above, samples were fixed and permeabilized in the same manner and stained with antibodies against IFN-γ, TNF-α and IL-2. Flow cytometric analysis was carried out using a BD Fortessa (BD Biosciences), and data analysis was performed using FlowJo software (Tree Star, Oreg., USA).

Figures 5A, 5B:
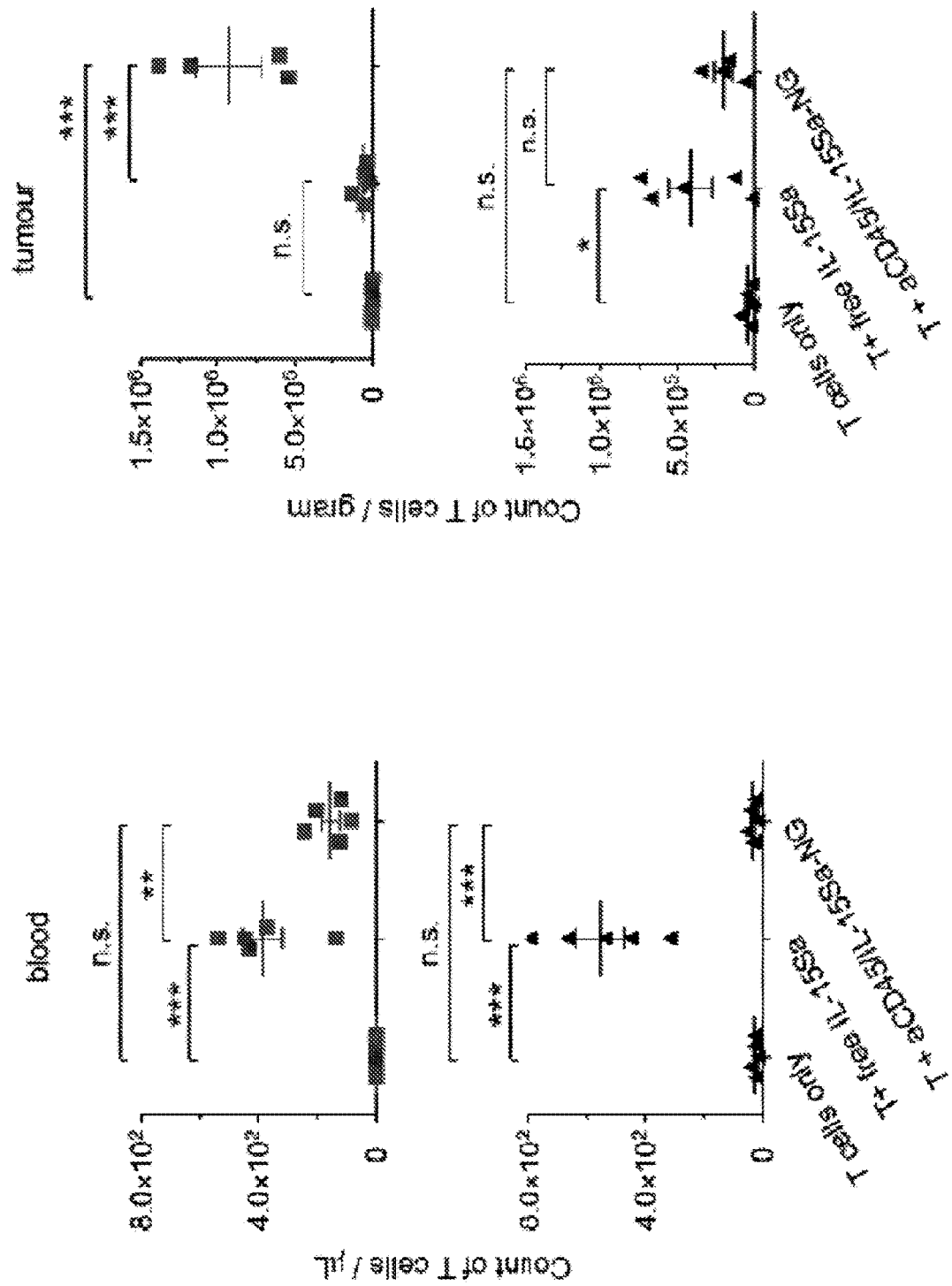
FIGS. 5A-5E shows IL-15Sa nanogels promote specific expansion of adoptively transferred T cells in tumors. Specifically, counts of adoptively transferred (ACT) Thy1.1$^+$ CD8$^+$ T-cells (squares) and endogenous Thy1.1$^-$CD8$^+$ T-cells (triangles) in blood (FIG. 5A, normalized by volume) and tumours (FIG. 5B, normalized by weight).
Figure 5C:
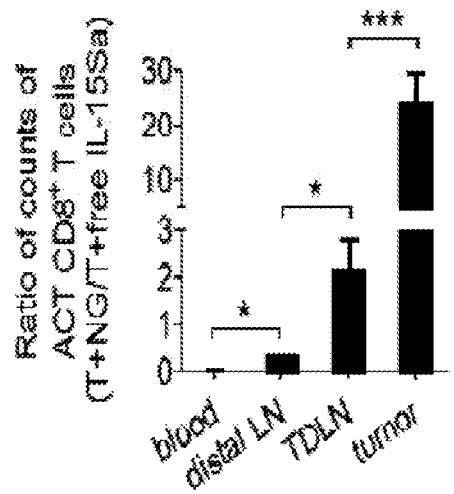
Figure 5D:
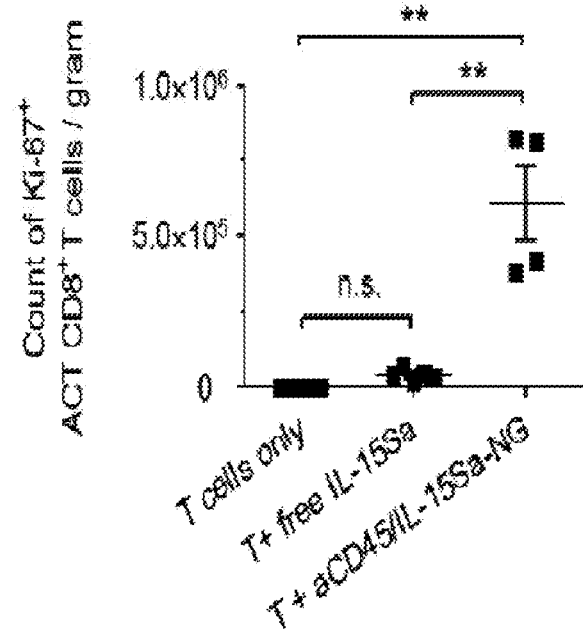
Figure 5E:
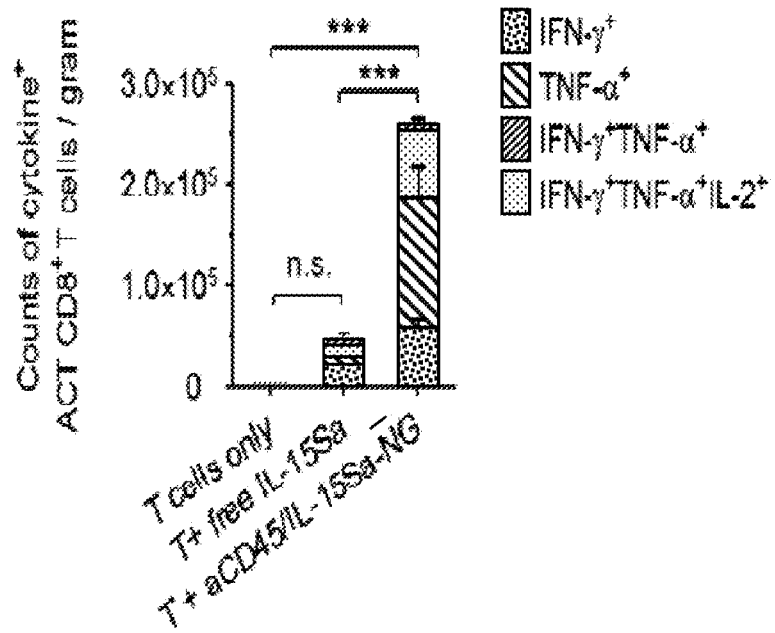

ACT adjuvanted by free systemic IL-15Sa led to substantial expansion of both transferred pmel-1 T-cells and endogenous T-cells in the blood (FIG. 5A), and also expanded NK cells and CD4+ T-cells in the systemic circulation. Systemic IL-15Sa also expanded endogenous T-cells in tumour-draining lymph nodes (TDLNs) (data not shown) and tumours (FIG. 5B). By contrast, IL-15Sa delivered as backpacks expanded the transferred CD8+ T-cells but did not expand endogenous T-cells in any compartment (FIG. 5A-5B). In tumours, where we expected antigen recognition to accelerate IL-15Sa release from the NGs, IL-15Sa-coupled T-cells expanded 16-fold more than pmel-1 cells in the soluble IL-15Sa-adjuvanted group and 1000-fold more than the T-cells without cytokine support (FIG. 5B). Ranking tissues in order of expected increasing antigen concentration (blood<distal LN<TDLN<tumour), we observed a corresponding increasing ratio of ACT T-cell counts in the NG group vs. ACT cells in the free IL-15Sa-adjuvanted group (FIG. 5C). Backpacked T-cells in the tumour were also proliferating and producing effector cytokines (FIG. 5D-5E). Even at high doses of Il-15Sa/anti-CD45 NGs still did not inflict toxicity (e.g.: 57 ug per mouse) while systemic IL15Sa caused a significant (18%) drop in body weight. Nanogel IL-15Sa delivery thus focused cytokine action on the transferred T-cells, and preferentially in antigen-bearing microenvironments in vivo with no toxic effects.

Example 4. Cytokine Delivery by Nanogel Backpacks Increases the Therapeutic Window for Adjuvant Cytokine Therapy The syngeneic B16F10 melanoma mouse model described above was used, however, the treatment groups were as follows. Animals received sham injections of PBS, T cells only, T cells followed by different doses of i.v. injected free IL-15Sa as a single dose (immediately after adoptive transfer) or split into multiple doses (days 7, 10, 13 and 16) or T cells coupled with anti-CD45/IL-15Sa NG at different doses. Body weights and systemic cytokine, chemokine and liver enzyme levels were analysed over time. Relative body weigh was normalized to day 7 body weight. Counts of cytokine+ endeogenous CD8+ T-cells and ACT CD8+ T-cells in blood were analyzed by intracellular cytokine staining and flow cytometry on day 14. Serum cytokine levels and liver enzymes were measured from samples collected on day 17 or when animals were euthanized due to toxicity. Cytokine levels were measured using Cytometric Bead Array (CBA) Mouse Inflammation Kit (BD Biosciences). Serum samples were also sent to IDEXX Reference Laboratories for analysis of alanine transaminase (ALT) and aspartate transaminase (AST). Data represent the mean±s.e.m. (n=5/group) and are compared with control group (T cells only) for statistical analyses. *, p<0.05; , p<0.01; *, p<0.001 by One-Way ANOVA and Tukey's tests; n.s., not significant; n.d., not detectable.

Figure 6A:
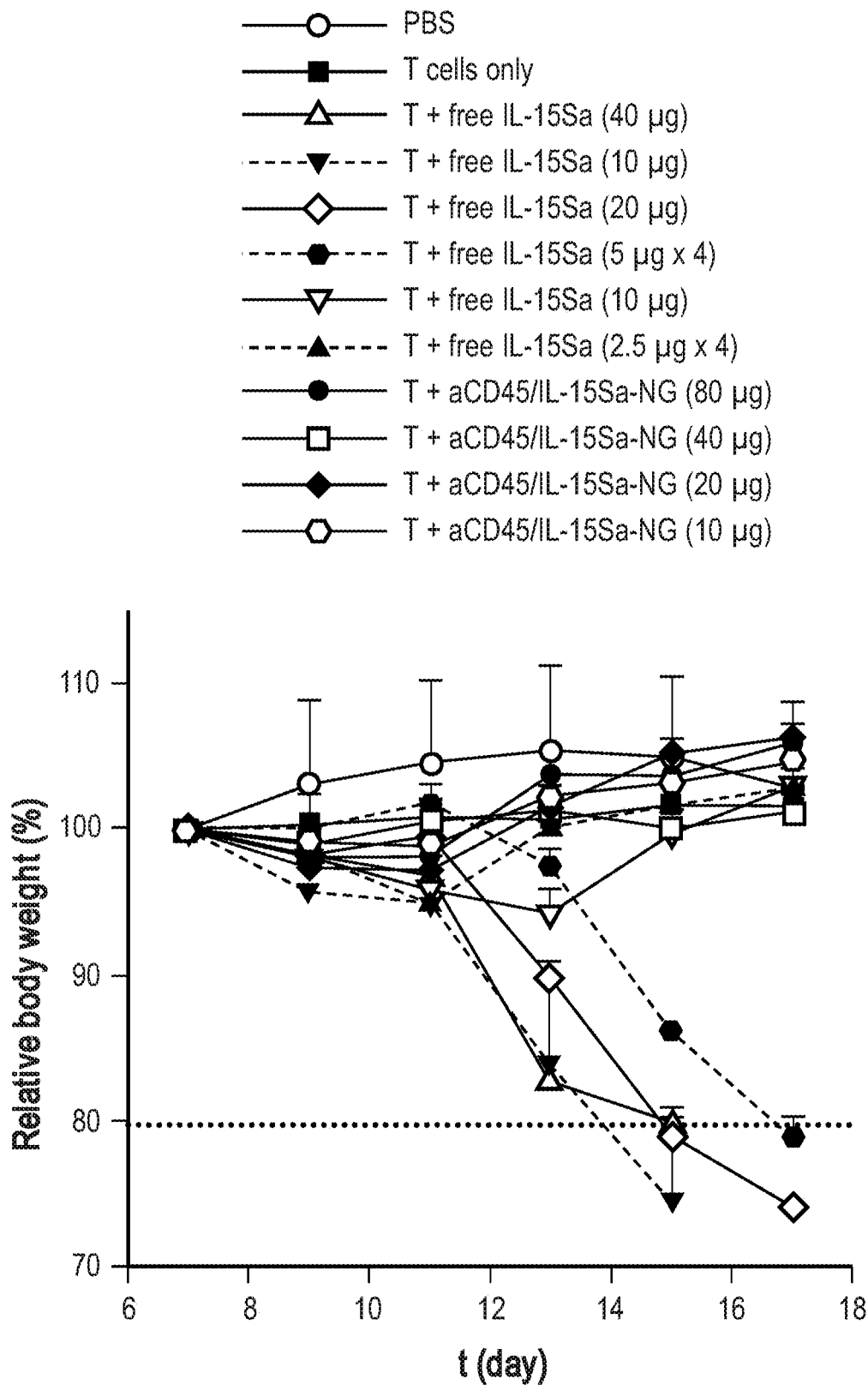
FIGS. 6A-6E show IL-15Sa nanogels increase the therapeutic window for adjuvant cytokine delivery during ACT, for example, with increase tolerability up to 80 µg as measured by body weight normalized to day 7 (FIG. 6A), counts of cytokine+ endogenous CD8+ T-cells (FIG. 6B) and ACT CD8+ T-cells (FIG. 6C) in blood and serum cytokine levels (TNF-α, FIG. 6D; IL-6, FIG. 6E).
Figure 6B:
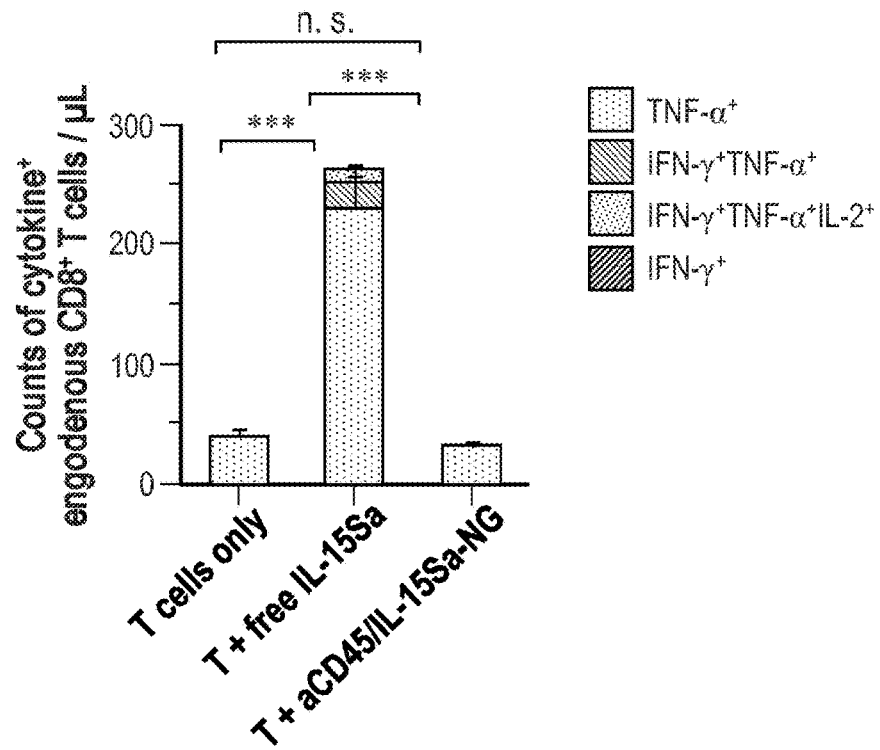
Figure 6C:
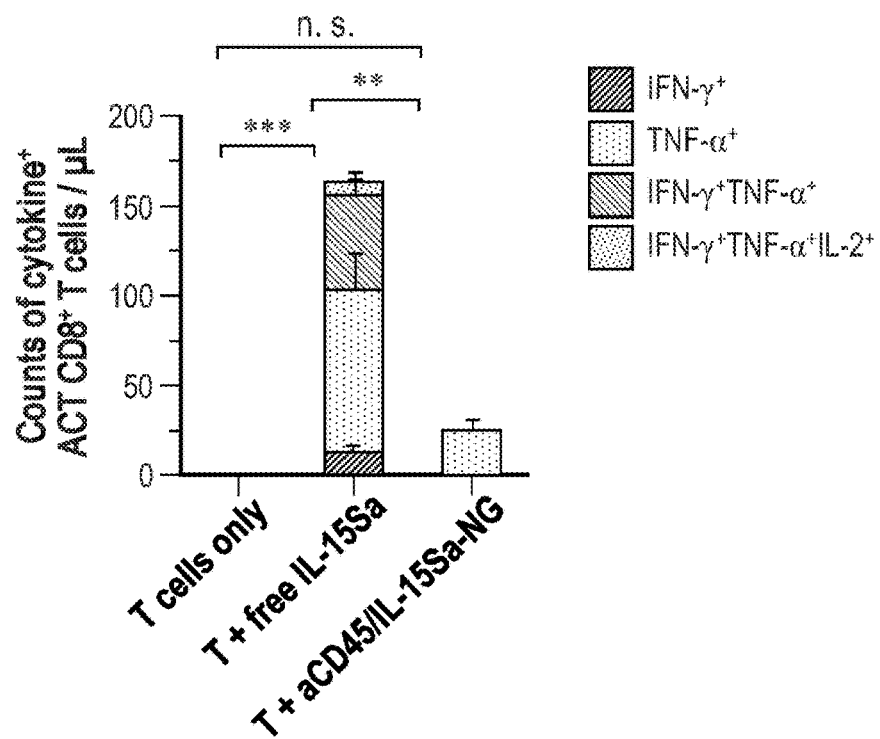
Figure 6D:
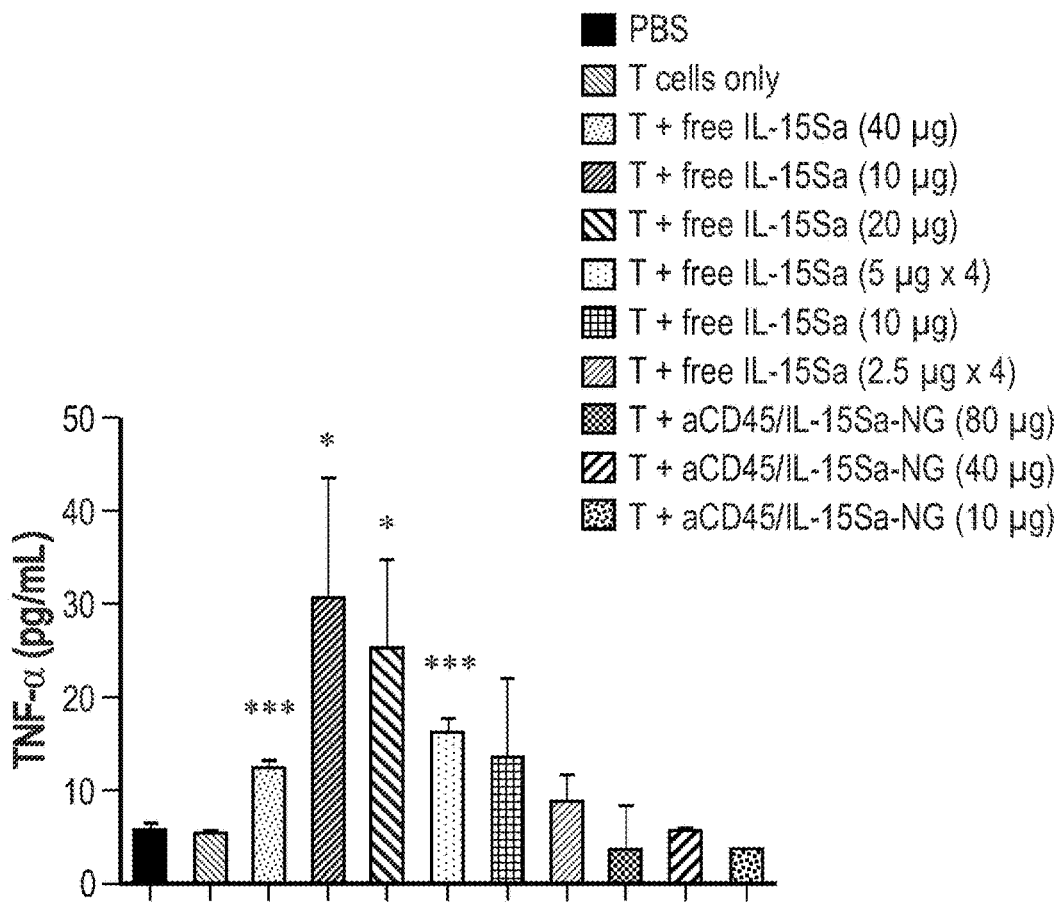
Figure 6E:
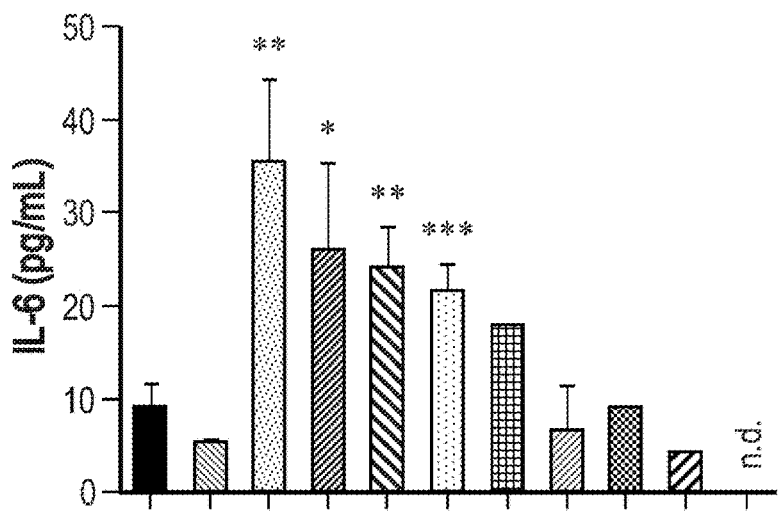

Animals receiving free high-dose IL-15Sa lost significant weight following therapy, which prompted us to evaluate the toxicity of IL-15Sa as a function of dose and delivery modality. Animals receiving >10 µg of free IL-15Sa steadily lost weight and eventually succumbed to lethal immunotoxicity irrespective of dosing regimen, setting the maximum tolerated dose (MTD) at 10 µg in this model (FIG. 6A). In contrast, when administered in the form of T-cell-bound NGs, no overt toxicity was observed up to the maximum achievable IL-15Sa loading per cell (80 µg IL-15Sa/$10 \times 10^6$ T-cells, FIG. 6A). Free IL-15Sa stimulated cytokine production from both pmel-1 and endogenous T-cells in the blood, in contrast to IL-15Sa delivered by NGs, where the majority of both backpacked and endogenous T-cells remained quiescent in the systemic circulation (FIG. 6B and FIG. 6C). In lymphoreplete animals, >10 µg free IL-15Sa does not elicit high levels of serum cytokine induction (*Biomaterials* 2012, 33, 5776-5787). However, in this lymphodepletion setting, ACT with >10 µg free IL-15Sa induced systemic cytokine release of TNF-α (FIG. 6D), IL-6 (FIG. 6E) and IL-10 (data not shown), and elevated liver enzymes, ALT and AST (data not shown). In contrast, backpacked T-cells (protein nanogel coupled T cells) elicited basal levels of these biomarkers up to the maximum administrable dosage. Thus, T-cell bound NGs limit stimulation of lymphocytes in the systemic circulation, enabling significantly greater IL-15Sa dosing.

To determine the impact of the increased therapeutic window afforded by IL-15Sa-NGs, we compared the antitumor efficacy of ACT with T-cells only, T-cells and free IL-15Sa (at the MTD of 10 µg), or NG-backpacked T-cells following the same treatment scheme as above. Tumor growth was significantly delayed in the 10 µg IL-15Sa-NG group compared to T-cells with free IL-15Sa support at the same dose. However, tumor suppression was further substantially enhanced by increasing the cytokine-NG dose, with animals treated at the maximal 80 µg dose showing a 1.7-fold increase in median survival relative to animals treated with the MTD of free IL-15Sa, an impressive response in this challenging tumor model. Notably, despite the use of a xenogeneic (human) IL-15Sa cytokine, no anti-hIL-15Sa antibodies above background were detected in serum following treatment in any of the NG-backpack-treated groups.

Example 6. TCR Signaling-Responsive Cytokine Nanogels Improve Efficacy of Human CAR T-Cell Therapy We evaluated whether NG-delivered cytokine could also positively impact the function of CAR T-cells, as an important modality of T-cell therapy in the clinic. For this purpose, we employed human CAR T-cells targeting EGFR in a luciferase-expressing human glioblastoma model in immunodeficient NSG mice. CAR T-cells were prepared using the huEGFRscFv-BBz chimeric antigen receptor (Johnson et. Al., 2015, *Sci Transl Med.*, 7(275); US2014/0271635A1) designed based on the heavy and light chains of cetuximab to form a single-chain variable fragment which was fused to a portion of the extracellular and transmembrane domains of human CD8α, followed by the intracellular domains of 4-1BB and CD3. The Bicistronic vector also encoded truncated human CD19 as a selectable marker, and was placed following a T2A ribosomal skip sequence. The plasmid coding hu EGFRscFv-BBz-CAR was synthesized and lentivirus packaging was produced by VectorBuilder. Isolated T-cells were derived from purchased leukapheresis products obtained from de-identified healthy donors under an IRB-approved protocol. T-cells were stimulated with Dynabeads Human T Activator CD3/CD28 (Life Technologies) at a bead to cell ratio 3:1. T-cells were cultured in RPMI 1640 medium supplemented with 10% fetal bovine serum, Hepes Buffer (20 mM), penicillin and streptomycin (1%) and IL-2 (20 IU/mL). T-cells were transduced (TDN) with CAR lentivirus and or left untransduced (UTD) one day following bead stimulation, and then T-cells were expanded for 10 days and cryopreserved until used. Surface expression of the CAR was confirmed and quantified with biotinylated human EGFR protein (ACRO Biosystems).

To test the ability of NG-delivered cytokines to improve the function of CAR T-cells, Luciferase-expressing U-87 MG human glioblastoma cells (American Tissue Culture Collection, Manassas, Va., USA) ($1.0 \times 10^6$) were injected s.c. in NSG mice (n=5/group). Animals received i.v. adoptive transfer of human T-cells ($2.6 \times 10^6$ total cells, 38% transduced with EGFR-targeting CAR ($1.0 \times 10^6$ CAR-T-cells)) on day 7. Animals were treated with sham saline injections, CAR-T alone, CAR-T followed by 13.8 µg of free IL-15Sa, or CAR-T-cells coupled with aCD45/IL-15Sa-NGs (13.8 µg). In vivo bioluminescence imaging of luciferase-expressing U-87 MG tumors over time was also measured. Individual tumour growth curves and survival curves of treatment groups were generated. Statistical analyses were performed using Two-Way ANOVA test for tumour growth data and Log-rank test for survival curves. Data represent the mean±s.e.m. *, p<0.05; , p<0.01; *, p<0.001; n.s., not significant.

Figure 7A:
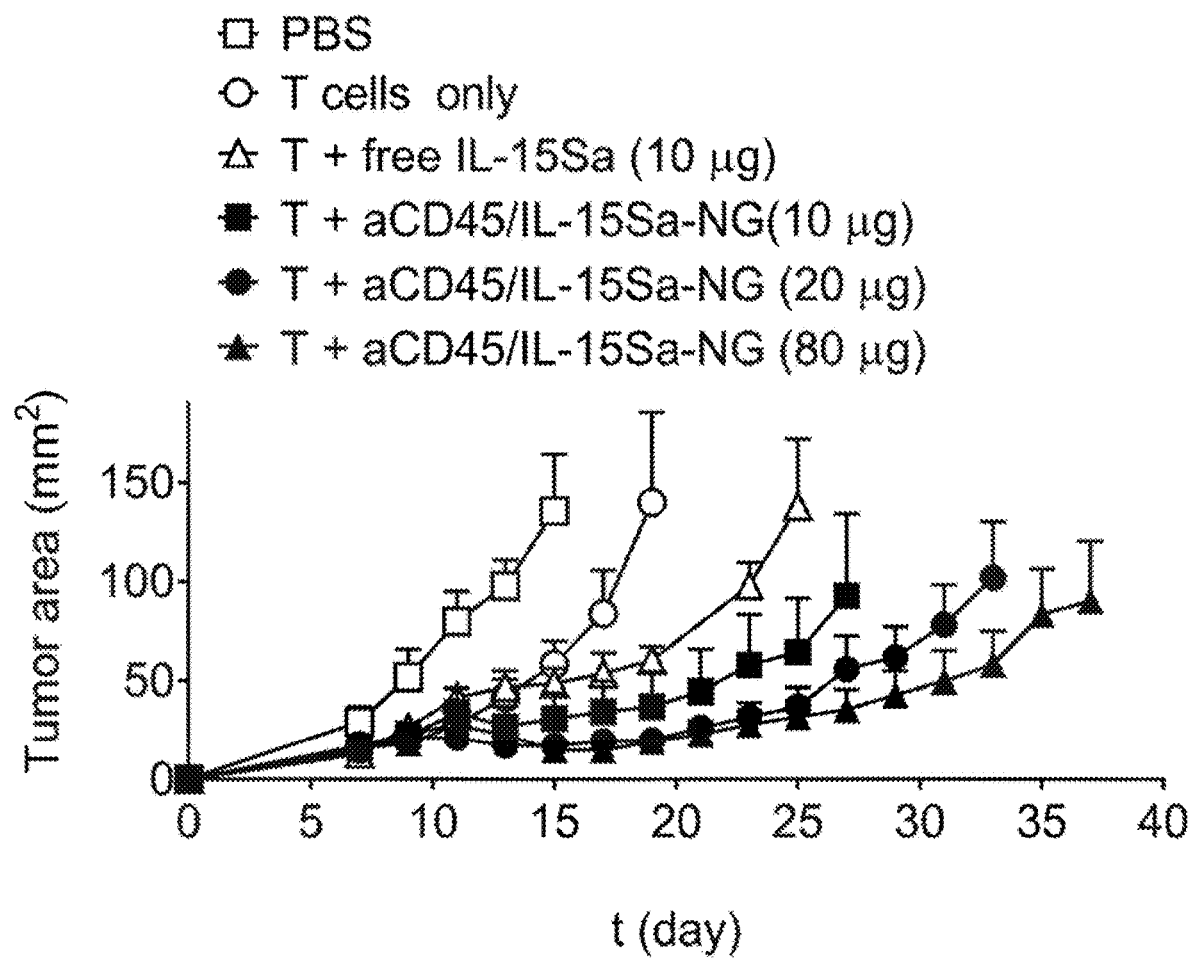
FIGS. 7A-7C show TCR signaling-responsive protein nanogels improve the efficacy of murine T-cell and human CAR T cell therapies.
Figure 7B:
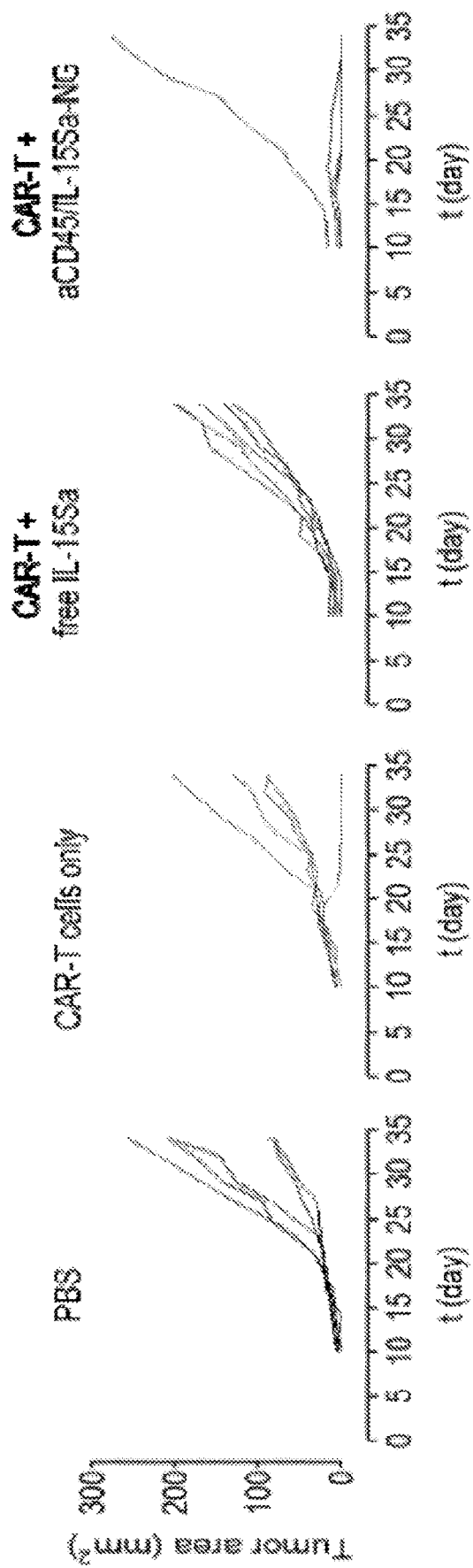
Figure 7C:
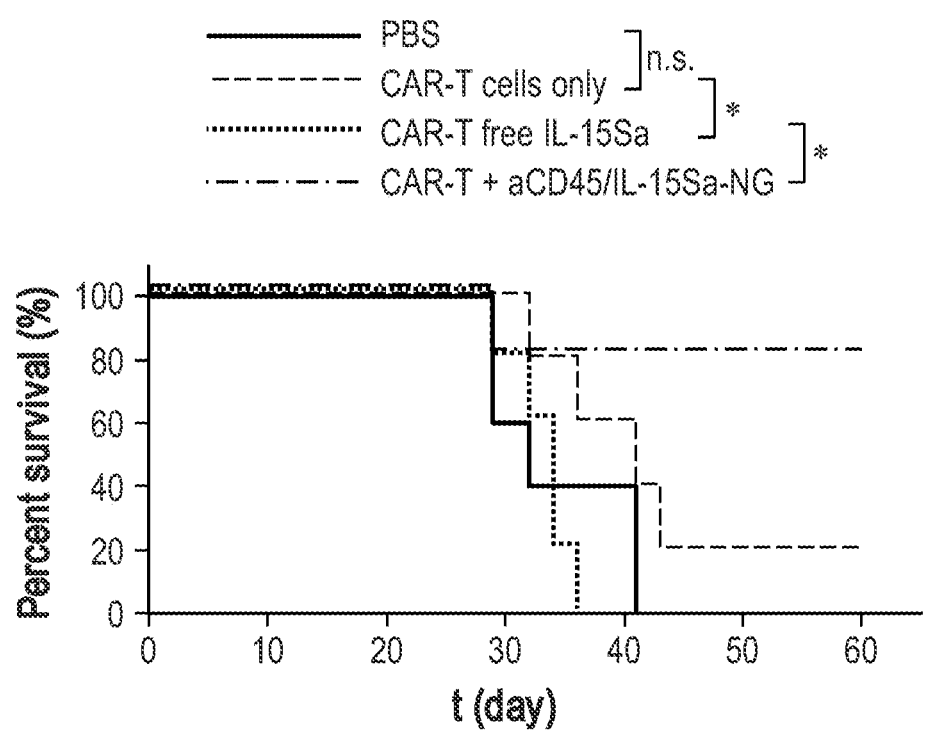

Tumor growth was significantly delayed in 10 µg IL-15Sa-NG group compared to T cells with free IL-15Sa support at the same dose (FIG. 7A). However, tumor suppression was further substantially enhanced by increasing the cytokine-NG dose (FIG. 7A), with animals treated at the maximal 80 µg dose showing a 1.7 fold increase in median survival relative to animals treated with the MTD of free IL-15Sa. CAR T-cells coupled with aCD45/IL-15Sa-NGs were compared to CAR T-cells alone or T-cells supplemented with an equivalent systemic dose of free IL-15Sa. Transfer of $10^6$ CAR-T-cells alone had a small impact on tumor growth and survival, which did not reach statistical significance; responses were marginally improved by the addition of free IL-15Sa (FIGS. 7B and 7C). By contrast, NG-coupled CAR T-cells eradicated tumors in 4 of 5 animals and increase animal survival (FIG. 7C). Thus, aCD45/IL-15Sa-NG delivery of cytokines was shown to enhance CAR T-cell therapy.

To measure serum antibody, serum samples were collected from treated mice in different groups at 30 days post ACT. Serum concentration of anti-IL-15Sa antibody was measured by a standard ELISA procedure with calibration of a monoclonal anti-human IL-15 antibody (eBioscience).

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of treating a tumor in a subject, the method comprising administering to the subject a composition comprising:
   (i) a nucleated carrier cell that homes to a tumor and expresses CD45 and a cytokine receptor on its surface; and
   (ii) a protein nanogel comprising cytokines that interact with said cytokine receptor, wherein the cytokines are reversibly and covalently crosslinked to each other through a degradable linker,
   wherein the nanogel is coupled to the surface of the nucleated carrier cell with an anti-CD45 monoclonal antibody, thereby treating cancer.

2. The method of claim 1, wherein the carrier cell comprises a negatively charged cell membrane and the nanogel comprises a polycation surface which interacts electrostatically with the cell membrane.

3. The method of claim 2, wherein the polycation surface comprises is polylysine or polyethylene glycol-b-polylysine (PEG-PLL).

4. The method of claim 1, wherein the degradable linker degrades under physiological conditions to release as intact proteins, the cytokines.

5. The method of claim 1, wherein the carrier cell is a T cell, a B cell, a Natural Killer (NK) cell or a hematopoietic progenitor cell.

6. The method of claim 5, wherein the carrier cell is a T cell.

7. The method of claim 6, wherein the T cell is a CD8+ T cell, a CD4+ T cell, an adoptively transferred T cell, or a chimeric antigen receptor (CAR) T cell.

8. The method of claim 1, wherein the cytokines are selected from the group consisting of IL-2, IL-12, IL-15, IL-15-SA, IL-15RaSu/Fc, IL-18, CCL5, and combinations thereof.

9. The method of claim 8, wherein the IL-15-SA comprises a complex comprising a dimeric IL-15RαSu/Fc and two IL-15 molecules.

10. The method of claim 9, wherein the dimeric IL-15RαSu/Fc comprises an amino acid sequence set forth in SEQ ID NO: 2 and the IL-15 molecules are wild-type IL-15 molecules or mutant IL-15 molecules.

11. The method of claim 1, wherein the protein nanogel comprises a single type of cytokine or more than one type of cytokine.

12. The method of claim 11, wherein the protein nanogel comprises 2, 3, 4, 5 or more different cytokines.

13. The method of claim 12, wherein the cytokines are selected from IL-15, IL-15-SA, IL-15RaSu/Fc or IL-12.

14. The method of claim 4, wherein the degradable linker degrades gradually over a time course between one day to two weeks.

15. The method of claim 1, wherein the composition is administered in combination with a biologically active protein.

16. A method of treating a tumor in a subject, the method comprising administering to the subject a composition comprising:
(i) a nucleated carrier cell that homes to a tumor and expresses CD45 and an IL-2 receptor on its surface; and
(ii) a protein nanogel comprising IL-2 polypeptides reversibly and covalently crosslinked to each other through a degradable linker,
wherein the nanogel is coupled to the surface of the nucleated carrier cell with an anti-CD45 monoclonal antibody, thereby treating cancer.

17. The method of claim 16, wherein the composition is administered in combination with a biologically active protein.

18. A method of treating a tumor in a subject, the method comprising administering to the subject a composition comprising:
(i) a nucleated carrier cell that homes to a tumor and expresses CD45 and an IL-15 receptor on its surface; and
(ii) a protein nanogel comprising IL-15 polypeptides reversibly and covalently crosslinked to each other through a degradable linker,
wherein the nanogel is coupled to the surface of the nucleated carrier cell with an anti-CD45 monoclonal antibody, thereby treating cancer.

19. The method of claim 18, wherein the IL-15 polypeptides are selected from IL-15, IL-15-SA, IL-15RaSu/Fc, or a combination thereof.

20. The method of claim 18, wherein the composition is administered in combination with a biologically active protein.

* * * * *